(12) United States Patent
Swaminathan

(10) Patent No.: US 9,981,012 B2
(45) Date of Patent: May 29, 2018

(54) COMPOSITIONS AND METHODS FOR PROTECTING THE KIDNEY FROM ISCHEMIA REPERFUSION INJURY

(71) Applicant: University of Virginia Patent Foundation, Charlottesville, VA (US)

(72) Inventor: Sundararaman Swaminathan, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days. days.

(21) Appl. No.: 15/026,574

(22) PCT Filed: Sep. 22, 2014

(86) PCT No.: PCT/US2014/056751
§ 371 (c)(1),
(2) Date: Mar. 31, 2016

(87) PCT Pub. No.: WO2015/042515
PCT Pub. Date: Mar. 26, 2015

(65) Prior Publication Data
US 2016/0263195 A1 Sep. 15, 2016

Related U.S. Application Data

(60) Provisional application No. 61/880,272, filed on Sep. 20, 2013.

(51) Int. Cl.
| | | |
|---|---|---|
| *A61K 31/44* | (2006.01) | |
| *A61K 33/26* | (2006.01) | |
| *A61K 38/22* | (2006.01) | |
| *A61K 45/06* | (2006.01) | |
| *A61K 38/17* | (2006.01) | |
| *A61K 31/436* | (2006.01) | |
| *A61K 31/568* | (2006.01) | |
| *A61K 31/565* | (2006.01) | |

(52) U.S. Cl.
CPC ............ *A61K 38/22* (2013.01); *A61K 31/436* (2013.01); *A61K 31/44* (2013.01); *A61K 31/565* (2013.01); *A61K 31/568* (2013.01); *A61K 33/26* (2013.01); *A61K 38/1709* (2013.01); *A61K 45/06* (2013.01)

(58) Field of Classification Search
CPC .. A61K 2300/00; A61K 31/436; A61K 31/44; A61K 31/565; A61K 31/568; A61K 33/26; A61K 38/1709; A61K 38/22; A61K 45/06
USPC .................................................. 514/1.1, 21.3
See application file for complete search history.

(56) References Cited

U.S. PATENT DOCUMENTS

| | | | | |
|---|---|---|---|---|
| 9,684,002 | B2 * | 6/2017 | Westerman | ............ G01N 33/70 |
| 2006/0019339 | A1 | 1/2006 | Lauth et al. | |
| 2007/0218063 | A1 | 9/2007 | Skurkovich et al. | |
| 2010/0204122 | A1 * | 8/2010 | Huang | ................... A61K 38/22 |
| | | | | 514/1.1 |
| 2011/0053268 | A1 | 3/2011 | Tomosugi | |

FOREIGN PATENT DOCUMENTS

| | | |
|---|---|---|
| WO | WO2011143232 | 11/2011 |
| WO | WO2013086143 | 6/2013 |

OTHER PUBLICATIONS

Shah, et al., "The role of catalytic iron in acute kidney injury", Clin. J. Am. Soc. Nephrol., Oct. 1, 2011, vol. 6, pp. 2329-2331.
Hingorani, et al., "Ironing out the pathogenesis of acute kidney injury", Am. J. Kidney Dis., Apr. 1, 2009, vol. 53, pp. 569-571.
Mishra, et al., "Amelioration of ischemic acute renal injury by neutrophil gelatinase-associated lipocalin", J. Am. Soc. Nephol., Dec. 1, 2004, vol. 15, pp. 3073-3082.
Zhou, et al., "Elevated expression of hepcidin post-renal ischemia reperfusion injury", Acta Biochim Biophys Sin, Feb. 24, 2013, vol. 45, pp. 342-344.
Haase, et al., "Novel Biomarkers, oxidative stress, and the role of labile iron toxicity in cardiopulmonary bypass-associated acute kidney injury", J. Am. Coll. Cardiol., May 11, 2010, vol. 55, pp. 2024-2033.
Schnellmann, et al., "Chapter 15, Pathophysiology of Nephrotoxic Acute Renal Failure", Book entitled "Atlas of Disease of the Kidney", edited by Berl, et al., kidneyatlas.org, Jan. 6, 1999, pp. 15.1-15.14, available at http://www.kidneyatlas.org/book1/adk1_15.pdf.
Zhang, et al. "Role of Reactive Oxygen Species in Mediating Hepatic Ischemia-Reperfusion Injury and Its Therapeutic Applications in Liver Transplantation", Transplantation Proceedings, 39, pp. 1332-1337 (2007).

(Continued)

*Primary Examiner* — Julie Ha
(74) *Attorney, Agent, or Firm* — Rodney L. Sparks

(57) ABSTRACT

The effects of hepcidin treatment on mitigating renal ischemiareperfusion injury (IRI) and acute kidney injury (AKI) by decreasing iron availability and ROS-mediated cell death were tested. C57Bl/6 (WT) and hepcidin knock out (Hamp$^{-/-}$) mice were treated with saline or 50 μg of hepcidin i.p. prior to bilateral renal IRI. Renal function, injury markers, histopathology, and inflammation were examined after 24 hours of reperfusion. In WT mice, IRI induced increases in serum and kidney non-heme iron levels, but hepcidin treatment induced sequestration of iron in the spleen and liver and prevented IRI-associated increases in serum and kidney non-theme iron. Kidney function was significantly better in hepcidin-treated mice, accompanied by less acute tubular necrosis and reduced infiltration of immune cells. Hepcidin treatment decreased kidney ferroportin expression and induced the expression of cytoprotectant, H-Ferritin, and was associated with less ROS and tubular epithelial apoptosis. These results demonstrate a protective role of hepcidin in IRI and AKI.

22 Claims, 33 Drawing Sheets

(12 of 33 Drawing Sheet(s) Filed in Color)

(56) References Cited

OTHER PUBLICATIONS

De Vries, et al., "Reduction of circulating redox-active iron by apotransferrin protects against renal ischemia-reperfusion injury", Transplantation. 2004;77(5):669-75.
Abboud, et al., "A novel mammalian iron-regulated protein involved in intracellular iron metabolism", J Biol Chem. 2000;275(26):19906-12.
De Domenico, et al., "The molecular mechanism of hepcidin-mediated ferroportin down-regulation", Molecular biology of the cell. 2007;18(7):2569-78.
Moulouel B, et al., "Hepcidin regulates intrarenal iron handling at the distal nephron", Kidney international, 2013;84(4):756-66.
Park, et al., "Hepcidin, a urinary antimicrobial peptide synthesized in the liver", J Biol Chem. 2001;276(11):7806-10.
Nemeth, et al., "Hepcidin regulates cellular iron efflux by binding to ferroportin and inducing its internalization", Science. 2004;306(5704):2090-3.
Nemeth E., "Targeting the hepcidin-ferroportin axis in the diagnosis and treatment of anemias", Advances in hematology 2010;2010, 750643, 1-9.
Kroot, et al., "Hepcidin in human iron disorders: diagnostic implications", Clin. Chem. 57, 1650-1669 (2011).
Ho J, et al., "Urinary hepcidin-25 and risk of acute kidney injury following cardiopulmonary bypass", Clinical journal of the American Society of Nephrology : CJASN. 2011;6(10):2340-6.
Arkadopoulos, N., et al., "Iron chelation for amelioration of liver ischemia-reperfusion injury", Hemoglobin. 2010;34(3):265-77.
De Domenico I, et al., Hepcidin mediates transcriptional changes that modulate acute cytokine-induced inflammatory responses in mice, J Clin Invest. Jul. 2010;120(7):2395-405.
Ruchala and Nemeth, 2014, "The pathophysiology and pharmacology of hepcidin", Trends in Pharmacological Sciences, 35:3:155-161.
Young et al., "Hemojuvelin Modulates Iron Stress During Acute Kidney Injury: Improved by Furin Inhibitor", Antioxid Redos Signal, 2014, 20:8:1181-1194 (epub. Sep. 17, 2013).
Gaun et al., "A chemical screen identifies small molecules that regulate hepcidin expression", Blood Cells Molecules and Diseases, 53 (2014) 231-204 (Available online Jul. 4, 2014).
Anja Haase-Fielitz, et al., "Urine hepcidin has additive value in ruling out cardiopulmonary bypass-associated acute kidney injury: an observational cohort study", Critical Care, Biomed Central Ltd., London, GB, vol. 15, No. 4, Aug. 4, 2011 (Aug. 4, 2011), p. R186.
Prowle, J.R., et al., "Greater increase in urinary hepcidin predicts protection from acute kidney injury after cardiopulmonary bypass", Nephrology Dialysis Transplantation, vol. 27, No. 2, Feb. 1, 2012 (Feb. 1, 2012), pp. 595-602.

* cited by examiner

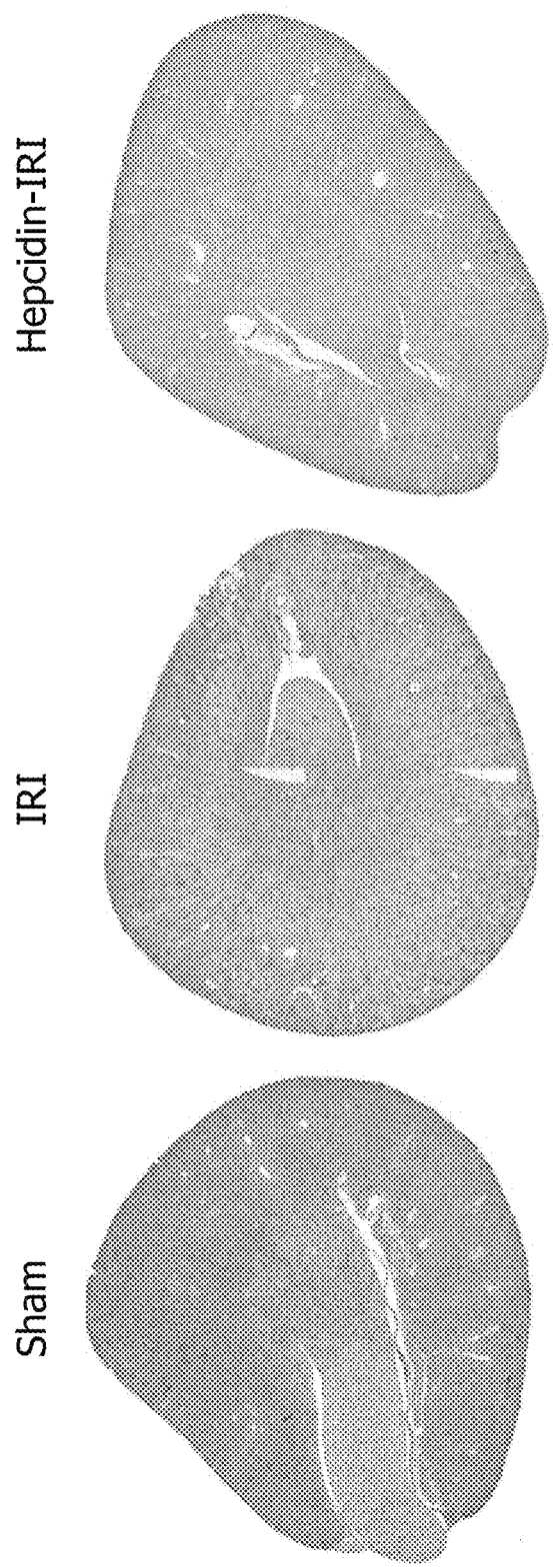

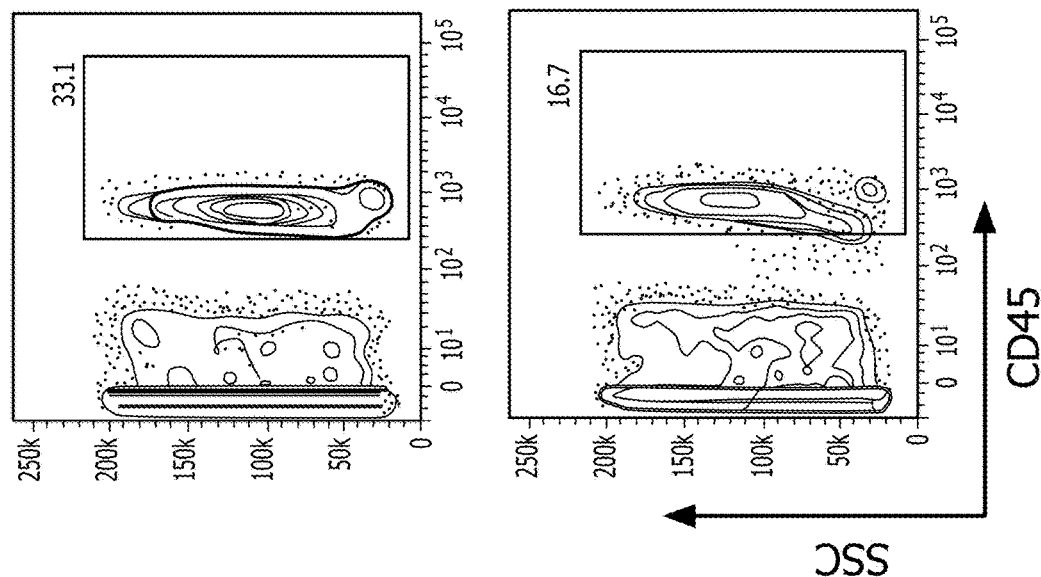
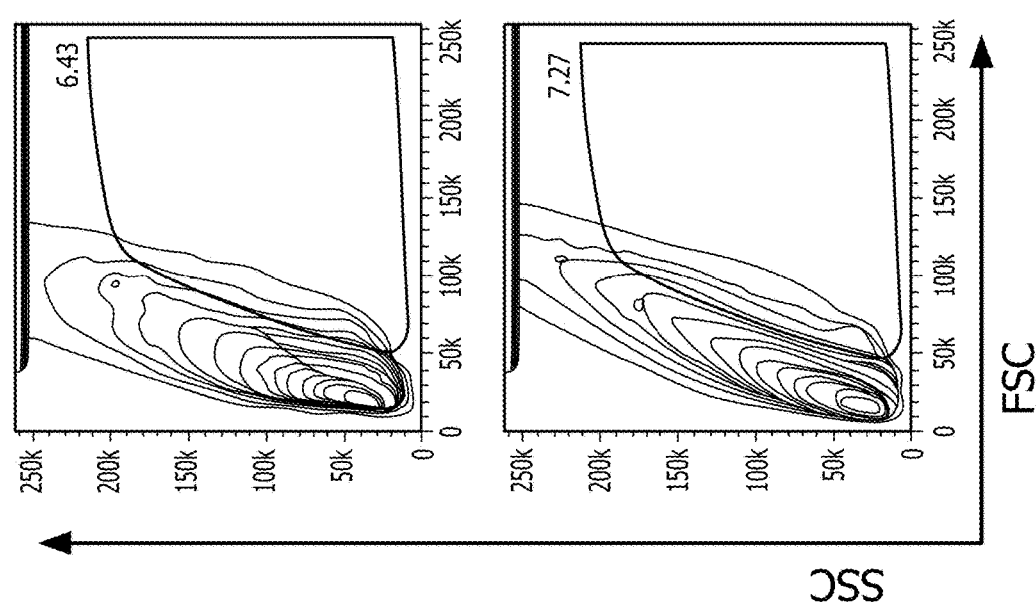
FIG. 4b

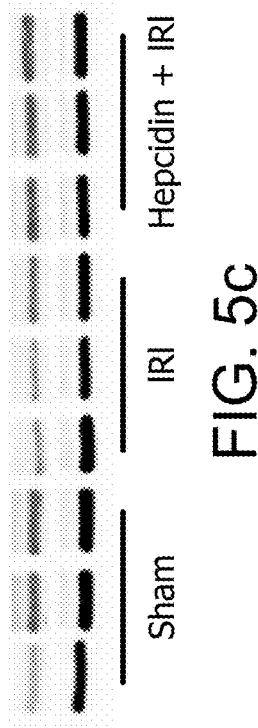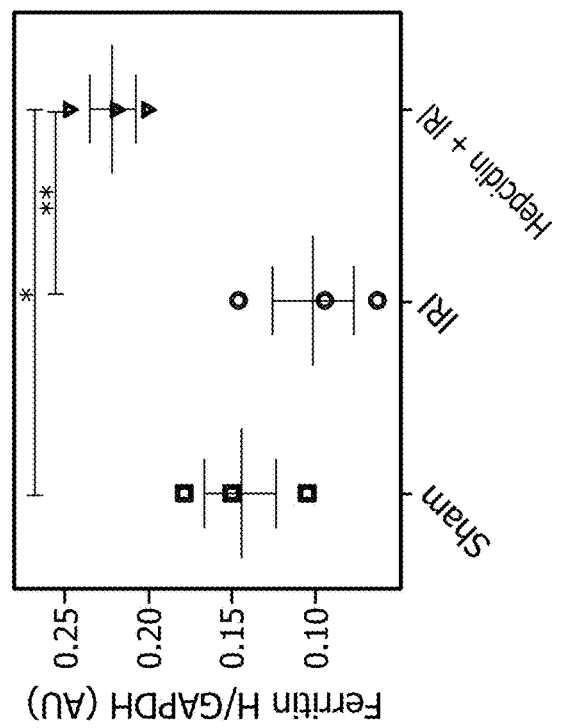
FIG. 5a
FIG. 5b
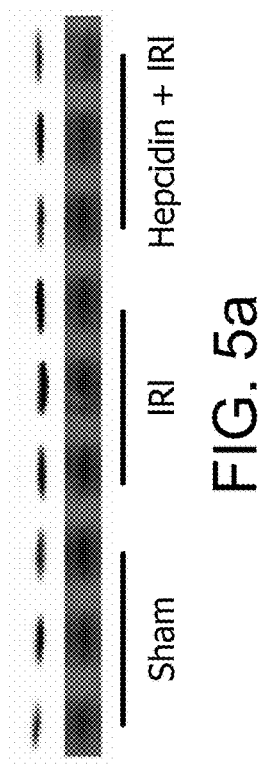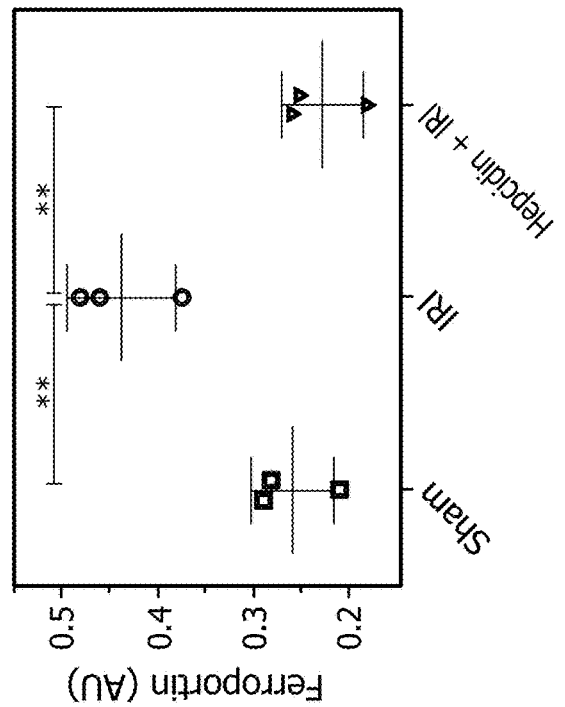
FIG. 5c
FIG. 5d

HAMP$^{-/-}$-IRI

HAMP$^{-/-}$-Hepcidin-IRI

*P = 0.0001, **P < 0.0001

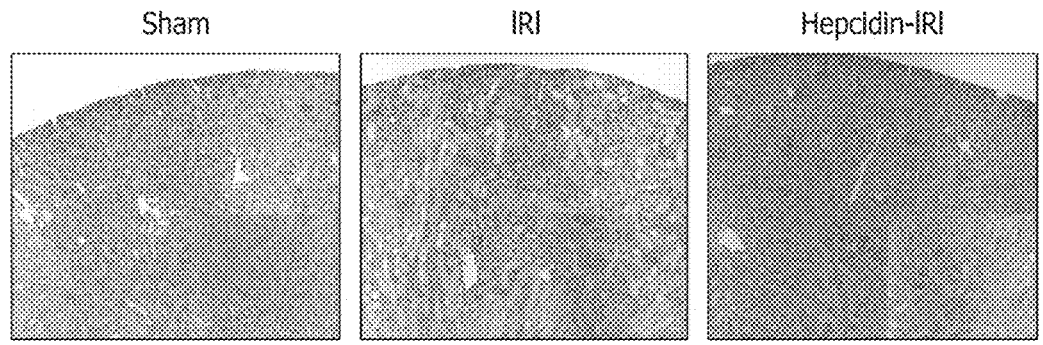
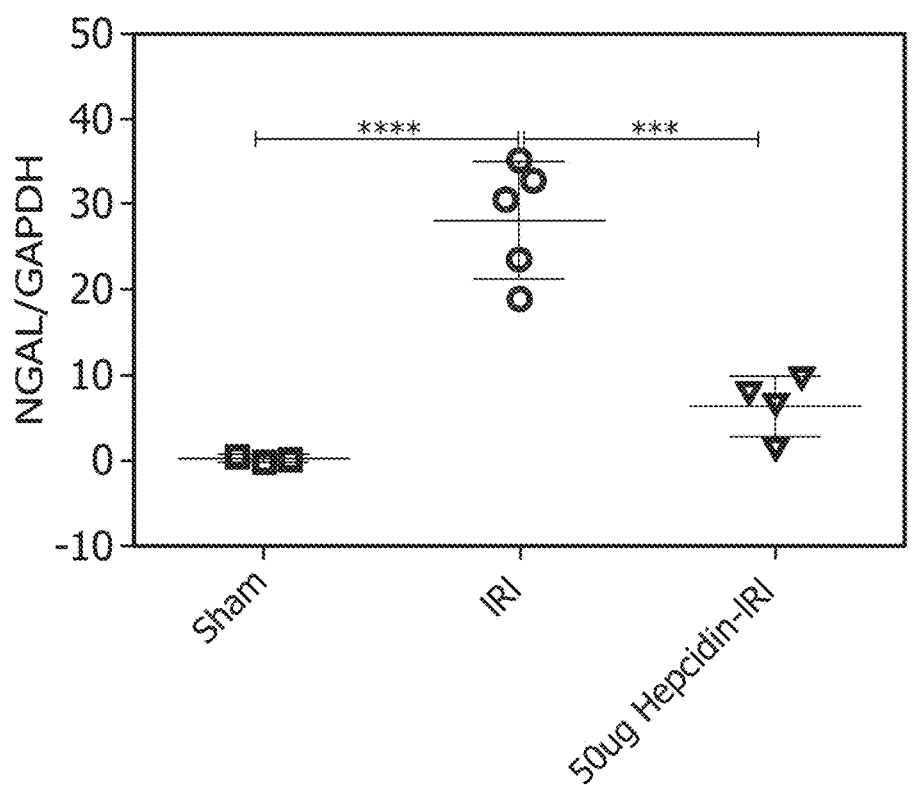
FIG. 12d

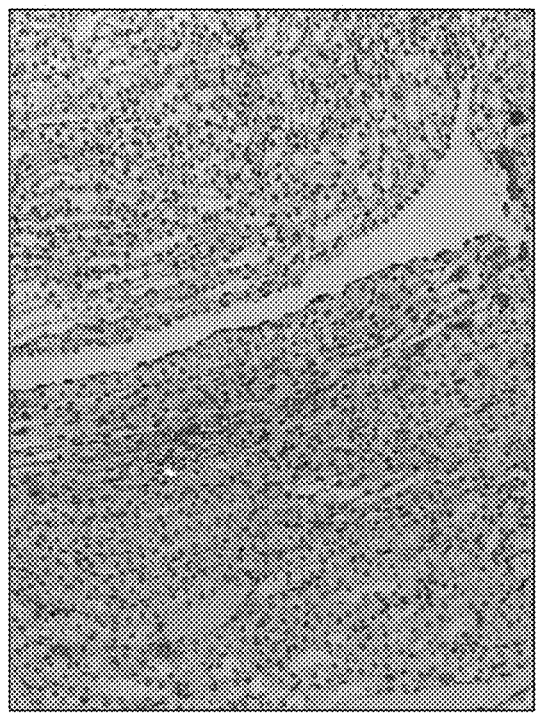
FIG. 13b  Hepcidin + IRI
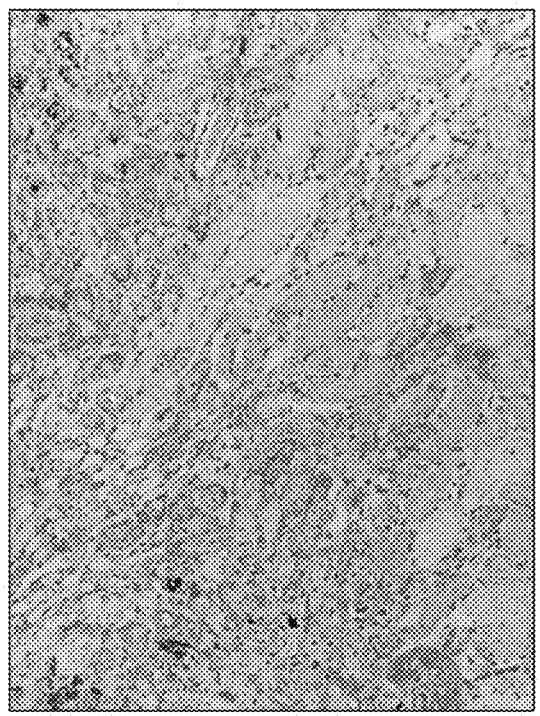
FIG. 13a  IRI

SEQUENCE LISTING

<160> NUMBER OF SEQ ID NOS: 5

<210> SEQ ID NO 1
<211> LENGTH: 25
<212> TYPE: PRT
<213> ORGANISM: Mus musculus

<400> SEQUENCE: 1

Asp Thr Asn Phe Pro Ile Cys Ile Phe Cys Cys Lys Cys Cys Asn Asn
1               5                   10                  15

Ser Gln Cys Gly Ile Cys Cys Lys Thr
            20                  25

<210> SEQ ID NO 2
<211> LENGTH: 25
<212> TYPE: PRT
<213> ORGANISM: Homo sapiens

<400> SEQUENCE: 2

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 3
<211> LENGTH: 84
<212> TYPE: PRT
<213> ORGANISM: homo sapiens

<400> SEQUENCE: 3

Met Ala Leu Ser Ser Gln Ile Trp Ala Ala Cys Leu Leu Leu Leu Leu
1               5                   10                  15

Leu Leu Ala Ser Leu Thr Ser Gly Ser Val Phe Pro Gln Gln Thr Gly
            20                  25                  30

Gln Leu Ala Glu Leu Gln Pro Gln Asp Arg Ala Gly Ala Arg Ala Ser
            35                  40                  45

Trp Met Pro Met Phe Gln Arg Arg Arg Arg Arg Asp Thr His Phe Pro
        50                  55                  60

Ile Cys Ile Phe Cys Cys Gly Cys Cys His Arg Ser Lys Cys Gly Met
65                  70                  75                  80

Cys Cys Lys Thr

<210> SEQ ID NO 4
<211> LENGTH: 83
<212> TYPE: PRT
<213> ORGANISM: Mus musculus

<400> SEQUENCE: 4

Met Ala Leu Ser Thr Arg Thr Gln Ala Ala Cys Leu Leu Leu Leu Leu
1               5                   10                  15

Leu Ala Ser Leu Ser Ser Thr Thr Tyr Leu His Gln Gln Met Arg Gln
            20                  25                  30

Thr Thr Glu Leu Gln Pro Leu His Gly Glu Glu Ser Arg Ala Asp Ile
            35                  40                  45

Ala Ile Pro Met Gln Lys Arg Arg Lys Arg Asp Thr Asn Phe Pro Ile
        50                  55                  60

Cys Ile Phe Cys Cys Lys Cys Cys Asn Asn Ser Gln Cys Gly Ile Cys
65                  70                  75                  80

Cys Lys Thr

```
<210> SEQ ID NO 5
<211> LENGTH: 84
<212> TYPE: PRT
<213> ORGANISM: Rattus rattus

<400> SEQUENCE: 5

Met Ala Leu Ser Thr Arg Ile Gln Ala Ala Cys Leu Leu Leu Leu Leu
1               5                   10                  15

Leu Ala Ser Leu Ser Ser Gly Ala Tyr Leu Arg Gln Gln Thr Arg Gln
                20                  25                  30

Thr Thr Ala Leu Gln Pro Trp His Gly Ala Glu Ser Lys Thr Asp Asp
            35                  40                  45

Ser Ala Leu Leu Met Leu Lys Arg Arg Lys Arg Asp Thr Asn Phe Pro
        50                  55                  60

Ile Cys Leu Phe Cys Cys Lys Cys Cys Lys Asn Ser Ser Cys Gly Leu
65                  70                  75                  80

Cys Cys Ile Thr
```

COMPOSITIONS AND METHODS FOR PROTECTING THE KIDNEY FROM ISCHEMIA REPERFUSION INJURY

CROSS REFERENCE TO RELATED APPLICATIONS

This application is a national stage filing of International Application No. PCT/US2014/056751, filed Sep. 22, 2014, which claims benefit of priority pursuant to 35 U.S.C. § 119(e) to U.S. provisional patent application No. 61/880,272, filed on Sep. 20, 2013. The entire disclosures of the afore-mentioned patent applications are incorporated herein by reference.

BACKGROUND

Renal ischemia-reperfusion injury (IRI) is a major cause of acute kidney injury (AKI) in many clinical settings including cardiovascular surgery, sepsis, and kidney transplantation. Ischemic AKI is associated with increased morbidity, mortality, and prolonged hospitalization (1, 2).

Acute ischemia leads to depletion of adenosine triphosphate (ATP), inducing tubular epithelial cell (TEC) injury, and hypoxic cell death. Reperfusion further amplifies injury by promoting the formation of reactive oxygen species (ROS), and inducing leukocyte activation, infiltration, and inflammation (3-6).

Multiple studies have shown the important role of iron and ROS in mediating apoptotic and necrotic cell death and the ensuing inflammatory response during the course of IRI (7, 8). The ischemic stage of the injury results in mitochondrial membrane depolarization, DNA fragmentation, translocation of cytochromes from the mitochondria into the cytosol (9, 10) and breakdown of heme proteins like the cytochrome c results in a reduction of heme associated ferric ($Fe^{3+}$) iron to ferrous ($F^{e2+}$) iron and thereby increase the levels of catalytically active or labile form of iron (11-13). A key pathological characteristic of labile iron ($Fe^{2+}$) is its ability to catalyze the generation of tissue damaging hydroxyl radical (OH—) by an interaction with superoxide anion ($O^{-2}$) and hydrogen peroxide ($H_2O_2$) via Haber-Weiss reaction, both of which are increased during IRI (7, 14). Labile iron's contribution to oxidative stress and cellular damage has been demonstrated not only in renal ischemia reperfusion injury (15, 16) but also in other models of AKI (17, 18) and iron chelation with desferrioxamine induces protection in diverse animals models of AKI (19).

Iron ($Fe^{2+}$) is exported from the cells by the only known iron export protein, ferroportin (20). Ferroportin is significantly expressed on macrophages, hepatocytes, renal proximal and distal tubular cells, and enterocytes (21-23). Intracellular iron levels regulate ferroportin expression; high intracellular iron induces ferroportin-mediated iron export into circulation (20). To sustain physiologic iron requirement yet avoid iron toxicity, an endogenous peptide hormone Hepcidin (HAMP), primarily produced by hepatocytes (23, 24), and regulates systemic iron balance. The main known function of HAMP is to covalently modify ferroportin, which leads to its internalization and lysosomal degradation, and thereby prevent cellular iron egress (25, 26). HAMP is acutely and positively regulated during iron imbalance (25), inflammation (27, 28) and has antibacterial properties (29, 30; see also 60 and 61). Hypoxia, however, negatively regulates it (31). While human studies have indicated a positive correlation between increased urinary Hepcidin levels and protection against AKI, a direct pathogenic role of hepcidin has not been examined in any model of AKI (32).

Mature hepcidin is a 25 amino acid (a.a.) residue peptide. Its production appears to be regulated at the transcriptional level and major stimuli regulating hepcidin production include iron and the regulatory signals pertaining to erythropoietic demands for iron. Hepcidin is also an acute-phase reactant and increases during inflammation. Other hepcidin regulators include hepatocyte growth factor (HGF), epidermal growth factor (EGF), steroid hormones (estrogen, testosterone), and metabolic pathways (starvation/gluconeogenesis). Hepcidin production increases in response to iron loading and this prevents further absorption of dietary iron and the development of iron overload. Plasma iron and liver iron stores regulate hepcidin transcription. Both serum iron and liver iron accumulation activate the BMP receptor and its Smad1/5/8 pathway, and increase hepcidin mRNA concentrations in hepatocytes. The BMP co-receptor hemojuvelin (HJV) is also required for this response.

For extracellular iron, transferrin receptors 1 and 2 (TfR1 and TfR2) are the likely sensors of holo-transferrin concentrations. At higher holo-Tf concentrations, HFE is displaced from TfR1 and associates with TfR2. HFE and TfR2 in turn may interact with HJV, thus potentiating BMP signaling.

Mutations in Hfe, TfR2, Hjv, Bmp6, BMP receptors Alk2 and Alk3, and Smad4 all impair hepcidin regulation by iron. Hepcidin production is further modulated by the transmembrane serine protease TMPRSS6, also known as matriptase-2, and by neogenin, a multifunctional transmembrane receptor. It has been proposed that these proteins act by post-translationally regulating the levels of membrane-associated HJV. The specific involvement of these proteins in iron sensing is also uncertain.

Hepcidin is suppressed in conditions associated with increased erythropoietic activity. Hemorrhage, hemolysis, and injections of erythropoietin all result in a rapid decrease in hepcidin. In anemias with ineffective erythropoiesis, hepcidin levels are chronically suppressed. This is thought to be the cause of iron overload in nontransfused patients. Hepcidin increases rapidly following inflammatory and infectious stimuli via the IL-6 pathway. Because hepcidin deficiency or excess plays important roles in the pathogenesis of various iron disorders, hepcidin agonists and antagonists may be potentially useful in clinical practice.

Hepcidin agonists such as PR73 (a minihepcidin) are compounds that can mimic the function of hepcidin or potentiate its endogenous synthesis and may be able to prevent systemic accumulation of iron (See Ganz et al., International Pat. Pub. WO2013086143 A1). Such compounds may provide additional treatment options for patients who do not respond well to standard treatment regimens. Minihepcidins are peptide-based hepcidin agonists that were rationally designed based on the region of hepcidin that interacts with ferroportin. A nine amino acid N-terminal fragment of hepcidin (DTHFPICIF) is crucial for its hormonal activity. This particular fragment was further engineered: unnatural amino acids (N-substituted and β-homo amino acids) were introduced to increase resistance to proteolysis, and fatty acids were conjugated to prolong the half-life in circulation. This yielded analogs that are at least as potent as full-length hepcidin and have a longer duration of action. One such analog, the minihepcidin PR65, was tested in hepcidin knockout mice, a model of severe hemochromatosis. Treatment prevented the development of iron overload in non-overloaded hepcidin knockout mice. Treatment of mice with pre-existing iron overload was less effective but still led to partial redistribution of iron from the liver to the spleen within 2 weeks. At high doses, PR65 caused profound iron restriction and anemia, indicating that minihepcidin therapy will likely require titration to effect to avoid excessive hypoferremia and iron restriction.

Hepcidin production can be increased by antagonizing TMPRSS6, a negative regulator of hepcidin. Homozygous inactivation of Tmprss6 in thalassemic th3/+ mice increased hepcidin levels, ameliorated iron overload, and improved ineffective erythropoiesis. Targeting Tmprss6 with RNA-based therapeutics such as antisense oligonucleotides (ASOs) and siRNAs against Tmprss6 was effective in a mouse model of iron overload.

Hepcidin production can also be stimulated by BMP6 and its agonists. In patients undergoing low-molecular-weight heparin therapy to prevent deep vein thrombosis, serum hepcidin concentrations decreased by ~80% within 2-5 days after the start of the treatment. This was associated with increased serum iron and transferrin saturation. Heparin itself is an anti-inflammatory agent, which may be a contributory factor in its anti-hepcidin activity. HJV, a BMP co-receptor essential for hepcidin expression, is another molecular target that can be exploited to interfere with hepcidin production. Membrane-linked HJV and its soluble form (shave) have opposing effects on hepcidin expression, and shave decreases Smad signaling and hepcidin levels. Soluble HJV-Fc fusion protein (sHJV.Fc) ameliorated anemia of inflammation (AI) in a rat model in which AI was induced with group A streptococcal peptidoglycan-polysaccharide (PG-APS). Four-week therapy resulted in increased hemoglobin and serum iron, although hepcidin mRNA had not significantly decreased by this point.

LDN-193189, a derivative of dorsomorphin which specifically antagonizes the kinase activity of BMP receptor isotypes ALK2, ALK3, and ALK6, effectively reversed anemia in the rat model of AI caused by PG-APS.

Inflammation induces hepcidin expression via IL-6-Stat3 and possibly other pathways and neutralizing monoclonal antibodies directed against IL-6 or IL-6 receptors can be used to decrease hepcidin synthesis in animal models and humans with inflammatory conditions.

There is a long felt need in the art for compositions and methods useful for preventing and treating acute kidney injury associated with renal ischemia reperfusion, including during surgery such as transplant surgery. The present invention satisfies these needs.

SUMMARY OF THE INVENTION

It is disclosed herein that renal IRI induces unique dynamic changes in renal and extra-renal iron homeostasis characterized by ferroportin-dependent splenic iron egress and renal iron accumulation. Hepcidin knockout mice that demonstrate constitutive overexpression of ferroportin sustain more severe renal injury after IRI. It is further disclosed herein that synthetic Hepcidin mitigates renal IRI through reducing circulating iron levels, by inducing hepatosplenic iron sequestration and by reducing inflammation and oxidative stress. The results disclosed herein suggest that hepcidin therapy, including the use of synthetic fragments of hepcidin, may represent an effective novel strategy for the mitigation of renal IRI. In one aspect, hepcidin is protective against folic acid induced acute kidney injury (data not shown).

Acute kidney injury resulting from other causes can also be treated or protected by hepcidin therapy and include, but are not limited to, myoglobinuric acute kidney injury, acute kidney injury induced by hypotensive shock, sepsis-associated acute kidney injury, toxic acute kidney injury such as after aminoglycoside therapy or cancer chemotherapy, acute kidney injury induced by iodinated contrast media (CI-AKI). CI-AKI is a common cause of acute kidney injury which can be predicted by certain risk factors and hepcidin may have a useful application.

Therefore, the present invention provides compositions and methods useful for preventing or treating acute kidney injury associated with renal ischemia reperfusion injury and with other causes of acute kidney injury. The method comprises administering to a subject a pharmaceutical composition comprising an effective amount of at least one hepcidin or a biologically active fragment or homolog thereof, and optionally a pharmaceutically acceptable carrier. In one aspect, the composition further comprises at least one inducer of hepcidin and optionally an additional therapeutic agent.

The present invention provides for the use of hepcidin as described herein, as well as biologically active fragments and homologs thereof (e.g., SEQ ID NOs:1-5). In one aspect, the hepcidin is mammalian. In one aspect, the hepcidin is human. In one aspect, the hepcidin is synthetic. In one embodiment, hepcidin or biologically active fragments or homologs thereof are useful for protecting the kidney from injuries associated with renal IRI. The present invention provides for administering a pharmaceutical composition to a subject in need, wherein the composition comprises hepcidin or a biologically active fragment or homolog thereof, and optionally a pharmaceutically-acceptable carrier and optionally at least one additional therapeutic agent.

In another aspect, the administration of a hepcidin protein or peptide of the invention can be performed at the same time other therapies are being administered. One of ordinary skill in the art will appreciate that numerous techniques are known for determining the best routes, dosages, and timing of administration, as well as how many times administration should occur.

The present invention provides compositions and methods useful for protecting the kidney from injury associated with renal ischemia reperfusion injury. The treatments described herein are useful for, inter alia: preventing or treating oxidative stress associated injury in the kidney; inhibiting increased serum iron levels associated with ischemia reperfusion injury; inhibiting kidney iron accumulation; increasing splenic non-heme iron levels; inhibiting a decrease in liver non-heme iron; inhibiting increased hepcidin gene expression; inhibiting increased endogenous serum hepcidin levels; inhibiting increased plasma creatinine levels; inhibiting kidney tubular necrosis; inhibiting renal epithelial apoptosis; inhibiting oxidative stress; reducing inflammation; inhibiting infiltration of immune cells into the kidney; preventing or inhibiting an increase in ischemia reperfusion-injury-induced renal ferroportin levels; inhibiting a decrease in H-ferritin levels; inhibiting infiltration of neutrophils and CD11b cells into the kidney; inhibiting splenic iron release; stimulating an increase in H-ferritin levels; and inhibiting an increase in interleukin-6 (IL-6) levels.

The present invention further provides inducers of hepcidin and their use as described herein. In one aspect, hepcidin inducers include, but are not limited to, iron, iron-hepcidin complex, copper-hepcidin complex, metal-hepcidin complex, TMPRSS6 inhibition using antagonists against Tmprss6, plant-derived flavonoids, cytokines (such as IL-6 and IL-22), growth factors such as HGF and EGF, steroid hormones such as estrogen and testosterone, toll-like receptor activation, tyrosine kinase inhibitors such as Sorafenib and mTOR inhibitors such as rapamycin, administration of BMP6, and induction of inflammation. Inducers of inflammation include, for example, erythroferrone (Fam132b) and heparin antagonists.

Other hepcidin inducers include, but are not limited to, agents that inhibit growth factor receptor dependent signaling (AG1296, GTP 14564, AS252424, 10058-F, SU6668, and pterostilbene), decrease inflammation (leflunomide, amlexanox), or impair DNA repair and promote apoptosis (daunorubicin, 9-aminocridine, ethacridine), while the small molecules, vorinostat and SB 204741, inhibit histone deacetylase and serotonin receptor 2B, respectively. Two of the molecules, ipriflavone and vorinostat, have been shown to be active at concentrations that are 10-fold below those required for genistein's effect (Gaun et al., Blood Cells Mol. Diseases, 2014; available online 4 Jul. 2014)

The invention further encompasses the use of synthetic hepcidin derivatives. The invention further encompasses the use of minihepcidins such as PR73 and PR65, as well as alpha-2 macroglobulin modified hepcidin which increases the circulating half-life of hepcidin. These inducers can be used as a combination therapy in conjunction with hepcidin. More than one inducer can be used. One of ordinary skill in the art can determine whether all agents are administered at the same time or if they should be administered at different times.

In one aspect, cytokines of the invention include IL-6 and IL-22. In one aspect of the invention, growth factors include HGF and EGF. In one aspect, steroids of the invention include estrogen and testosterone. In one aspect, antagonists of TMPRSS6 include antagonists such as antisense oligonucleotides and siRNAs against Tmprss6.

In one aspect, hepcidin treatment protects the kidney by degrading ferroportin and causing sequestration of iron. In one aspect, iron is sequestered predominantly in the spleen. In one aspect, the treatment induces reactive oxygen species, apoptosis, and immune cell infiltration in the kidney.

The dosage of hepcidin, or a biologically active fragment or homolog thereof (e.g., SEQ ID NOs:1-5), administered to a subject in need thereof can be determined by one of ordinary skill in the art. For example, in one aspect, it can be from about 0.1 mg/kg body wt. to about 100 mg/kg body weight. In one aspect, it can be from about 1.0 mg/kg body wt. to about 10 mg/kg body wt. Dosages and dosage ranges include intervening integers not specifically recited. For example, 1 to 10 includes 1, 2, 3, 4, 5, 6, 7, 8, 9, and 10, as well as fractions and decimals thereof. Doses include, for example, about 1.0, 1.5, 1.67, 2.0, 2.5, 3.0, 3.33, 4.0, 4.5, 5.0, and 10 mg/kg body wt. Unit doses are also encompassed by the invention, such as from 50 mg to 1,000 mg, for example 50, 55, 60, 65, 70, 75, 100, 125, 150, 175, 200, 225, 250, 275, 300, 325, 350, 400, 450, 500, or 1,000 mg. One of ordinary skill in the art can determine the dosage, number of doses, and timing of doses based on the age, sex, weight, and health of the subject.

In one aspect, a pharmaceutical composition comprising an effective amount of a hepcidin of the invention, or fragments or homologs thereof, is administered at least twice. In another aspect, a pharmaceutical composition is administered at least five times. In yet another aspect, a pharmaceutical composition is administered at least 10 times. One of ordinary skill in the art can determine how often to administer the composition based on the particular disease or disorder being treated or how the subject has responded to prior treatments. One of ordinary skill in the art can also determine when to administer a treatment relative to the time that an IRI event occurs, including before, after, or both.

In one embodiment, the subject is treated with hepcidin prior to the IRI event. In one aspect, the subject can be treated starting at least several days before the event or as close to several minutes before the IRI event. For example, the hepcidin therapy can begin at about 2 hours, 8 hours, 24 hours, or 26 hours prior to IRI. One of ordinary skill in the art will appreciate that hepcidin or biologically active fragments or homologs thereof can be administered at varying times and not just at about 2, 8, 24, or 26 hours prior to IRI. The invention further encompasses treatment following the initiation of IRI. In one aspect, the range of time for treating prior to the IRI event can be from about 1.0 minutes to about 72 hours. In another aspect, the range of time for treating prior to the IRI event can be from about 10 minutes to about 48 hours. In another aspect, the range of time for treating prior to the IRI event can be from about 30 minutes to about 24 hours.

In one embodiment, the subject is treated with hepcidin after the IRI event or both before and after as described above. In one aspect, the subject can be treated starting immediately after such as several minutes after the IRI event. For example, the hepcidin therapy can begin at about 30 minutes, 2 hours, 8 hours, 24 hours, or 48 hours after the IRI. One of ordinary skill in the art will appreciate that hepcidin or biologically active fragments or homologs thereof can be administered at varying times as well.

In one embodiment, 2-glucosamine modified hepcidin can be administered to increase renal selectivity.

The present invention further provides for the use of hepcidin in reducing proteinuria (data not shown). Therefore, the invention provides for the use of hepcidin therapy in treating proteinuric kidney diseases, for example, diabetic nephropathy and glomerulonephritis. In one aspect, treatment reduces proteinuria. In one aspect, treatment prevents or inhibits progression of kidney disease.

Because the methods of the invention are useful for treating ischemic reperfusion injury, the methods further include treating other diseases and disorders associated with ischemic reperfusion injury, including, but not limited to, myocardial IRI and brain IRI.

SUMMARY OF SEQUENCES OF THE INVENTION

The present invention provides for the use of various hepcidin proteins and peptides with the activity described herein as well as biologically active fragments and homologs thereof.

```
SEQ ID NO: 1- Mouse hepcidin 25 (amino acids 59 to
83 of SEQ ID NO: 4) from Peptide International has
the sequence:
DTNFPICIFCCKCCNNSQCGICCKT SEQ ID NO: 2- a 25 a.a. fragment of human hepcidin
SEQ ID NO: 3, and is the equivalent to the murine
25 a.a. peptide SEQ ID NO: 1.
DTHFPICIFCCGCCHRSKCGMCCKT SEQ ID NO: 3- Human hepcidin is an 84 amino acid
residue peptide. Its GenBank accession number is
AAH20612.1.
MALSSQIWAACLLLLLLLASLTSGSVFPQQTGQLAELQPQDRAGARASWM

PMFQRRRRRDTHFPICIFCCGCCHRSKCGMCCKT

SEQ ID NO: 4- Mouse hepcidin is an 83 amino acid
residue peptide. Its GenBank accession number is
NP_115930.1.
MALSTRTQAACLLLLLLASLSSTTYLHQQMRQTTELQPLHGEESRADIAI

PMQKRRKRDTNFPICIFCCKCCNNSQCGICCKT

SEQ ID NO: 5- Rat hepcidin precursor is an 84
amino acid residue peptide. Its GenBank accession
number is NP_445921.1
MALSTRIQAACLLLLLLASLSSGAYLRQQTRQTTALQPWHGAESKTDDSA

LLMLKRRKRDTNFPICLFCCKCCKNSSCGLCCIT
```

In one aspect, the invention uses a biologically active hepcidin protein or peptide. Preferably, the isolated polypeptide comprises a mammalian molecule at least about 30% homologous to a polypeptide having the amino acid sequence of at least one of SEQ ID NO:1, SEQ ID NO:2, SEQ ID NO:3, SEQ ID NO:4, and SEQ ID NO:5. Preferably, the isolated polypeptide is at least about 35% homologous, more preferably, about 40% homologous, more preferably, about 45% homologous, even more preferably, about 50% homologous, more preferably, about 55% homologous, preferably, about 60% homologous, more preferably, about 65% homologous, even more preferably, more preferably, about 70% homologous, more preferably, about 75% homologous, even more preferably, about 80% homologous, more preferably, about 85% homologous, more preferably, about 90% homologous, even more preferably, about 95% homologous, more preferably, about 96% homologous, more preferably, about 97% homologous, more preferably, about 98% homologous, and most preferably, about 99% homologous to at least one of SEQ ID NOs:1-5.

The present invention further encompasses modification of the hepcidin proteins and peptides, including amino acid deletions, additions, and substitutions, as well as modifications to increase in vivo half-life and decrease degradation in vivo.

The present invention includes an isolated nucleic acid comprising a nucleic acid sequence encoding a mammalian hepcidin protein, or a fragment or homolog thereof. In one aspect, the sequence encodes a peptide comprising a sequence having SEQ ID NOs:1, 2, 3, 4, or 5, or a biologically active fragment of homolog thereof.

Synthetic hepcidins are encompassed by the invention and derivatives include minihepcidin.

The present invention further provides kits for treating subjects as described herein, comprising a hepcidin protein or peptide, an applicator, and an instructional material for the use thereof. Kits can be provided with unit doses in a container or syringe or amounts of hepcidins that one of ordinary skill in the art can administer based on a dose per weight, etc.

Various aspects and embodiments of the invention are described in further detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5, comprising FIGS 5a to 5d. Hepcidin prevents IRI induced upregulation of Ferroportin and loss of H Ferritin. Expression of ferroportin (a) in the kidney membrane fraction and H-ferritin (c) in the whole kidney lysates was measured by quantitative Western Blots (a and c). In case of ferroportin blots equal protein loading was confirmed and normalized using Ponceau staining, whereas GAPDH was used to confirm equal loading and normalize H ferritin. Hepcidin prevented the IRI induced upregulation of (a) Ferroportin, and (c) Loss of H ferritin in the kidney. Representative blots from 3 independent experiments are shown. FIGS. b and d: Quantitation of Ferroportin and H ferritin in the kidneys of Sham (□), IRI (○) and Hepcidin+IRI (▽) mice respectively was carried out using densitometry software and is expressed as mean±SEM. *P<0.05, **P<0.01.

Figure 10A:
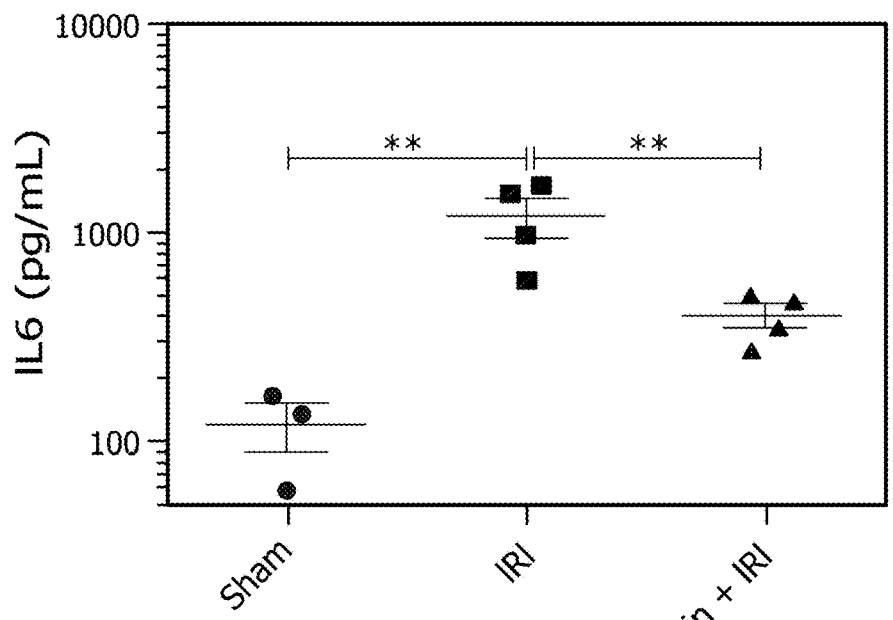
FIG. 10, comprising FIGS. 10a to 10c. Hepcidin reduces IRI induced serum IL6 accumulation. Serum IL6 levels were measured by ELISA. Hepcidin administration significantly reduced IRI induced serum IL6 in both WT and HAMP$^{-/-}$ mice. In WT mice, IRI resulted in a significant increase in IL6 compared to sham mice, which was prevented by Hepcidin (a). Similarly, Hepcidin treated HAMP$^{-/-}$-IRI mice had significantly reduced serum IL6 compared to untreated HAMP$^{-/-}$-IRI mice and were not significant compared to sham. Sham (●), IRI (■) and Hepcidin-IRI (▲). n=3-5 *P<0.05, **P<0.007.
Figure 10B:
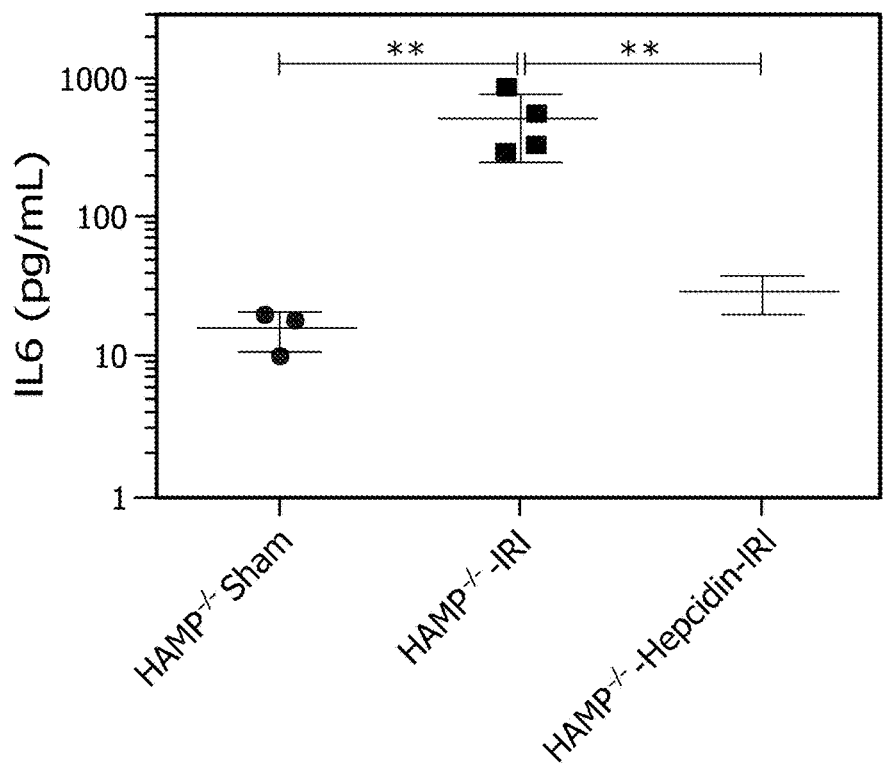
Figure 10C:
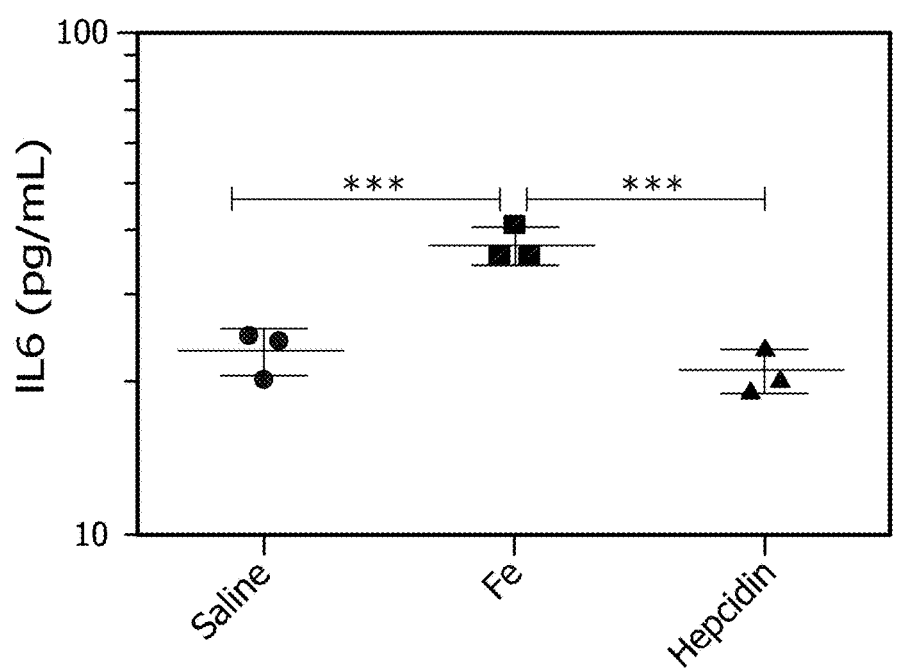

We treated splenocytes from WT mice with ferrous sulfate and measured the IL-6 secretion into supernatants by ELISA. Untreated splenocytes and hepcidin-treated splenocytes were used as controls. There was no significant difference in IL-6 levels between the untreated splenocytes and hepcidin-treated celss (FIG. 10c). However treatment with iron significantly increased splenocytes IL-6 secretion compared to both untreated and hepcidin-treated cells (FIG 10c, p<0.005).

Figure 11:
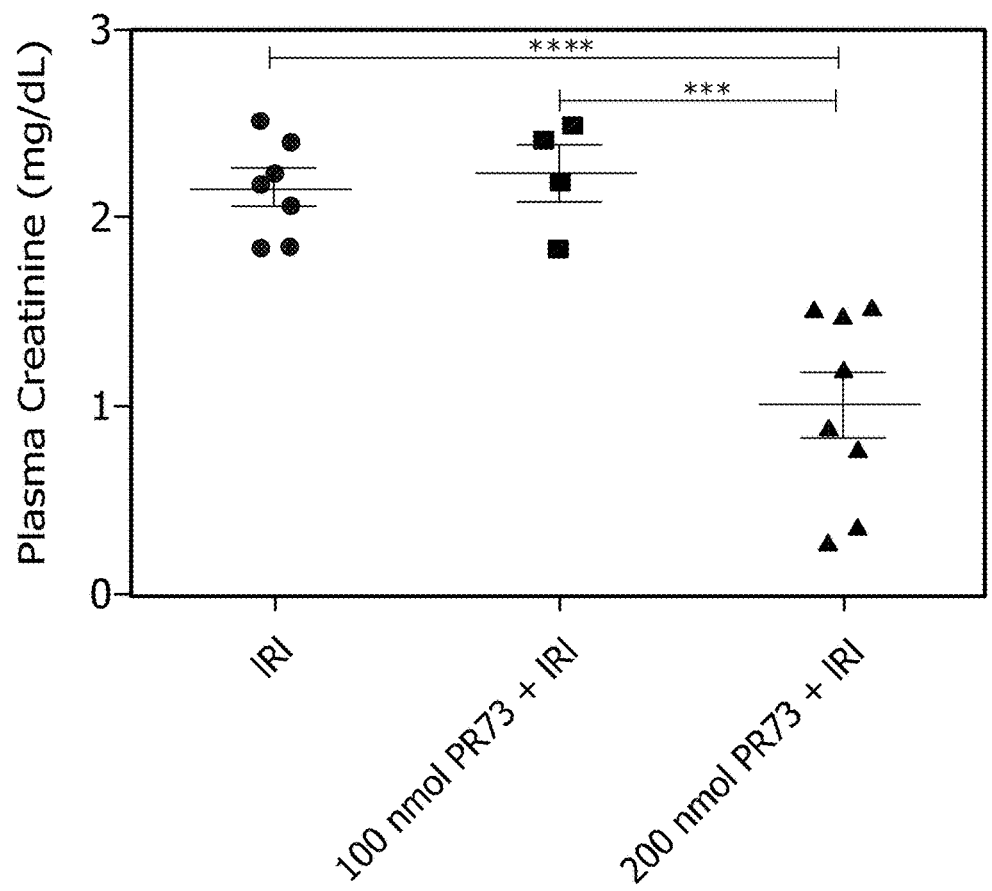

FIG. 11. Pooled minihepcidin (PR-73) data showing protection in AKI. Animals were subjected to IRI with or without treatment with the hepcidin agonist at 100 or 200 nmol. The effects at 200 nmol are statistically significant relative to the other groups.

FIG. 12, comprising FIGS. 12a to 12d (also referred to as Supporting FIG. 1). Representative morphology (by H&E staining) of kidneys after sham operation (a), IRI (b), and hepcidin-IRI (c). Magnification: 10× (a, b, c), Original magnification 20× (insets). Relative NGAL expression in the kidneys of Sham ( ) IRI (○) and Hepcidin-IRI (▽) normalized to GAPDH (d). Data are represented as mean±SEM. *P<0.001, **P<0.0001 (n=4-5 per group).

FIG. 13, comprising FIGS. 13a to 13b (also referred to as Supporting FIG. 2). High magnification images of 4HNE staining. Untreated WT IRI mice showed strong reactivity to 4HNE (a), which was markedly reduced in the Hepcidin treated WT-IRI mice (b). Representative images from two different experiments with 4-5 mice each are depicted. Magnification 20×.

Figures 14A, 14B, 14C:
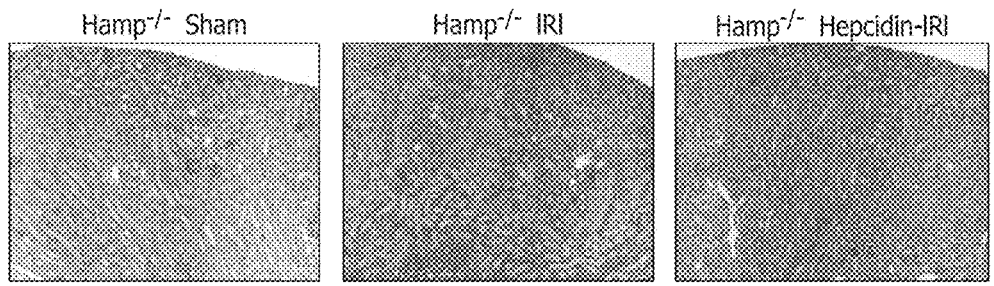
Figure 14D:
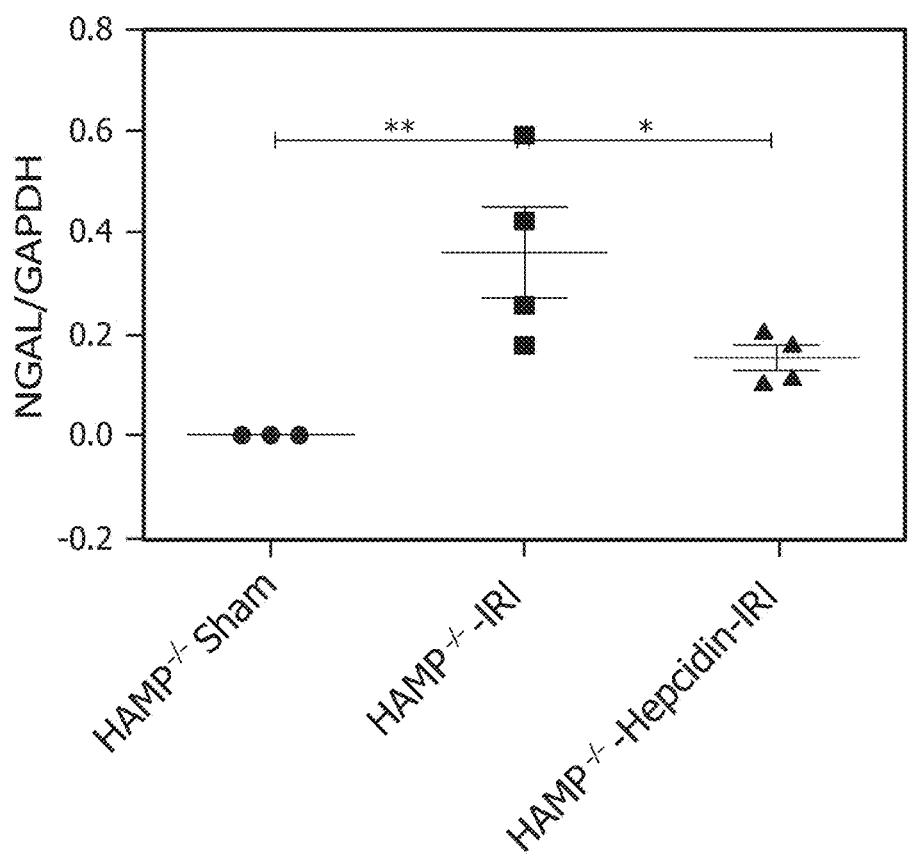

FIG. 14, comprising FIGS. 14a to 14d (also referred to as Supporting FIG. 3) Representative morphology of HAMP$^{-/-}$ kidneys (by H&E staining) 24 hours after sham operation (a), IRI (b) and hepcidin treatment IRI (c) shows Hepcidin mediated protection of the kidney after IRI. Magnification: 10×. Relative NGAL expression in the kidneys of HAMP$^{-/-}$ Sham (●), HAMP$^{-/-}$-IRI (■) and HAMP$^{-/-}$-Hepcidin-IRI (▲), normalized to GAPDH (d). Data are represented as mean±SEM. *P<0.05, **P<0.005 (n=3-4 per group).

Figures 15A, 15B, 15C:
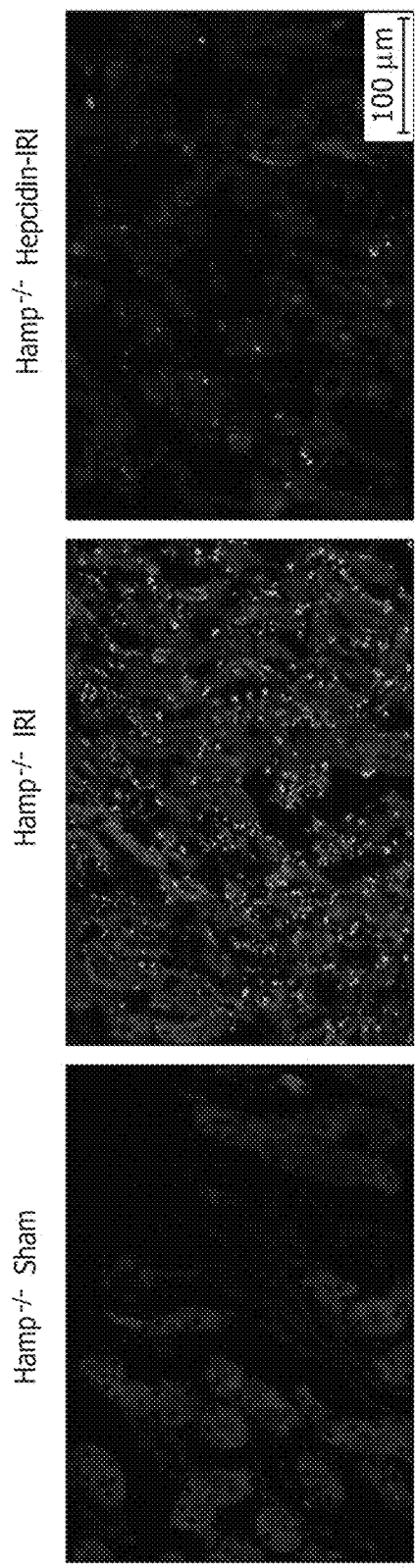

FIG. 15, comprising FIGS. 15a to 15c (also referred to as Supporting FIG. 4). High magnification images of TUNEL staining. Sham operated HAMP$^{-/-}$ mice did not show signs of apoptosis (a). Untreated HAMP$^{-/-}$-IRI mice showed severe apoptosis in the cells of the corticomedullar region (b), which was markedly reduced in the Hepcidin treated HAMP$^{-/-}$-IRI mice (c). Representative images from two different experiments with 4-5 mice each are depicted. Magnification 20×, Scale bar: 100 Ξm.

DETAILED DESCRIPTION

Abbreviation and Acronyms

4-HNE—4 hydroxynonenal
a.a.—amino acid
AI—anemia of inflammation
AKI—acute kidney injury
ASO—antisense oligonucleotide
ATN—acute tubular necrosis
BMP—bone morphogenetic protein
EGF—epidermal growth factor
FAC—ferric ammonium chloride
FCS—fetal calf serum
H&E—hematoxylin and eosin
HAMP—hepcidin
HGF—hepatocyte growth factor
HJV—hemojuvelin
IL-6—interleukin-6
IRI—ischemia reperfusion injury
kg—kilogram
mg—milligram
OH—hydroxyl
PG-APS—streptococcal peptidoglycan-polysaccharide
PLP—paraformaldehyde/lysine/periodate
ROS—reactive oxygen species
sHJV.Fc—Soluble HJV-Fc fusion protein
SOD—superoxide dismutase
TEC—tubular epithelial cell
TfR1—transferrin receptor 1
TfR2—transferrin receptor 2
TMPRSS6—transmembrane serine protease, also known as matriptase-2
TUNEL—terminal deoxynucleotidyl transferase-mediated digoxigenin-deoxyuridine nick-end labeling
wt.—weight
WT—wild type

DEFINITIONS

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

As used herein, the term "aerosol" refers to suspension in the air. In particular, aerosol refers to the particlization or atomization of a formulation of the invention and its suspension in the air.

As used herein, an "agonist" is a composition of matter which, when administered to a mammal such as a human, enhances or extends a biological activity attributable to the level or presence of a target compound or molecule of interest in the mammal.

The term "alterations in peptide structure" as used herein refers to changes including, but not limited to, changes in sequence, and post-translational modification.

An "antagonist" is a composition of matter which when administered to a mammal such as a human, inhibits a biological activity attributable to the level or presence of a compound or molecule of interest in the mammal.

As used herein, "alleviating a disease or disorder symptom," means reducing the severity of the symptom or the frequency with which such a symptom is experienced by a patient, or both.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

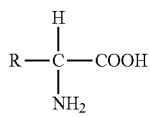

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

The term "an effective amount of hepcidin" as used herein refers to the use of a full-length hepcidin or a biologically active fragment or homolog thereof that is effective for the use described herein.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

The term "antibody" refers to polyclonal and monoclonal antibodies and derivatives thereof (including chimeric, synthesized, humanized and human antibodies), including an entire immunoglobulin or antibody or any functional fragment of an immunoglobulin molecule which binds to the target antigen and or combinations thereof. Examples of such functional entities include complete antibody molecules, antibody fragments, such as $F_v$, single chain $F_v$, complementarity determining regions (CDRs), $V_L$ (light chain variable region), $V_H$ (heavy chain variable region), Fab, F(ab')$_2$ and any combination of those or any other functional portion of an immunoglobulin peptide capable of binding to target antigen.

Antibodies exist, e.g., as intact immunoglobulins or as a number of well characterized fragments produced by digestion with various peptidases. Thus, for example, pepsin digests an antibody below the disulfide linkages in the hinge region to produce F(ab')$_2$ a dimer of Fab which itself is a light chain joined to $V_H$-$C_{H1}$ by a disulfide bond. The F(ab')$_2$ may be reduced under mild conditions to break the disulfide linkage in the hinge region, thereby converting the F(ab')$_2$ dimer into an Fab$_1$ monomer. The Fab$_1$ monomer is essentially an Fab with part of the hinge region (see, FUNDAMENTAL IMMUNOLOGY, 3RD ED., W. E. Paul, ed., Raven Press, N.Y. (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

The term "single chain antibody" refers to an antibody wherein the genetic information encoding the functional fragments of the antibody are located in a single contiguous length of DNA. For a thorough description of single chain antibodies, see Bire, et al., Science 242:423 (1988) and Huston, et al., Proc. Nat'l Acad. Sci. USA 85:5879 (1988).

The term "humanized" refers to an antibody wherein the constant regions have at least about 80% or greater homology to human immunoglobulin. Additionally, some of the nonhuman, such as murine, variable region amino acid residues can be modified to contain amino acid residues of human origin.

Humanized antibodies have been referred to as "reshaped" antibodies. Manipulation of the complementarity-determining regions (CDR) is a way of achieving humanized antibodies. See, for example, Jones, et al., Nature 321:522 (1988) and Riechmann, et al., Nature 332:323 (1988), both of which are incorporated by reference herein.

For a review article concerning humanized antibodies, see Winter & Milstein, Nature 349:293 (1991), incorporated by reference herein.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a subject, including, but not limited to, sputum, mucus, phlegm, tissues, biopsies, cerebrospinal fluid, blood, serum, plasma, other blood components, gastric aspirates, throat swabs, pleural effusion, peritoneal fluid, follicular fluid, ascites, skin, hair, tissue, blood, plasma, cells, saliva, sweat, tears, semen, stools, Pap smears, and urine. One of skill in the art will understand the type of sample needed.

A "biomarker" or "marker" is a specific biochemical in the body which has a particular molecular feature that makes it useful for measuring the progress of disease or the effects of treatment, or for measuring a process of interest.

The term "cancer", as used herein, is defined as proliferation of cells whose unique trait (loss of normal controls) results in unregulated growth, lack of differentiation, local tissue invasion, and metastasis. Examples include but are not limited to, melanoma, breast cancer, prostate cancer, ovarian cancer, uterine cancer, cervical cancer, skin cancer, pancreatic cancer, colorectal cancer, renal cancer and lung cancer.

As used herein, the term "carrier molecule" refers to any molecule that is chemically conjugated to a molecule of interest.

The term "cell surface protein" means a protein found where at least part of the protein is exposed at the outer aspect of the cell membrane. Examples include growth factor receptors.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above.

A "computer-readable medium" is an information storage medium that can be accessed by a computer using a commercially available or custom-made interface. Exemplary compute-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

As used herein, the term "conservative amino acid substitution" is defined herein as an amino acid exchange within one of the following five groups:
I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

As used herein, a "derivative" of a compound refers to a chemical compound that may be produced from another compound of similar structure in one or more steps, as in replacement of H by an alkyl, acyl, or amino group.

As used herein "detachment-induced chemoresistance" refers to the change in cancer cells that occurs when they become resistant to chemotherapy following a change in their interactions with the extracellular matrix.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, in one embodiment, the term "diagnosis" refers to detecting aberrant ALCAM expression due to cancers expressing ALCAM. In any method of diagnosis exist false positives and false negatives. Any one method of diagnosis does not provide 100% accuracy.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, the term "effector domain" refers to a domain capable of directly interacting with an effector molecule, chemical, or structure in the cytoplasm which is capable of regulating a biochemical pathway.

The term "elixir," as used herein, refers in general to a clear, sweetened, alcohol-containing, usually hydroalcoholic liquid containing flavoring substances and sometimes active medicinal agents.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means. Compounds or agents of the invention can be administered to a subject by these means when appropriate.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

The term "nasal administration" in all its grammatical forms refers to administration of at least one compound of the invention through the nasal mucous membrane to the bloodstream for systemic delivery of at least one compound of the invention. The advantages of nasal administration for delivery are that it does not require injection using a syringe and needle, it avoids necrosis that can accompany intramuscular administration of drugs, and trans-mucosal administration of a drug is highly amenable to self-administration.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides or to peptides shorter than the full length native or mature protein.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

By "presensitization" is meant pre-administration of at least one innate immune system stimulator prior to challenge with an agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "prophylactic" treatment is a treatment administered to a subject who does not exhibit signs of a disease or exhibits only early signs of the disease for the purpose of decreasing the risk of developing pathology associated with the disease.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. A "significant detectable level" is an amount of contaminate that would be visible in the presented data and would need to be addressed/explained during analysis of the forensic evidence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "receptor" is a compound that specifically binds to a ligand.

A "ligand" is a compound that specifically binds to a target receptor.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, *Methods for General and Molecular Bacteriology*, American Society for Microbiology, Washington, D.C., p. 574).

A "sample," as used herein, refers preferably to a biological sample from a subject for which an assay or other use is needed, including, but not limited to, normal tissue samples, diseased tissue samples, sputum, mucus, phlegm, biopsies, cerebrospinal fluid, blood, serum, plasma, other blood components, gastric aspirates, throat swabs, pleural effusion, peritoneal fluid, follicular fluid, ascites, skin, hair, tissue, blood, plasma, cells, saliva, sweat, tears, semen, stools, Pap smears, and urine. A sample can also be any other source of material obtained from a subject which contains cells, tissues, or fluid of interest. A sample can also be obtained from cell or tissue culture.

As used herein, the term "secondary antibody" refers to an antibody that binds to the constant region of another antibody (the primary antibody).

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M NaPO$_4$, 1 mM EDTA at 50° C. with washing in 2× standard saline citrate (SSC), 0.1% SDS at 50° C.; preferably in 7% (SDS), 0.5 M NaPO$_4$, 1 mM EDTA at 50° C. with washing in 1×SSC, 0.1% SDS at 50° C.; preferably 7% SDS, 0.5 M NaPO$_4$, 1 mM EDTA at 50° C. with washing in 0.5×SSC, 0.1% SDS at 50° C.; and more preferably in 7% SDS, 0.5 M NaPO$_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

The term to "treat," as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease.

A "variant", as described herein, refers to a segment of DNA that differs from the reference DNA. A "marker" or a "polymorphic marker", as defined herein, is a variant. Alleles that differ from the reference are referred to as "variant" alleles.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

In one embodiment, a hepcidin can be used for treatment of inflammatory conditions. In one aspect, it is useful for preventing or treating renal ischemia reperfusion injury. In one aspect, it is useful for preventing or treating acute kidney injury.

One of ordinary skill in the art will appreciate that the sequences of the components of the hepcidin protein can be modified independently of one another with conservative amino acid changes, including, insertions, deletions, and substitutions, and that the valency could be altered as well, as long as the resulting multimer/multimeric complex remains effective. Amino acid changes (fragments and homologs) can be made independently in each hepcidin as well when they are being used in combination therapy.

In one aspect, a protein or peptide of the invention, or a combination thereof, can be administered by a route selected from, including, but not limited to, intravenously, intrathecally, locally, intramuscularly, topically, orally, intra-arterially, parenterally, etc. Administration can be more than once. One of ordinary skill in the art can determine how often to administer the compound, the dose to be used, and what combination of other agents it can be administered with such as therapeutic agents and/or other drugs or compounds such as antimicrobial agents, anti-inflammatory agents, etc. One of ordinary skill in the will be able to determine when or if to use an additional agent and the route of administration.

The peptides of the present invention may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Ill.; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions that will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the BOC method that utilized tert-butyloxcarbonyl as the α-amino protecting group, and the FMOC method which utilizes 9-fluorenylmethyloxycarbonyl to protect the α-amino of the amino acid residues, both methods of which are well-known by those of skill in the art.

To ensure that the proteins or peptides obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide can be purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure peptide obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

Peptide Modification and Preparation

Peptide preparation is described in the Examples. It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for analogs of proteins. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on peptide function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the invention are not limited to products of any of the specific exemplary processes listed herein.

The invention includes the use of beta-alanine (also referred to as β-alanine, β-Ala, bA, and βA, having the structure:

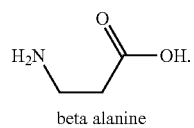
beta alanine

Sequences are provided herein which use the symbol "βA", but in the Sequence Listing submitted herewith "βA" is provided as "Xaa" and reference in the text of the Sequence Listing indicates that Xaa is beta alanine.

Peptides useful in the present invention, such as standards, or modifications for analysis, may be readily prepared by standard, well-established techniques, such as solid-phase peptide synthesis (SPPS) as described by Stewart et al. in *Solid Phase Peptide Synthesis*, 2nd Edition, 1984, Pierce Chemical Company, Rockford, Ill.; and as described by Bodanszky and Bodanszky in *The Practice of Peptide Synthesis*, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the BOC method which utilized tert-butyloxycarbonyl as the α-amino protecting group, and the FMOC method which utilizes 9-fluorenylmethyloxcarbonyl to protect the α-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dichloromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide may be purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high performance liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide.

For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, Guide to Protein Purification, Harcourt Brace Jovanovich, San Diego).

As discussed, modifications or optimizations of peptide ligands of the invention are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

Amino Acid Substitutions

In certain embodiments, the disclosed methods and compositions may involve preparing peptides with one or more substituted amino acid residues.

In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art. For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

Pharmaceutical Compositions and Administration

The invention is also directed to methods of administering the compounds of the invention to a subject.

Pharmaceutical compositions comprising the present compounds are administered to a subject in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

In accordance with one embodiment, a method of treating a subject in need of such treatment is provided. The method comprises administering a pharmaceutical composition comprising at least one compound of the present invention to a subject in need thereof. Compounds identified by the methods of the invention can be administered with known compounds or other medications as well.

The pharmaceutical compositions useful for practicing the invention may be administered to deliver a dose of between 1 ng/kg/day and 100 mg/kg/day.

The invention encompasses the preparation and use of pharmaceutical compositions comprising a compound useful for treatment of the diseases and disorders disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The compositions of the present invention may comprise at least one active peptide, one or more acceptable carriers, and optionally other peptides or therapeutic agents.

For in vivo applications, the peptides of the present invention may comprise a pharmaceutically acceptable salt. Suitable acids which are capable of forming such salts with the compounds of the present invention include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, anthranilic acid, cinnamic acid, naphthalene sulfonic acid, sulfanilic acid and the like.

Pharmaceutically acceptable carriers include physiologically tolerable or acceptable diluents, excipients, solvents or adjuvants. The compositions are preferably sterile and non-pyrogenic. Examples of suitable carriers include, but are not limited to, water, normal saline, dextrose, mannitol, lactose or other sugars, lecithin, albumin, sodium glutamate, cysteine hydrochloride, ethanol, polyols (propylene glycol, polyethylene glycol, glycerol, and the like), vegetable oils (such as olive oil), injectable organic esters such as ethyl oleate, ethoxylated isosteraryl alcohols, polyoxyethylene sorbitol and sorbitan esters, microcrystalline cellulose, aluminum methahydroxide, bentonite, kaolin, agar-agar and tragacanth, or mixtures of these substances, and the like.

The pharmaceutical compositions may also contain minor amounts of nontoxic auxiliary pharmaceutical substances or excipients and/or additives, such as wetting agents, emulsifying agents, pH buffering agents, antibacterial and antifungal agents (such as parabens, chlorobutanol, phenol, sorbic acid, and the like). Suitable additives include, but are not limited to, physiologically biocompatible buffers (e.g., tromethamine hydrochloride), additions (e.g., 0.01 to 10 mole percent) of chelants (such as, for example, DTPA or DTPA-bisamide) or calcium chelate complexes (as for example calcium DTPA or CaNaDTPA-bisamide), or, optionally, additions (e.g. 1 to 50 mole percent) of calcium or sodium salts (for example, calcium chloride, calcium ascorbate, calcium gluconate or calcium lactate). If desired, absorption enhancing or delaying agents (such as liposomes, aluminum monostearate, or gelatin) may be used. The compositions can be prepared in conventional forms, either as liquid solutions or suspensions, solid forms suitable for solution or suspension in liquid prior to injection, or as emulsions. Pharmaceutical compositions according to the present invention can be prepared in a manner fully within the skill of the art.

The peptides of the invention, pharmaceutically acceptable salts thereof, or pharmaceutical compositions comprising these compounds may be administered so that the compounds may have a physiological effect. Administration may occur enterally or parenterally; for example orally, rectally, intracisternally, intravaginally, intraperitoneally, locally (e.g., with powders, ointments or drops), or as a buccal or nasal spray or aerosol. Parenteral administration is preferred. Particularly preferred parenteral administration methods include intravascular administration (e.g. intravenous bolus injection, intravenous infusion, intra-arterial bolus injection, intra-arterial infusion and catheter instillation into the vasculature), peri- and intra-target tissue injection (e.g. peri-tumoral and intra-tumoral injection), subcutaneous injection or deposition including subcutaneous infusion (such as by osmotic pumps), intramuscular injection, and direct application to the target area, for example by a catheter or other placement device.

Where the administration of the peptide is by injection or direct application, the injection or direct application may be in a single dose or in multiple doses. Where the administration of the compound is by infusion, the infusion may be a single sustained dose over a prolonged period of time or multiple infusions.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically, dosages of the compound of the invention which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. In one aspect, the dosage of the compound will vary from about 1 mg to about 10 g per kilogram of body weight of the animal. In another aspect, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type of cancer being diagnosed, the type and severity of the condition or disease being treated, the type and age of the animal, etc.

Suitable preparations include injectables, either as liquid solutions or suspensions, however, solid forms suitable for solution in, suspension in, liquid prior to injection, may also be prepared. The preparation may also be emulsified, or the polypeptides encapsulated in liposomes. The active ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants.

The invention also includes a kit comprising the composition of the invention and an instructional material which describes adventitially administering the composition to a cell or a tissue of a subject. In another embodiment, this kit comprises a (preferably sterile) solvent suitable for dissolving or suspending the composition of the invention prior to administering the compound to the subject.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of using the compositions for diagnostic or identification purposes or of alleviation the diseases or disorders in a cell or a tissue of a mammal. The instructional material of the kit of the invention may, for example, be affixed to a container which contains the multimeric peptide of the invention or be shipped together with a container which contains the peptide. Alternatively, the instructional material may be shipped separately from the container with the intention that the instructional material and the compound be used cooperatively by the recipient.

Therapeutic Agents

In other embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes or other agents may be used as adjunct therapies when using the multimeric peptide ligand complexes described herein. Drugs useful in the invention may, for example, possess a pharmaceutical property selected from the group consisting of antimitotic, antikinase, alkylating, antimetabolite, antibiotic, alkaloid, anti-angiogenic, pro-apoptotic agents, and combinations thereof.

Techniques for detecting and measuring these agents are provided in the art or described herein.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

According to some aspects of the present invention, the method includes providing to the subject a therapeutic compound in combination with a pharmaceutically acceptable carrier.

The present invention further encompasses kits.

Compositions of the present invention may be presented in a pack or dispenser device, such as an FDA approved kit, which may contain one or more unit dosage forms containing the therapeutic compound as described herein.

In some embodiments, the kit may include a therapeutic compound (as described herein), metal or plastic foil, such as a blister pack, a dispenser device or an applicator, tubes, buffers, and instructions for administration. The various reagent components of the kits may be present in separate containers, or some or all of them may be pre-combined into a reagent mixture in a single container, as desired. The dispenser device or applicator may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Other embodiments of the invention will be apparent to those skilled in the art based on the disclosure and embodiments of the invention described herein. It is intended that the specification and examples be considered as exemplary only, with a true scope and spirit of the invention being indicated by the following claims. While some representative experiments have been performed in test animals, similar results are expected in humans. The exact parameters to be used for injections in humans can be easily determined by a person skilled in the art.

Other techniques known in the art may be used in the practice of the present invention.

The invention is now described with reference to the following Examples. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

EXAMPLES

Methods

Mice and Surgical Protocol

All experiments were performed in accordance with the National Institutes of Health and Institutional Animal Care and Use Guidelines. The Animal Care and Use Committee of the University of Virginia approved all procedures and protocols. C57BL/6 mice from the Jackson Laboratory and hepcidin knockout mice (HAMP−/−), a kind gift from Dr Cindy Roy (John Hopkins University) were used in this study. All experiments were performed on 8-10 weeks old male mice. Kidney ischemia-reperfusion surgery was performed as previously reported (44). The core temperature of the mice was maintained between 34° C. and 36° C. using a heating pad. After anesthetizing the mice (ketamine, 12 mg/ml; atropine, 0.48 mg/ml; xylazine, 24 mg/ml; 200 ml mixture administered per 20 g body weight), bilateral flank incisions were made, both renal pedicles were exposed, and cross-clamped for 26 minutes (severe I/R injury) or 24 minutes (mild I/R injury). After the determined ischemia, clamps were removed, and kidneys were allowed to reperfuse for 24 hours. Ambient postoperative air temperature was maintained between 30° C. and 32° C. until mice had fully recovered. Sham-operated animals underwent bilateral flank incisions without clamping of renal pedicles. Twenty-four hours later, mice were euthanized, and tissues were harvested.

Experimental Design

Figure 2A:
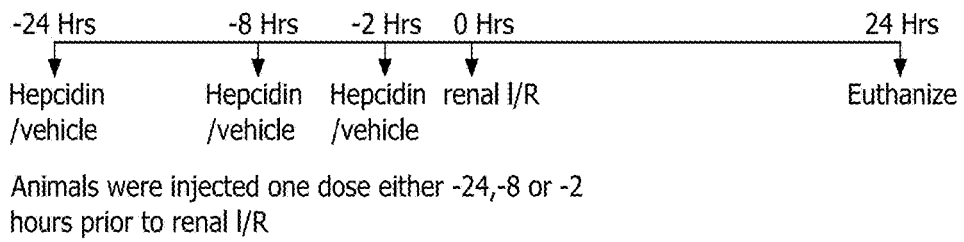
FIG. 2, comprising FIGS. 2a to 2e. Hepcidin pretreatment mitigates kidney injury following renal IRI. Experimental design and time course of treatment (a). Plasma creatinine (b) was measured 24 hours after IRI in untreated (○) or hepcidin injected (50 μg injected 2 hrs: ■, 8 hrs: Δ, 24 hrs: ▽, or ◇ [100 μg] mice and compared to sham operated mice (□). Data are represented as mean±SEM. *P<0.05, *P<0.001, **P<0.0001 (n=4-5 per group). Representative morphology (by H&E staining) of kidneys after sham operation (c), IRI (d) and hepcidin-IRI (e). Magnification: 10×.

Animals were divided into three groups, injected intraperitoneally with water and underwent IRI (IRI), injected intraperitoneally with 50-100 µg hepcidin at different time points prior to IRI (Hepcidin-IRI) or were sham operated (Sham). The experimental design is depicted in FIG. 2a.

Blood and Tissue Samples

Before euthanasia, animals were anesthetized and blood was drawn from the axilla, following which tissues were harvested. All the tissue slices were fixed with 10% neutral-buffered formalin for paraffin embedding, and with periodate-lysine-paraformaldehyde fixative to be frozen in optimal cutting temperature compound, or snap frozen in liquid nitrogen for subsequent mRNA extraction.

Renal Function

Renal function was determined by measurement of plasma creatinine, determined using a modified Jaffe colorimetric assay (44).

Histologic Examination and Stereologic Analysis of Tissue Morphology

Kidneys were fixed in buffered formalin for 48 h, embedded in paraffin, sectioned (3-µm thickness), and stained with hematoxylin and eosin (H&E). The extent of acute tubular necrosis (ATN) following IRI was assessed using H&E stained kidney sections. An investigator blinded to the sample identities was used for these analyses to have an unbiased approach. The percentage of tubules in the corticomedullary junction that displayed acute tubular necrosis was identified according to the presence of cast formation, tubule dilation, and/or tubular epithelial de-nucleation.

Serum Iron, Hepcidin and IL-6 Measurement

Serum iron (Abeam), hepcidin (Intrinsic Lifescience) and IL-6 levels (eBioscience) were measured using commercial ELISA kits, as per manufacturers instructions.

Non-Heme Iron Assay

Non-heme iron content in tissue was measured using the method described in published literature with slight modifications (60). Briefly, tissues were accurately weighed, finely cut and placed for 20 hours at 65° C. in a solution of 3M HCl/0.61 M trichloroacetic acid. After cooling to room temperature, the acid extract was spun at 12,000 rpm to collect the supernatant. 0.1 mL of the supernatant was incubated with chromogen solution (1.86 mM bathophenanthroline sulfonate/143 mM thioglycollic acid) for 20 minutes, and OD was measured at 535 nm. A standard curve was generated using an iron standard solution (Ricca Iron AA standard) against water as the blank. Non-heme iron content (µg/g) was calculated using the equation described (60).

Flow Cytometry.

Single-cell suspensions from the kidney were prepared using standard methods. Briefly, kidney section was cut into small pieces and collagenase (type 2) digested for 20 minutes at 37° C. The digested kidney was then serially passed through a 100 micron and 50 micron sieve to collect the cell suspension. The cells were then incubated with anti-CD16/32 (Fc block, clone 93; eBioscience, San Diego, Calif.) and stained with APC-eFlour 780-conjugated anti-CD45 (30-F11), PE conjugated anti-CD11b (M1/70), APC conjugated anti Ly6G (RB6-8C5) and eFlour 450 conjugated anti Ly6C (HK1.4). Flow cytometry data were acquired using BD FACSCalibur (BD Biosciences, San Jose, Calif.) with Cytek eight-color flow cytometry upgrade (Cytek Development, Fremont, Calif.) and analyzed with FlowJo software 9.0 (Tree Star Inc., Ashland, Oreg.). 100-200,000 events/samples were acquired. Neutrophils were identified as CD11b-Ly6G-Ly6C positive cells within CD45 gate.

TUNEL Assay

Apoptotic cells in the kidney were detected by TUNEL assay following the manufacturer's protocol (Roche Diagnostics, Mannheim, Germany). Briefly, PLP-fixed kidney sections were immersed in 3% hydrogen peroxide-methanol (10 minutes) and permeabilized with cold 0.1% Triton-X100 and 0.1% sodium acetate (2 minutes). DNA fragments in apoptotic cells were then labeled and identified by terminal transferase dUTP conjugated to fluorescein (Roche Diagnostics) for 60 minutes at room temperature in dark. The apoptotic cells were imaged using a Zeiss Axiovert 200 microscope with Apo Tome (Zeiss).

Immunohistochemistry.

Kidney sections were embedded in paraffin, 3 µm sectioned, and stained for 4 Hydroxynonenal (4-HNE) using standard protocols. Briefly sections were deparaffanized in xylenes, rehydrated in a series of ethanol rinses from 100% to 70% ethanol, then washed in distilled water. Sections were then incubated in 3% H2O2 in methanol for 20 minutes. After treating with Avidin and Biotin for 15 minutes each (Vector) the sections were blocked in blocking buffer containing 10% donkey serum in sodium phosphate buffer (NaPO4 buffer), at room temperature for 30 minutes. 4-HNE antibody was diluted in 1% BSA in NaPO4 buffer (Abeam; 1:1000) and added to sections overnight at 4° C. Sections were washed 3 times with NaPO4 buffer for 5 minutes each and incubated with biotinylated donkey anti-goat secondary antibody (Vector) for 1 hour. Sections were washed 3 times in NaPO4 buffer, and then incubated in ABC ready-to-use reagent (Vector Labs) for 30 minutes. After another 3 washes with NaPO4 buffer the sections exposed to diaminobenzidine (DAB) for 5 minutes followed by washing with in distilled water. The sections were counter-stained with 1% methylene blue solution, washed in water and dehydrated with xylene. Sections were imaged by using a Zeiss Axio Imager Z2/Apotome Microscope fitted with motorized focus drives and motorized XYZ microscope stage and integrated to a workstation running StereoInvestigator software, version 10.51 (MBF Bioscience, Williston, Vt.)

Immunofluorescence

Three micron paraformaldehyde/lysine/periodate (PLP) fixed kidney sections were used for the immunofluorescence detection of neutrophils and CD11b cells. Briefly, the kidney sections were air dried, and treated with 0.3% triton X in 10% horse serum for 30 minutes. After washing the sections with PBS, anti CD16/32 antibody was added to block the FC receptors. This was followed by incubation with FITC-labeled anti-neutrophil antibody (7/4, Cederline, 1 in 30) and PE-labeled CD11b (M1/70, ebioscience, 1 in 30) diluted in 10% horse serum for 1.5 hours. The sections were then washed 3 times in PBS and mounted with ProLong Gold anti fade agent with DAPI (Life Technologies). Sections were imaged by Zeiss Axiovert 200 microscope with Apo Tome (Zeiss)

Cell Culture

A mouse proximal tubule cell line (TKPTS cells, kindly provided by Dr. E. Bello-Reuss, University of Texas Medical Branch, Galveston, Tex.) was used in these studies. The cells were cultured in advanced DMEM/F12 medium supplemented with glutamine, 7.5% FBS and antibiotics. Cells were grown to 80% confluence and maintained at 37° C. in 5% $CO_2$. All experiments were performed in serum free DMEM/F12 medium for a maximum of 24 hours.

In-Vitro Hypoxia and Re-Oxygenation

TKPTS cells were subjected to hypoxia using a hypoxic chamber (Stemcell Technologies) for 6 hrs (5% $CO_2$, 1% $O_2$, and 94% $N_2$) followed by re-oxygenation for 6 hrs (5% $CO_2$, 21% $O_2$, and 74% $N_2$). Three culture conditions were set up: 1. Normoxia (which served as the base line control); 2. Hypoxia; and 3. Cells pretreated with 50 µM hepcidin and subjected to hypoxia. Experiments were carried out in serum free advanced DMEM/F12 medium. At the end of re-oxygenation, cells were stained with Annexin V/PI and extent of apoptosis was determined using flow cytometry.

Iron Stimulation of Splenocytes

Splenocytes were harvested from 10-week-old B6 male mice. After excising the spleen, red blood cells were lysed and the remaining splenocytes were seeded at 1×106 cells/mL in 24-well tissue culture plates and cultured under 5% CO2 at 37° C. for 24 hours. The culture medium consisted of RPMI 1640 medium supplemented with 10% fetal calf serum (FCS), 100 U/mL penicillin, 100 µg/mL streptomycin, 1% non-essential amino acids (Gibco/Life Technologies, Foster, Calif., USA), 2 mM L-glutamine (Sigma), and 50/µM 2-mercaptoethanol. After resting for 24 hours, the cells were treated with 10 µM ferric ammonium chloride (FAC), 1 µg/mL hepcidin or saline for 4 hours. The cell culture supernatants were harvested and quantified for the levels of IL-6 by ELISA (eBioscience).

Western Blot Analysis

Snap frozen tissue sections were homogenized in Tris-Triton tissue lysis buffer containing complete protease inhibitor cocktail using a Dounce Homogenizer. Membrane fractions were isolated from the whole kidney lysate using membrane isolation kit (Thermo Pierce) to determine ferroportin expression. H-Ferritin was measured in the whole kidney and spleen lysates. Protein content in the homogenate was estimated using the BCA protein estimation kit. Twenty to thirty microgram of protein per sample were loaded on a 10% NuPage Bis-Tris gel under reducing conditions. The resolved proteins were transferred onto a Nitrocellulose membrane (Licor Bioscience) and probed with goat anti-mouse H-Ferritin (Santa Cruz) and rabbit anti-mouse ferroportin (Novus Biologics) antibodies. The primary antibodies were detected with Donkey anti-goat Alexa 800 and goat anti-rabbit Alexa 800 antibodies (LiCor Bioscience). Mouse monoclonal GAPDH and β-Actin (Abcam) were used as the loading controls and detected using Donkey anti Mouse Alexa 680 antibody (LiCor Bioscience). Quantitation of data was performed using densitometry software (Licor Bioscience).

Real Time PCR

For RNA isolation, frozen tissues were re-suspended in RLT buffer (Qiagen Inc, Valencia, Calif.) and homogenized using TissueLyser system (Qiagen Inc, Valencia, Calif.). Total RNA from tissue homogenate was purified using RNAeasy mini kit (Qiagen Inc, Valencia, Calif.) following manufacturers instructions. 1 µg of RNA was used to synthesize cDNA using the iScript cDNA synthesis kit (Bio-Rad). The cDNA template was mixed with iTAQ SYBR green universal super mix (Bio-Rad) and quantitative PCR was carried out on CFX Connect system (Bio-Rad). Predesigned primers for Caspase-3 and Bcl-2 were purchased from Bio-rad. Glyceraldehyde-3-phosphate dehydrogenase (GAPDH) was amplified in parallel and used as the reference gene in quantification. Data is expressed as the relative gene expression and was calculated using the 2 $(-\rho\rho C(T))$ method.

Statistics.

GraphPad Prism 6 (GraphPad Inc.) was used to analyze and present the data. Data were analyzed, after transformation if needed to generate a normal distribution, by t test or 1-way ANOVA with post hoc analysis as appropriate. $P<0.05$ was used to indicate significance.

Hepcidin Agonist PR73 (Mini-Hepcidin)—

This 10 amino acid peptide agonist of Hepcidin was used in animals at either 100 or 200 nmol. Its description and sequence can be found in WO2013086143 A1 (Ganz et al.). The effects on plasma creatinine levels were determined.

Results

Hepcidin Prevents Renal Ischemia-Reperfusion Induced Iron Dyshomeostasis

Figure 1A:
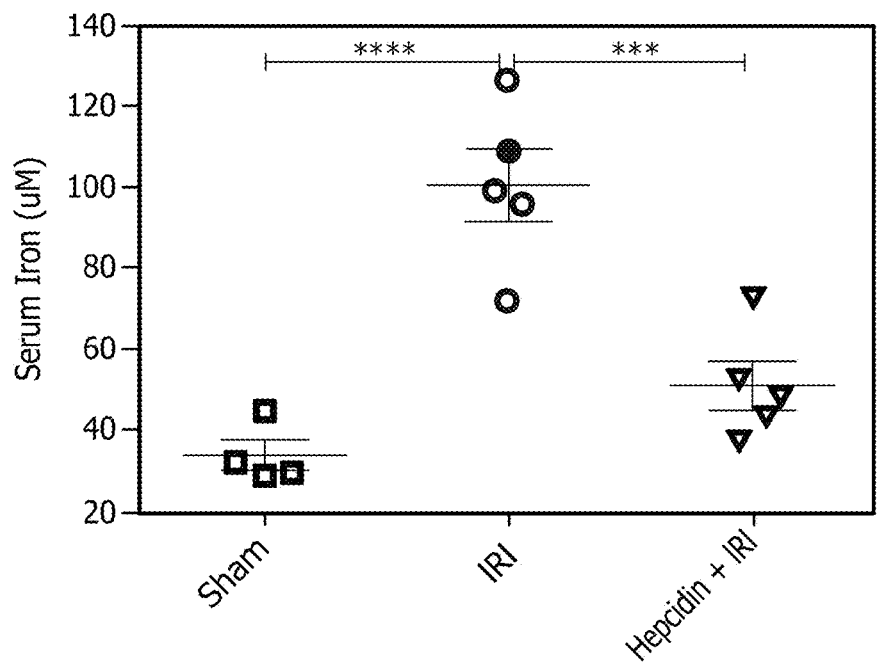
FIG. 1, comprising FIGS. 1a to 1f. Renal IRI is associated with changes in systemic iron levels and upregulation of endogenous Hepcidin, which are prevented by exogenous Hepcidin. Serum iron was measured by ELISA and normalized to sample volume (a). Non-heme iron was measured following acid digestion of Kidney (b), Liver (c), and Spleen (d) normalized to tissue weight and expressed as micro gram per gram tissue. Liver RNA was isolated, cDNA was amplified and normalized to GAPDH (e). Hepcidin content in the serum was measured by ELISA (f). Sham (□), IRI (○) and Hepcidin+IRI (▽). *P<0.05, P<0.005, *P<0.0005, ****P<0.0001. Data points are plotted as mean±SEM (n=4-5 per group).
Figure 1B:
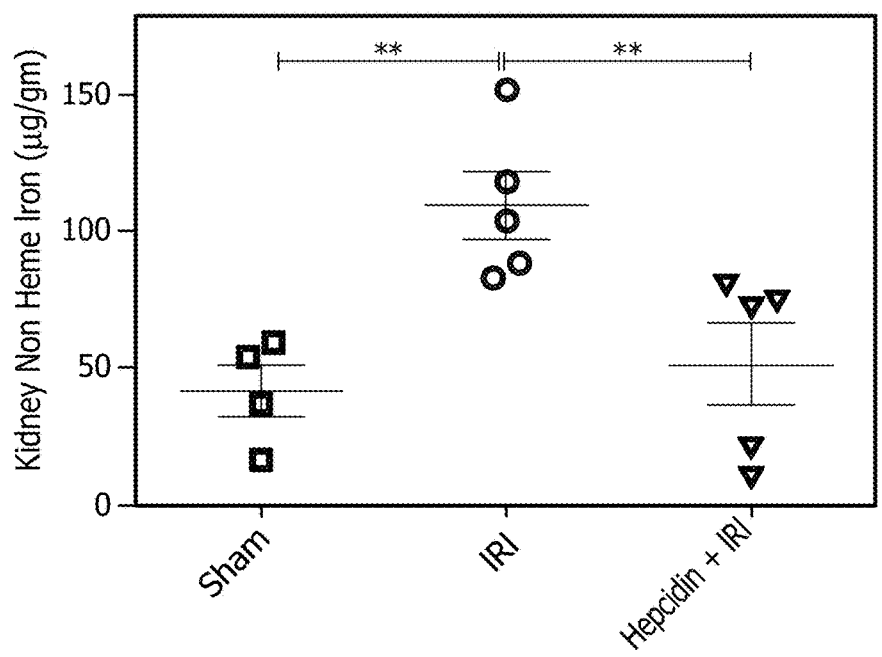
Figure 1C:
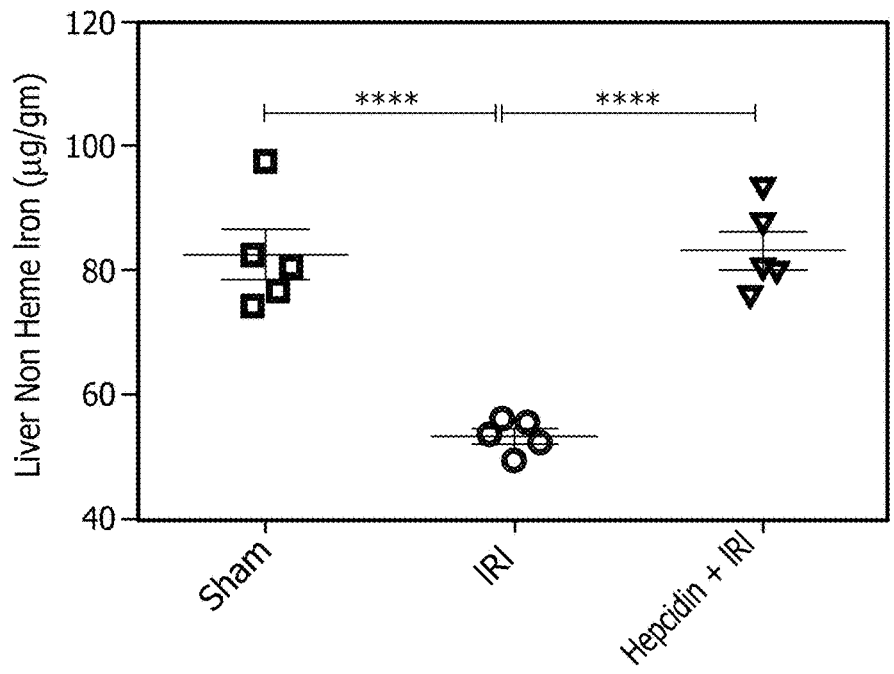
Figure 1D:
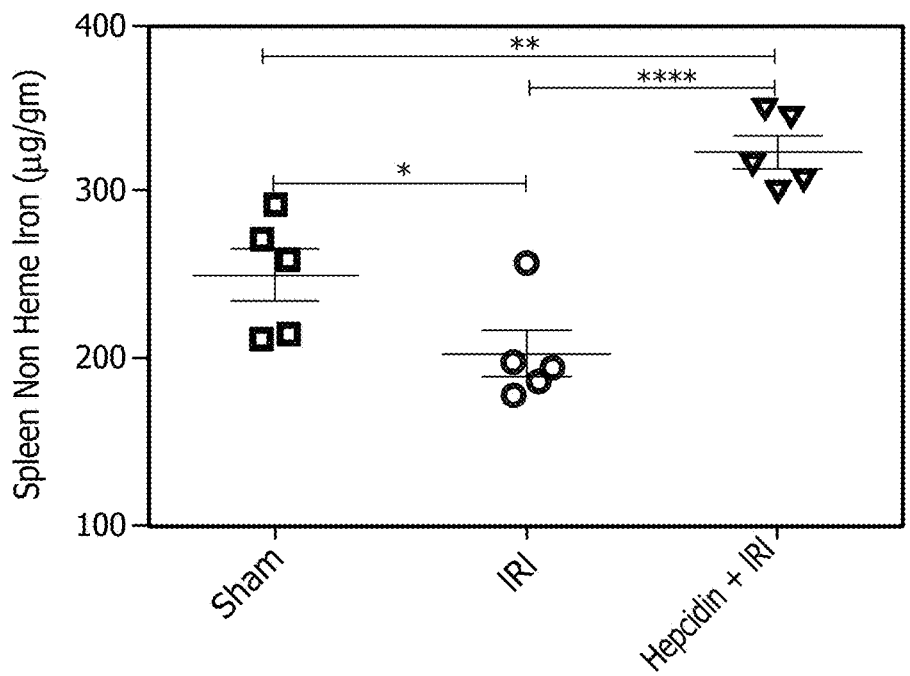

There is a dynamic and continuous exchange of iron between hepatosplenic compartments and the plasma. This process is regulated by hepcidin through its modulation of reticuloendothelial (splenic red pulp macrophages and hepatic Kupffer cells) ferroportin expression. While prior studies have demonstrated increased serum iron levels following renal IRI, no previous studies have characterized the dynamic changes in iron distribution between different organ and tissue compartments following renal IRI. Here, we first confirmed the previous observations that renal IRI triggers a significant increase in serum iron levels compared to the sham operated animals (FIG. 1a, $p<0.0005$). Hepcidin treatment significantly reduced IRI-induced increase in serum iron levels (FIG. 1a, $p<0.001$). We next measured non-heme iron levels in the kidney, spleen and liver of the animals. IRI was associated with a significant increase in kidney non-heme iron content compared to sham operated animals (FIG. 1b, $p<0.001$) and hepcidin treatment significantly prevented IRI-induced kidney iron accumulation (FIG. 1b, $p<0.05$). Next, we determined the non-heme iron content in the spleen and liver of the three experimental groups. Hepcidin treated mice had a significantly higher splenic non-heme iron content than IRI or sham groups (FIG. 1c, $p<0.001$ and $<0.05$ respectively). In IRI group, liver non-heme iron levels were significantly less than the sham group (FIG. 1d, $p<0.0005$) and hepcidin treatment effectively prevented IRI-induced depletion of liver non-heme iron (FIG. 1d, $p<0.0001$).

Figure 1E:
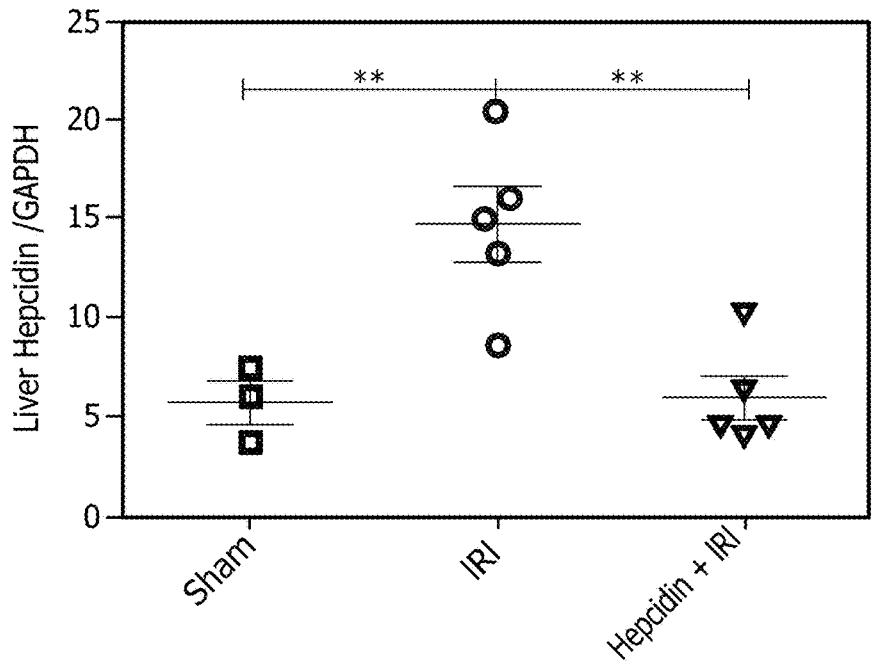
Figure 1F:
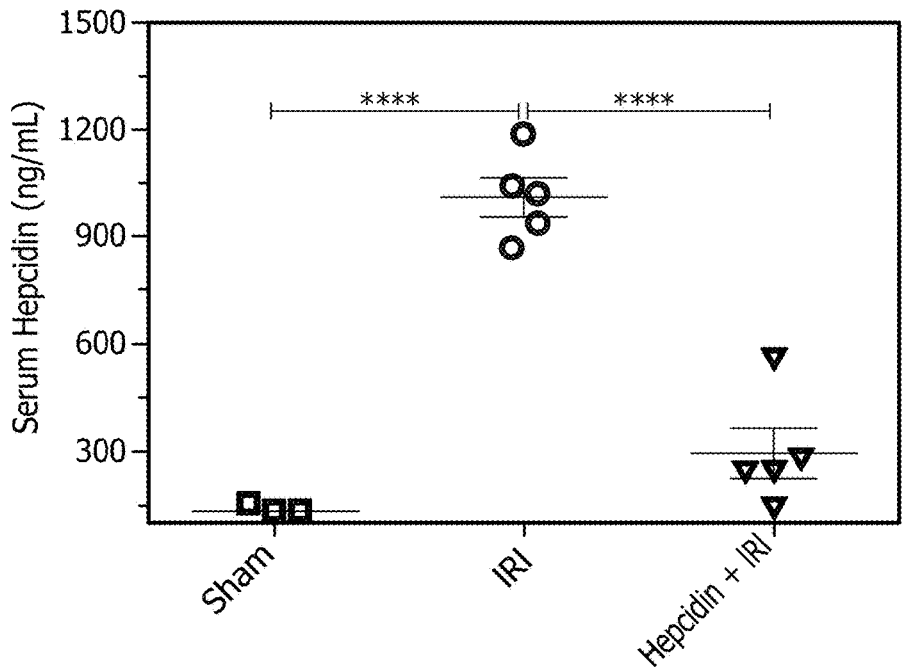

Increase in serum iron levels following renal IRI raised the question whether this would result in an iron-dependent increase in hepcidin synthesis and release. We, therefore, measured hepcidin expression (transcripts and protein) in the liver and serum of the three experimental groups of mice. Renal IRI resulted in a significant upregulation of liver hepcidin gene expression compared to sham mice (FIG. 1e, $p<0.005$). Hepcidin treatment before IRI significantly prevented the IRI-induced upregulation of hepcidin with gene expression levels comparable to sham operated animals (FIG. 1e, IRI Vs. Hepcidin-IRI, $p<0.005$). Serum hepcidin paralleled these changes with levels significantly elevated following IRI in untreated mice as compared to sham (FIG. 1f, IRI Vs Sham, $p<0.0001$) or hepcidin-treated mice (FIG. 1f, IRI Vs Hepcidin-IRI, $p<0.0001$). Hepcidin levels were not significantly different between hepcidin-treated and sham groups.

Collectively, our observations indicate that IRI induces dynamic changes in iron metabolism characterized by hepatosplenic iron depletion, systemic iron mobilization, kidney non-heme iron accumulation and post-IRI hepcidin induction. Hepcidin treatment before IRI effectively prevents these changes.

Hepcidin Mitigates IRI, Reduces ATN and Improves Renal Function

Figure 2B:
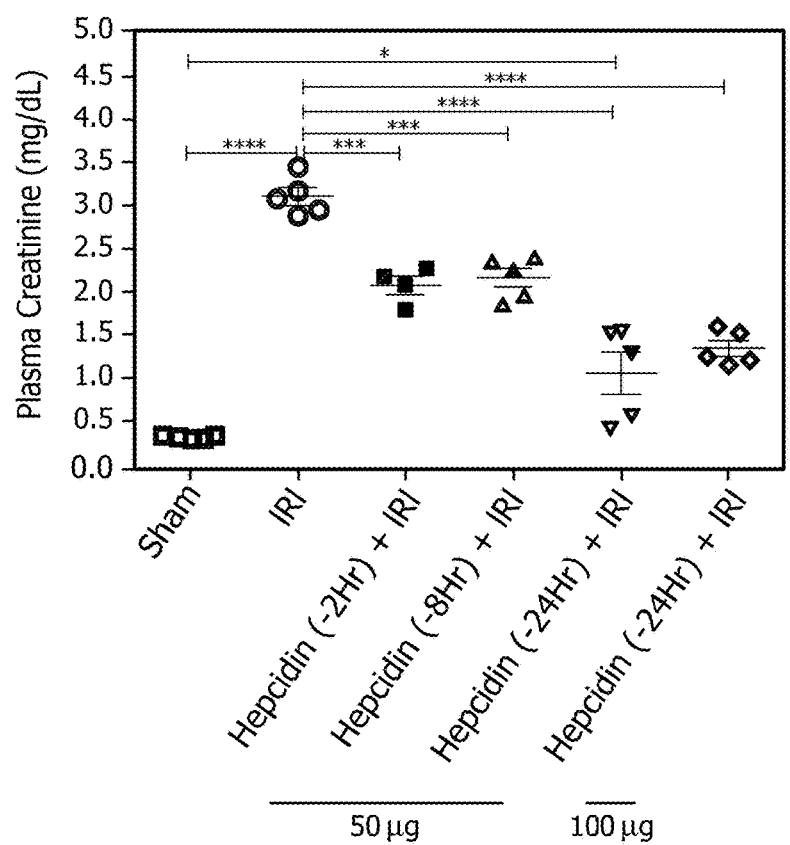

As iron plays an important role in renal IRI, next, we examined the functional significance of hepcidin-mediated modulation of iron homeostasis on IRI. Compared to sham, plasma creatinine of untreated IRI mice was significantly higher (FIG. 2b, p<0.0001). A single bolus of 50 or 100 μg hepcidin (intraperitoneally), 24 hours before IRI, significantly lowered plasma creatinine levels (FIG. 2b, p<0.0001). As there were no significant differences in plasma creatinine of mice injected with either 50 or 100 g hepcidin, all further experiments were performed using 50 μg hepcidin dose.

We next established the timing of hepcidin injection that would offer maximum protection against IRI. We injected mice with either hepcidin or water at 2 or 8 hours prior to ischemia and measured plasma creatinine 24 hours after reperfusion. Remarkably, hepcidin injection at both 2 and 8 hours prior to IRI significantly reduced plasma creatinine levels (FIG. 2b, p<0.001 compared to untreated IRI mice). However, maximum protection was observed when hepcidin was injected 24 hours before IRI (FIG. 2b). Hence, in all further experiments, hepcidin was injected 24 hours before IRI.

The protective role of hepcidin was also evidenced by a better-preserved renal architecture that correlated well with the creatinine levels. Following IRI, kidney sections of untreated mice showed extensive tubular necrosis all the way from the S3 segment in the outer strip of the outer medulla and extended to the S1 and S2 segment of the proximal tubule in the deep cortex (FIG. 2d, Sup FIG. 1b). However, hepcidin-treated mice had fewer necrotic tubules and luminal debris in the S1 and S2 segments of the proximal tubules and exhibited normal epithelial morphology. The S3 segment of the outer medulla also demonstrated substantially reduced tubular damage and less evident tubular casts (FIG. 2e, Sup FIG. 1c). The preserved renal function and architecture was associated with significant reduction in kidney injury marker neutrophil gelatinase-associated lipocalin (NGAL). Renal IRI resulted in a significant increase in NGAL (Sup FIG. 1e, IRI Vs Sham, p<0.0001). In contrast, the hepcidin-treated IRI mice had significantly lower expression of NGAL (Sup FIG. 1d, IRI Vs Hepcidin-IRI, p<0.001). Collectively, these findings demonstrated a protective role of hepcidin in renal IRI.

Hepcidin Decreases Ischemia-Induced Renal Epithelial Apoptosis.

Figure 3A:
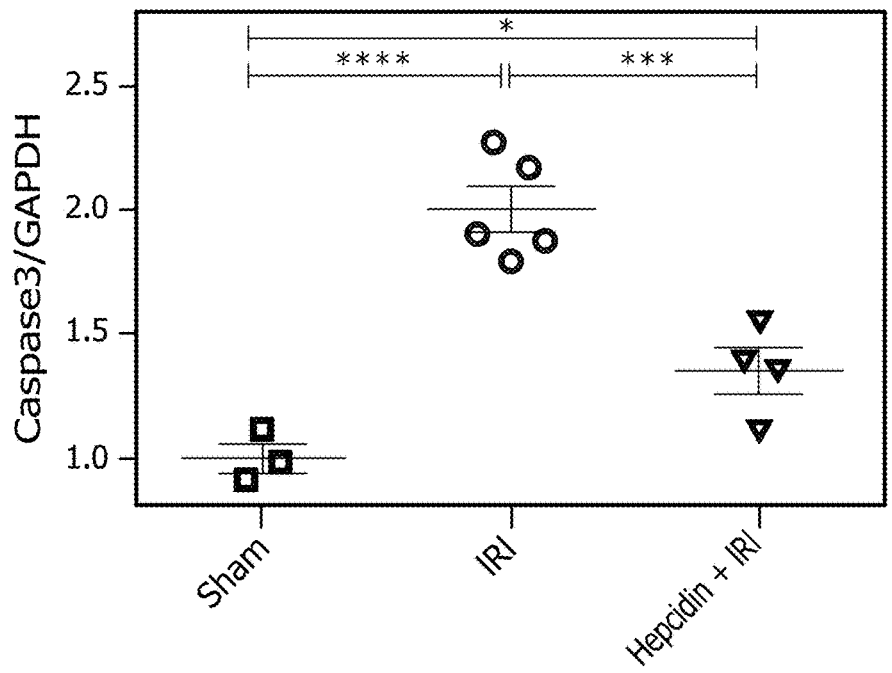
FIG. 3, comprising FIGS. 3a to 3h. Hepcidin reduces apoptosis in the kidneys of mice following IRI and in renal tubular cell line subjected to hypoxia-reoxygenation regimen. Hepcidin treatment protects kidney from IRI induced apoptosis. Mice receiving Hepcidin before IRI had a lower transcriptional activation of pro apoptotic Caspase3 (a) and better preservation of anti apoptotic Bcl2 (b). Sham (□), IRI (○) and Hepcidin+IRI (▽). n=3-5. Data for a and b are represented as mean±SEM of $2^{\Delta\Delta CT}$ values normalized to GAPDH. TUNEL reactivity was used to assay apoptosis after renal IRI. Untreated IRI mice showed severe apoptosis in the cells of the corticomedullar region (c and d), which was reduced by Hepcidin pretreatment (e-f). Representative images from two different experiments with 4-5 mice each are depicted. Magnification (c and e) 10×, (d and f) 20×. TKPTS cells were treated with or without 50 μM Hepcidin for 24 hours, before subjecting them to 1% Hypoxia for 6 hours followed by 6 hours of reoxygenation (g-h). Untreated cells cultured under normoxic conditions were used as controls After 6 hrs of re-oxygenation, cells were stained for Annexin V-PI (g-h) and flow cytometry was used to determine the extent of apoptosis. Normoxia (□), Hypoxia (○), and Hepcidin-Hypoxia (▽) (g-h). Representative of 2 independent experiments. *P<0.05, P<0.005, *P<0.0001. Data points are plotted as mean±SEM.
Figure 3B:
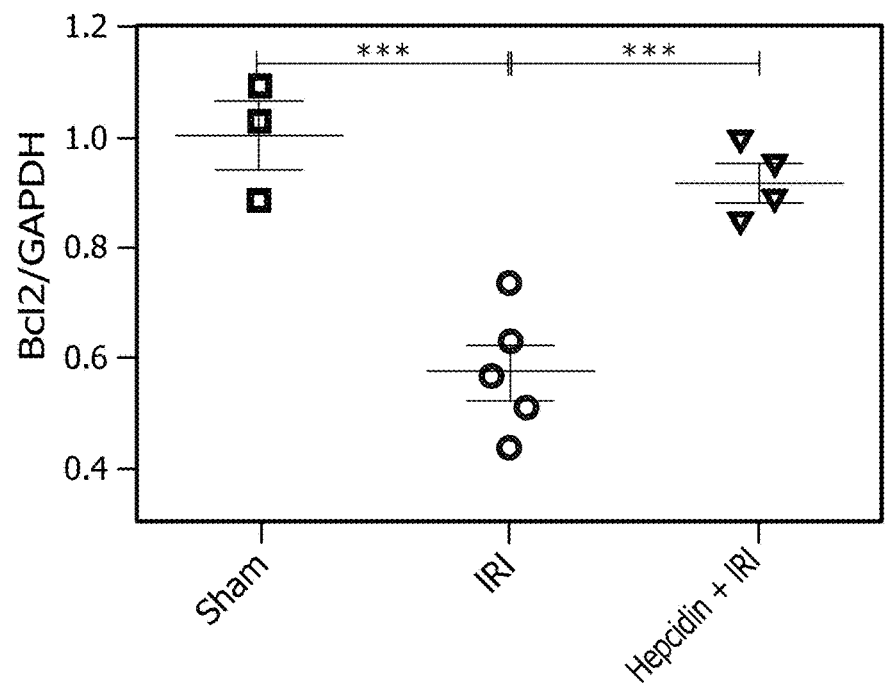
Figure 3E:
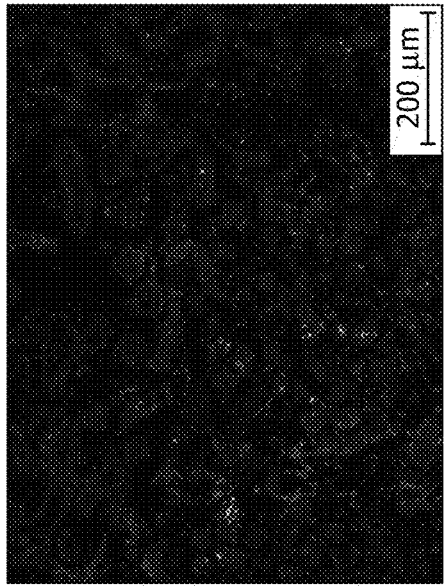
Figure 3C:
Figure 3F:
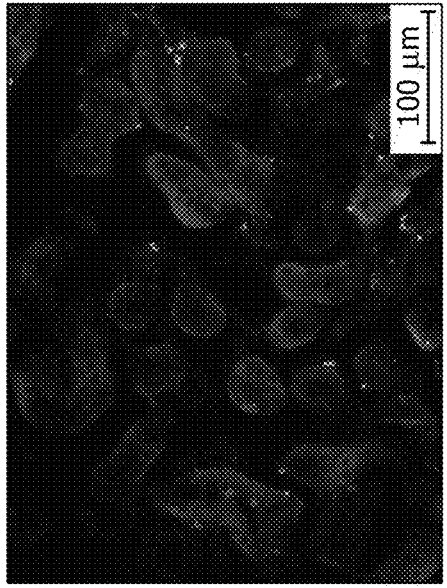
Figure 3D:
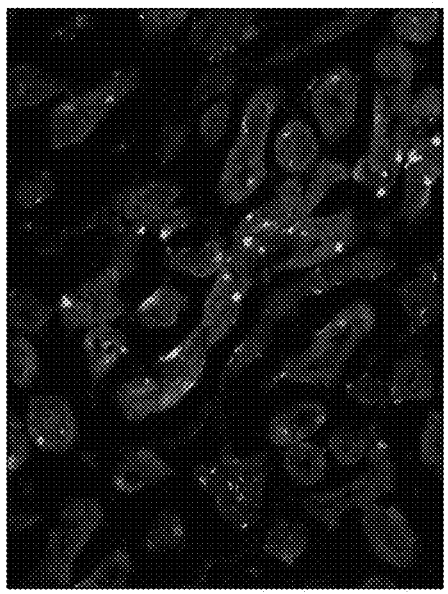

Apoptosis is a major mediator of tubular cell death following renal IRI (33) and iron can trigger renal epithelial apoptosis. To investigate if hepcidin-mediated protection in renal IRI is mediated through modulation of epithelial apoptosis, we measured apoptosis-related genes in kidneys of the 3 experimental groups. Compared to sham operated mice, Caspase-3 was significantly upregulated in the kidneys of untreated IRI mice (FIG. 3a, p<0.0001). Hepcidin treatment significantly reduced IRI-induced Caspase-3 expression in the kidneys (FIG. 3a, p<0.005). Interestingly, Caspase-3 expression in the kidneys of hepcidin treated mice was even lower than the sham mice (FIG. 3a, Hepcidin-IRI Vs Sham, p<0.03). Expression of Bcl-2, an anti-apoptotic gene, with known protective properties in renal IRI (34), was also different in the three groups. Bcl2 expression was significantly reduced in IRI mice compared to sham (FIG. 3b, p<0.0008) and hepcidin-IRI mice had a significantly higher expression of Bcl2 compared to untreated IRI mice (FIG. 3b, p<0.0008). To further establish the observed reduction in apoptosis in the hepcidin-IRI mice, we stained the kidney sections with terminal deoxynucleotidyl transferase-mediated digoxigenin-deoxyuridine nick-end labeling (TUNEL) as an indicator of apoptosis. We did not detect any TUNEL-positive cells in kidney sections of sham-operated mice (data not shown). As expected, 26 minutes of renal ischemia followed by 24 hours of reperfusion resulted in a significant increased in TUNEL reactivity in the nuclei of the renal tubules (FIG. 3c-d). In contrast, hepcidin-IRI mice had remarkably fewer TUNEL-positive tubules in the kidney (FIG. 3e-f).

Figure 3G:
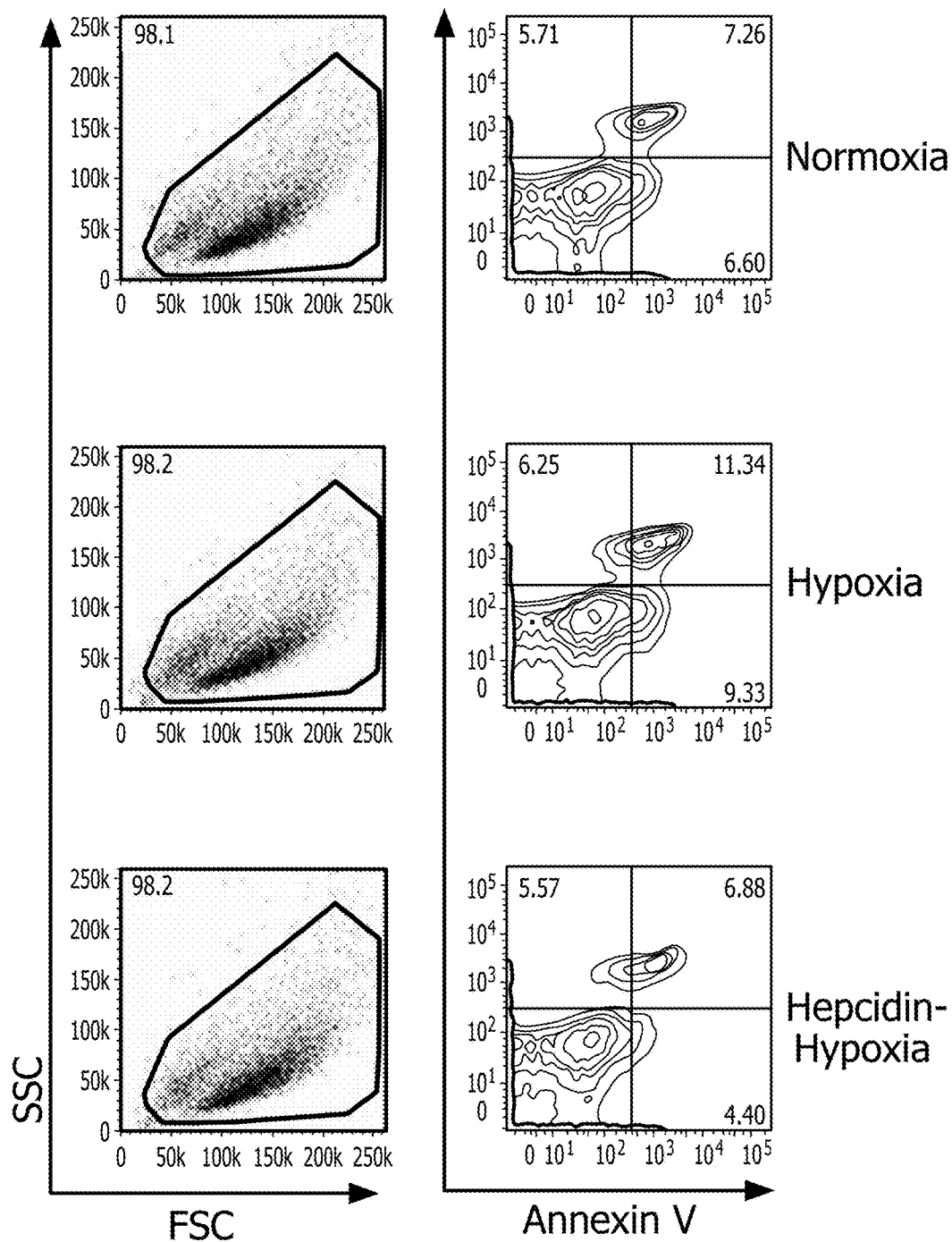
Figure 3H:
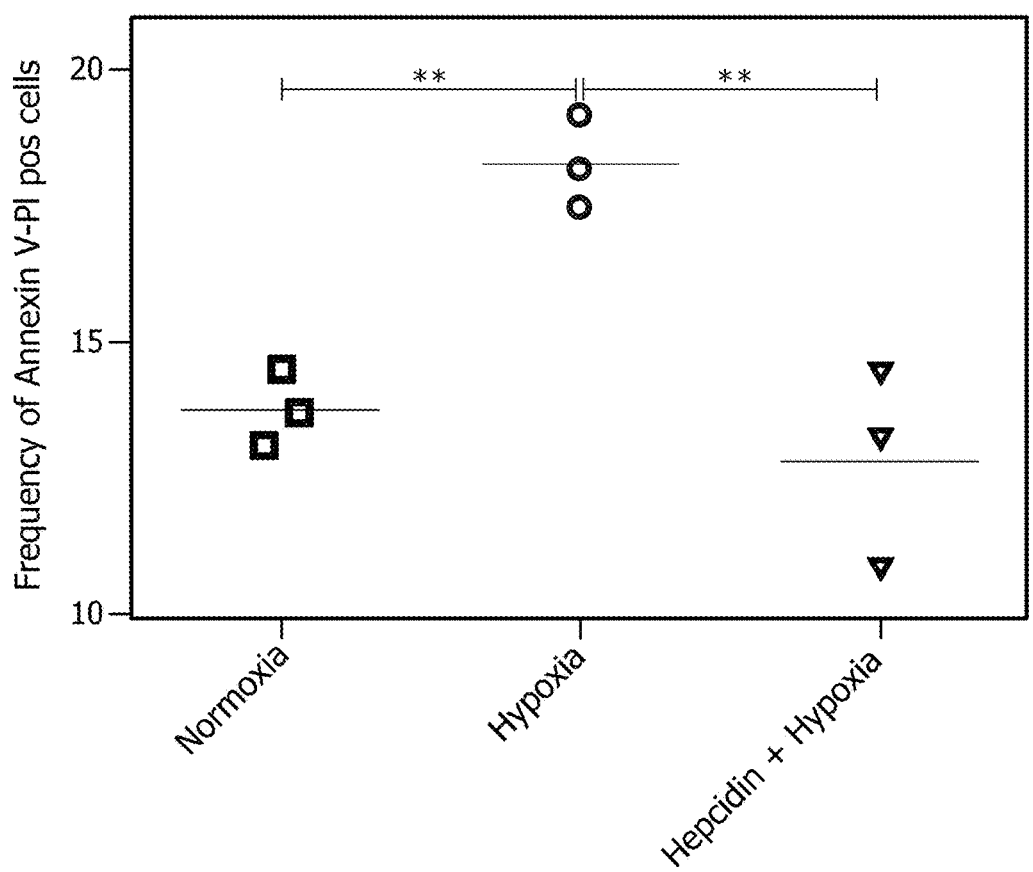

To investigate if hepcidin has a direct anti-apoptotic effect on renal tubular epithelial cells, we subjected murine proximal renal tubular cells (TKPTS) to hypoxia-reoxygenation injury in vitro (34). TKPTS cells were first treated with or without 50 μM hepcidin for 24 hours in 5% serum containing medium. After transferring to serum free medium, the cells were then cultured in 1% hypoxia for 6 hours. Cells cultured under identical but normoxic conditions were used as controls. After 6 hours of re-oxygenation, cells were stained for Annexin V/PI to measure the extent apoptosis/necrosis induced by the hypoxic-reoxygenation insult. Hypoxia led to a significant increase in Annexin V/PI positive cells compared to normoxic condition (FIG. 3g-h, p<0.005). However hepcidin-treated cells subjected to hypoxia demonstrated significantly lower Annexin V/PI staining compared to untreated cells (FIG. 3g-h, p<0.005) and the frequency of cells undergoing apoptosis were reduced to levels seen under normoxia (FIG. 3g-h). These findings reinforce our in-vivo observations and suggest a direct anti-apoptotic role of hepcidin.

Hepcidin Treatment Reduces Renal IRI-Induced Oxidative Stress and Inflammation.

Oxidative stress-induced apoptotic cell death is believed to be one of the major pathways involved in the pathogenesis of kidney I/R injury (35, 36). Iron is known to play central player in triggering oxidative tissue injury through its ability to redox cycle and generate oxidative radicals such as hydroxyl (OH). Iron chelation with desferrioxamine and antioxidants such as superoxide dismutase (SOD) attenuate IRI (37-39). Since hepcidin treatment directly modulates IRI-associated iron dyshomeostasis, we examined whether the reduced injury observed with hepcidin treatment is associated with lowering of oxidative stress. 4-Hydroxynonenal (4-HNE), an aldehyde product of membrane lipid peroxidation is produced by oxidative stimuli and is conventionally used as a tissue marker of oxidative stress (40). Kidneys of untreated IRI mice showed prominent 4-HNE immunoreactivity, indicative of lipid peroxidation and oxidative injury (FIG. 4a (top panel), and Sup FIG. 2a). The pattern of staining mirrored renal injury distribution, being most intense in the medulla and spreading out with lesser intensity in the corticomedullary junction and deep cortex. As compared to the untreated mice, kidneys of hepcidin-treated mice showed far less 4-HNE immunoreactivity. Only a restrictive 4-HNE staining could be detected in some regions of the deep medulla and corticomedullary junction (FIG. 4a (bottom panel) and Sup FIG. 2b). Further, the intensity of staining was significantly less compared to the untreated mice. Taken along with the effect of hepcidin in preventing renal iron accumulation, these findings support the inhibitory effect of hepcidin treatment on renal IRI-induced oxidative stress.

Figure 4A:
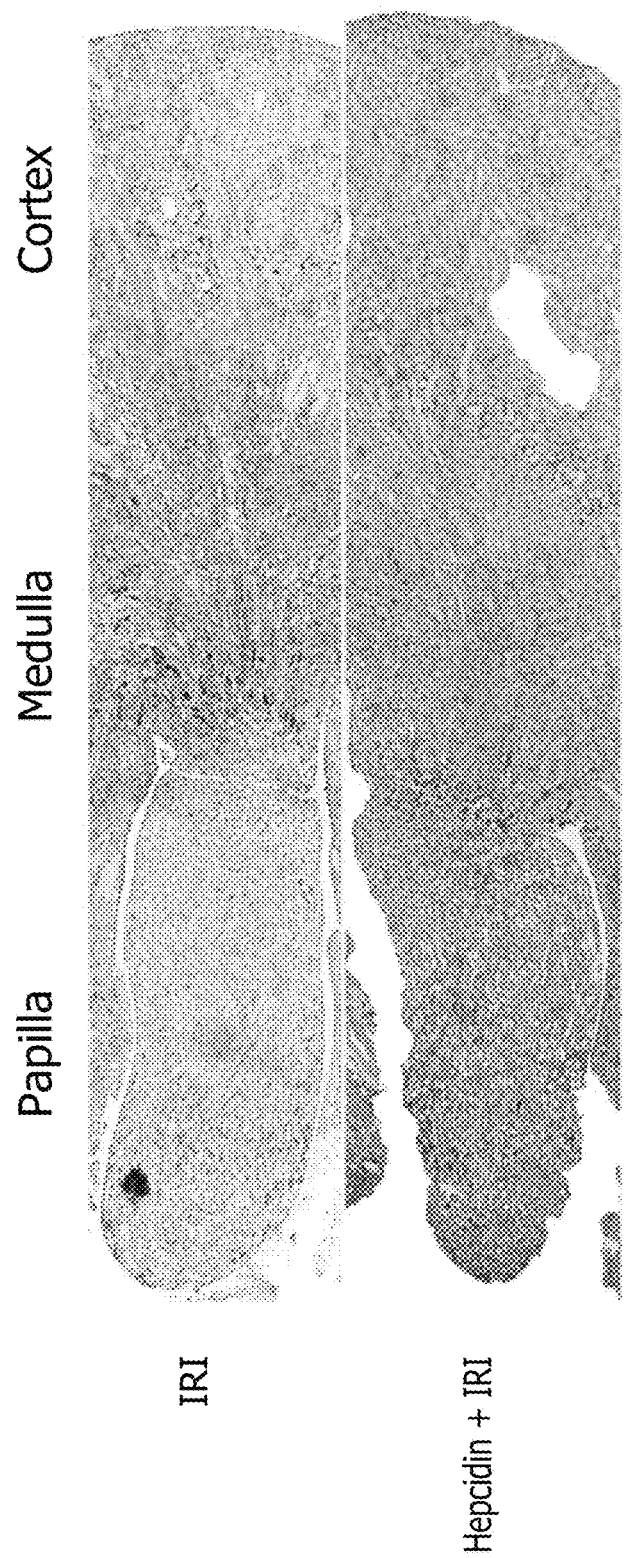
FIG. 4, comprising FIGS. 4a to 4c. Hepcidin reduces oxidative stress in the kidney following IRI and is associated with reduced infiltration of CD45 positive cells and neutrophils. Reactivity to 4 hydroxynonenal (4 HNE) was used as a measure of oxidative stress in the kidney after IRI. Renal IRI resulted in generation of ROS mediated oxidative stress as observed by strong reactivity to 4HNE especially in the cortico-medullar region (a) top panel. Hepcidin treated kidneys had reduced the reactivity to 4 HNE indicative of reduced oxidative stress (a) bottom panel. Representative images from two different experiments with 4-5 mice each are depicted. Magnification: 10×. Infiltration of immune cells (CD45+ve) and neutrophils (Ly6G-Ly6c positive cells within CD45-CD11b+ve gates) in kidneys of sham, IRI and Hepcidin treated IRI mice were studied by FACS (b). Representative gates depicting CD45, CD11 b, and Ly6GLy6c populations are shown in FIG. 4b. The frequency of total CD45 cells (upper panel) as well as neutrophils (lower panel) was reduced in Hepcidin treated mice compared to untreated ones (c). Data are from one of the 3 different experiments with 4-5 mice in each group. Sham (□), IRI (○) and Hepcidin+IRI (▽). P<0.001, *P<0.005, ****P<0.000. Data points are plotted as mean±SEM.
Figure 4B:
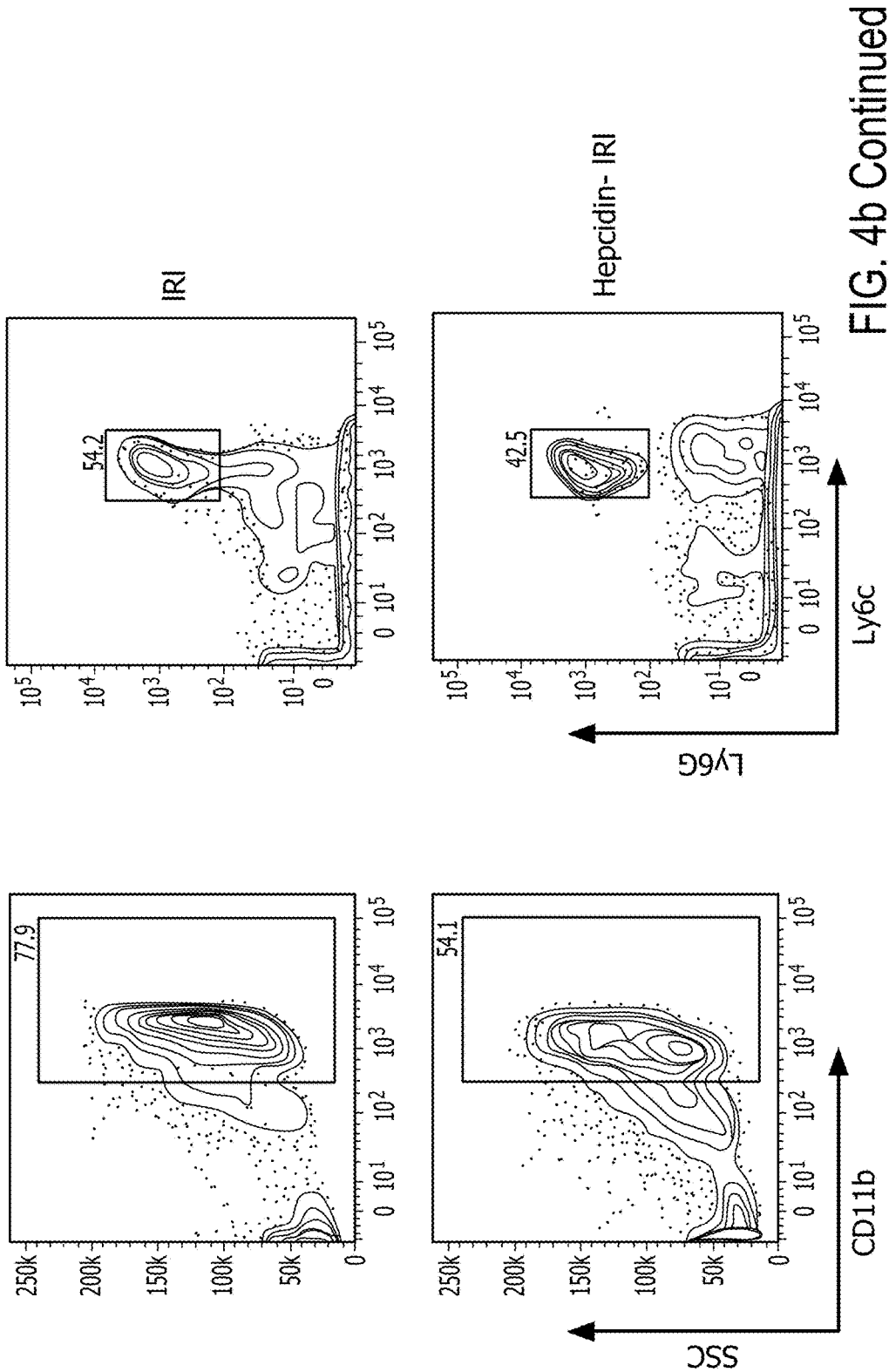
Figure 4C:
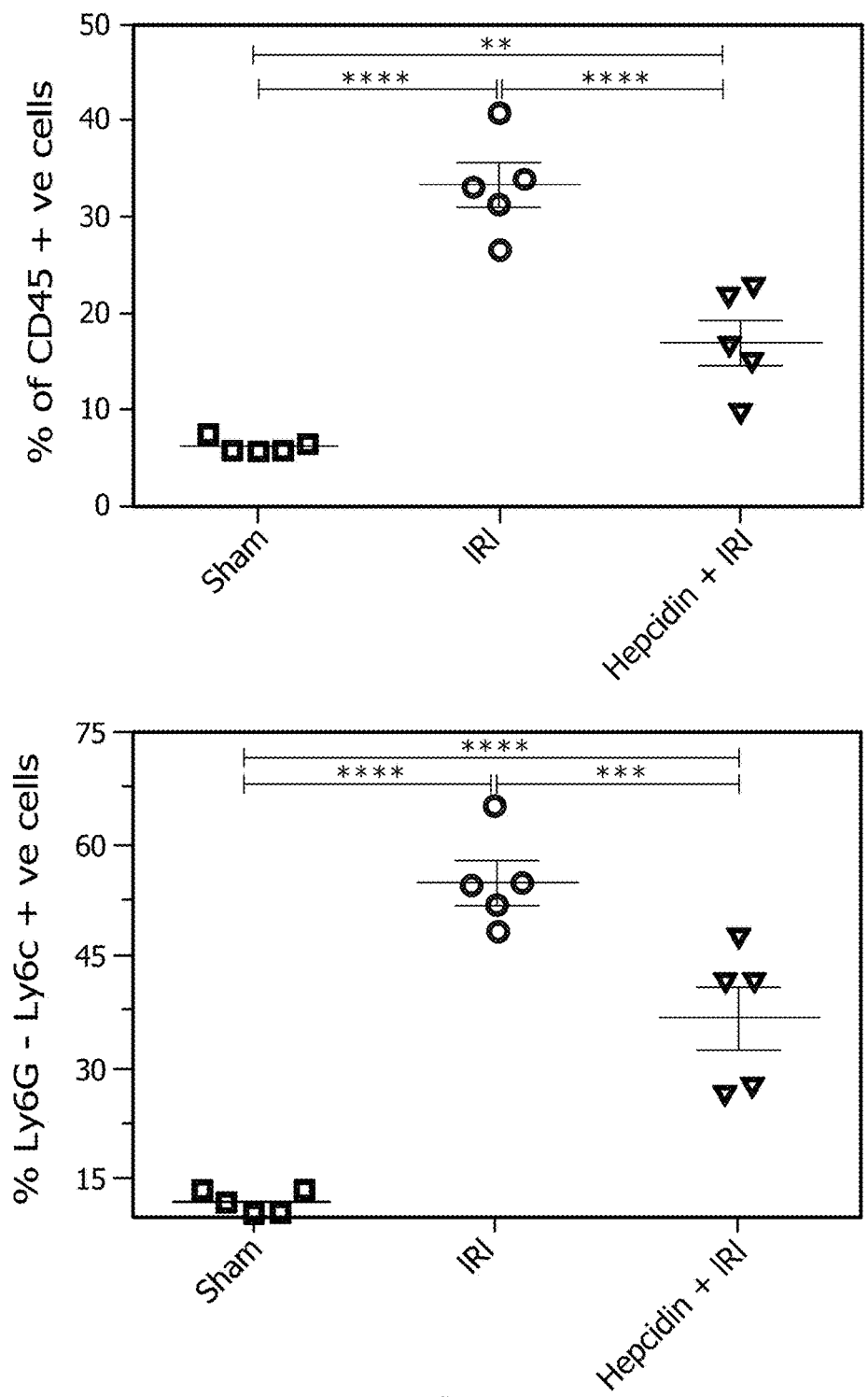

Apoptosis and ROS generation are early events following renal IRI and is followed by the infiltration of immune cells which leads to the amplification of kidney pathology (33, 35, 6). Multiple previous studies have linked the infiltration of immune cells with renal pathology following IRI (41, 42). Therefore we investigated whether the reduced apoptosis and ROS seen with hepcidin treatment is associated with decreased kidney infiltration of inflammatory cells. Compared to sham operated mice, IRI in untreated mice resulted in a large and significant increase in the frequency of kidney CD45+ cells (FIG. 4b-c, p<0.005). However, hepcidin treatment reduced renal inflammatory cell infiltration by almost half (FIG. 4b-c, p<0.005). Prior studies have shown that neutrophils comprise the majority of immune cells that infiltrate the kidneys following I/R injury (41). We identified neutrophils as CD45$^+$CD11b$^{hi}$Ly6G$^-$Ly6C$^{hi}$ cells. As expected, neutrophils were the most abundant immune cells in the kidneys following IRI (FIG. 4c, p<0.005). Hepcidin treatment significantly reduced IRI-induced renal neutrophil inflammation compared to the untreated IRI mice (FIG. 4c, p<0.005). Collectively, these observations demonstrate that hepcidin treatment reduces renal IRI-associated inflammation.

Hepcidin Preserves Cytoprotective H-Ferritin by Preventing IRI-Induced Renal Ferroportin Induction.

The primary known function of hepcidin is to induce ferroportin degradation and increase intracellular iron stores. In turn, this results in the induction of H-Ferritin, an iron binding ferrooxidase with cytoprotective function (43). To address if the protection observed in our studies is due to hepcidin-induced ferroportin degradation and increased H-Ferritin, we measured the expression of these proteins in kidneys of sham, IRI and hepcidin-IRI mice. Ferroportin expression was increased in the kidneys of IRI mice compared to sham mice (FIG. 5a-b, p<0.05). Pretreatment with hepcidin maintained ferroportin expression (and thus maintain intracellular iron levels) at levels comparable to sham mice (FIG. 5a-b, p<0.01). Correlating with these changes in ferroportin (expected to induce intracellular iron depletion), H-Ferritin levels were significantly lower in the kidneys following IRI (FIG. 5c-d). Hepcidin treatment was associated with significantly higher H-Ferritin expression compared to both untreated IRI mice and sham mice (FIG. 5c-d, hepcidin-IRI Vs IRI p<0.005, hepcidin-IRI Vs Sham p<0.05). Collectively, our data demonstrates that renal IRI is associated an increase in kidney ferroportin and decrease in kidney H-Ferritin and hepcidin treatment prevents these changes.

Hepcidin Deficiency Increases Susceptibility to AKI

Figure 6A:
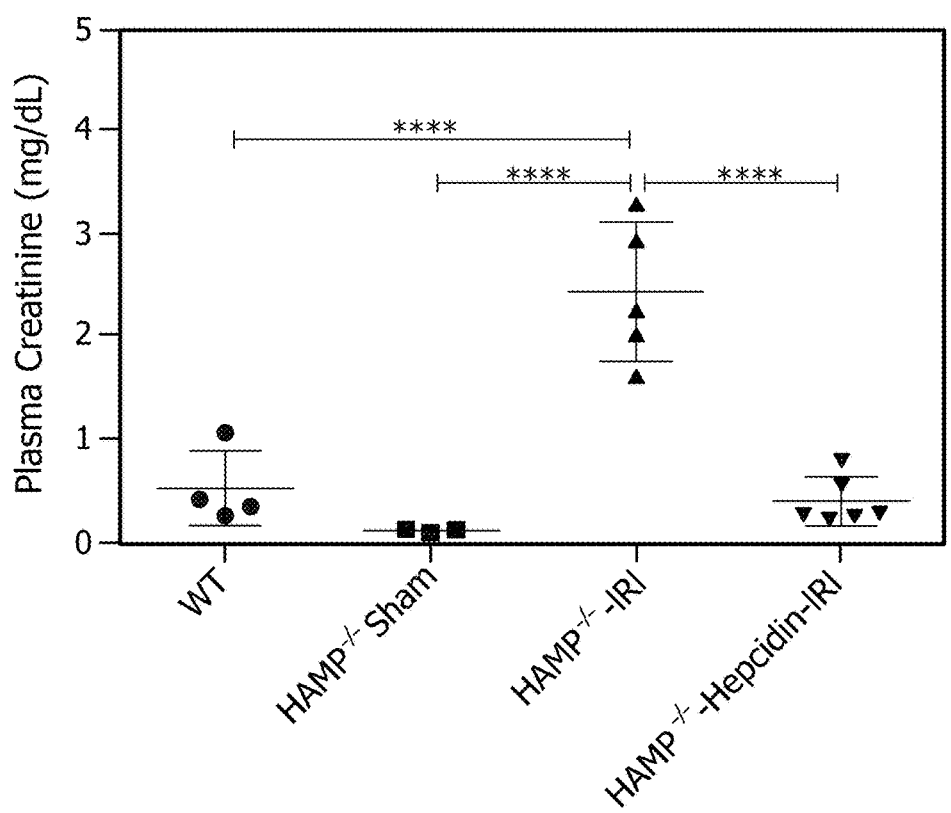
FIG. 6, comprising FIGS. 6a to 6f. Genetic loss of hepcidin exacerbates renal IRI and is mitigated by reconstitution with exogenous Hepcidin. HAMP$^{-/-}$ mice treated with saline or Hepcidin and untreated WT mice (HAMP sufficient) were subjected to mild IRI (24 mins ischemia), and plasma creatinine was measured after 24 hours after IRI (a). The WT mice had a mild but insignificant rise in plasma creatinine (●) compared to sham operated HAMP$^{-/-}$ mice (■). Untreated HAMP$^{-/-}$-IRI mice showed highly significant creatinine (▲) compared to shams. Hepcidin reconstitution rescued the HAMP$^{-/-}$ mice from IRI (▼) and their serum creatinine values were not significantly different than shams and WT mice. Data are represented as mean±SEM. ****P<0.0001, (n=3-5 per group). Representative morphology of HAMP$^{-/-}$ kidneys (by H&E staining) 24 hours after sham operation (b), IRI (c,) and hepcidin treatment IRI (d) shows Hepcidin mediated protection of the kidney after IRI. Magnification: 10×. Serum iron was measured by ELISA and normalized to sample volume (e). Hepcidin reconstitution significantly reduced serum iron in HAMP$^{-/-}$-IRI mice compared to both untreated HAMP$^{-/-}$-IRI and HAMP$^{-/-}$ sham operated mice. Non-heme iron was measured following acid digestion of Liver, normalized to tissue weight and expressed as micro gram per gram tissue (f). Hepcidin treated HAMP$^{-/-}$-IRI mice had significantly higher non-heme iron compared to both untreated HAMP$^{-/-}$-IRI and HAMP$^{-/-}$ sham operated mice. HAMP$^{-/-}$ Sham (●), HAMP$^{-/-}$-IRI (■) and HAMP$^{-/-}$-Hepcidin-IRI (▲). *P<0.05, P<0.005, *P<0.0005, ****P<0.0001. Data points are plotted as mean±SEM.
Figures 6B, 6C, 6D:
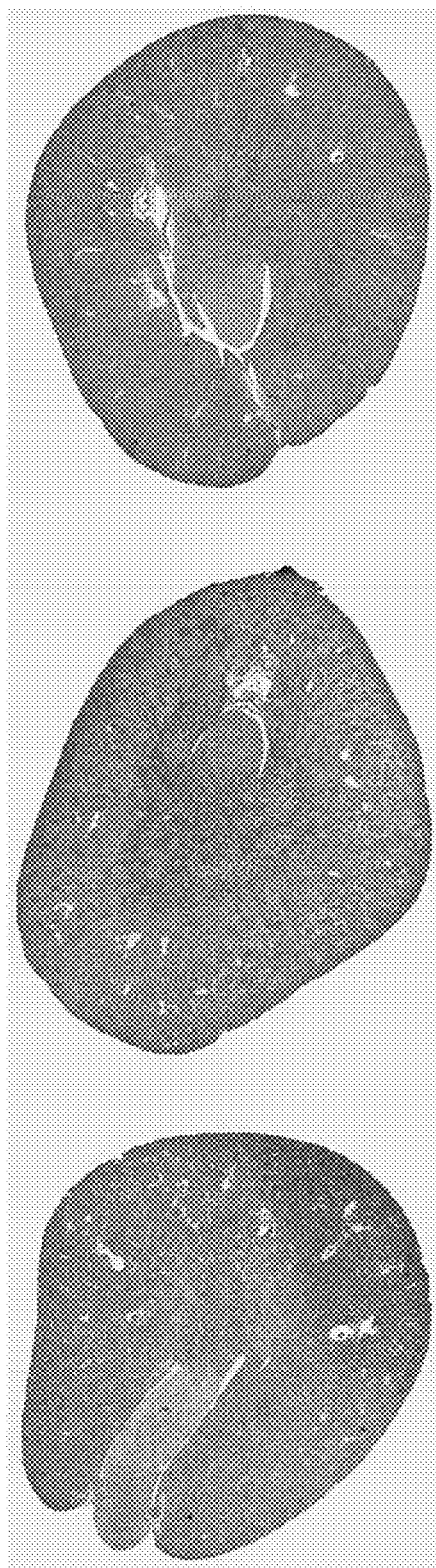

Given the significance of hepcidin-mediated ferroportin regulation in preventing renal IRI, we hypothesized that genetic hepcidin deficiency would aggravate IRI. Here, we demonstrate that hepcidin knock out mice (HAMP$^{-/-}$) develop severe renal injury compared to hepcidin sufficient (WT) controls following IRI. To demonstrate this, we first subjected the HAMP$^{-/-}$ and WT mice to a milder degree of IRI (24 minutes ischemia, 24 hours reperfusion). There was no significant rise in plasma creatinine after mild IRI in the WT mice and sham operated HAMP$^{-/-}$ mice (FIG. 6a). However, the plasma creatinine of HAMP$^{-/-}$ mice subjected to IRI was significantly elevated (FIG. 6a, p<0.0008). Renal histology further corroborated the deleterious effect of hepcidin deficiency in AKI. There were higher numbers of casts and necrotic tubules in the S1, S2 and S3 segments in HAMP$^{-/-}$ kidneys after IRI (FIG. 6b, and Sup FIG. 3b). To investigate if hepcidin re-constitution could rescue HAMP$^{-/-}$ mice from IRI, we injected these mice with a single 50 μg bolus of hepcidin, 24 hours before renal ischemia and sacrificed them 24 hours after reperfusion. Strikingly, a single injection of hepcidin afforded an almost complete protection against IRI in the HAMP$^{-/-}$ mice. Plasma creatinine levels of hepcidin reconstituted HAMP$^{-/-}$ mice were significantly lower compared to untreated mice with levels comparable to that in sham-operated mice (FIG. 6a, p<0.0007). There was also a remarkable preservation of renal histology (FIG. 6c, and Sup FIG. 3c) in the hepcidin treated HAMP$^{-/-}$-IRI mice.

While renal IRI caused a significant increase in NGAL (Sup FIG. 3d, HAMP$^{-/-}$-IRI Vs Sham, p<0.005), hepcidin treatment significantly lowered NGAL expression in HAMP$^{-/-}$-IRI mice compared to untreated HAMP$^{-/-}$-IRI mice (Sup FIG. 3d, HAMP$^{-/-}$-IRI Vs HAMP$^{-/-}$-Hepcidin-IRI, p<0.05).

Figure 6F:
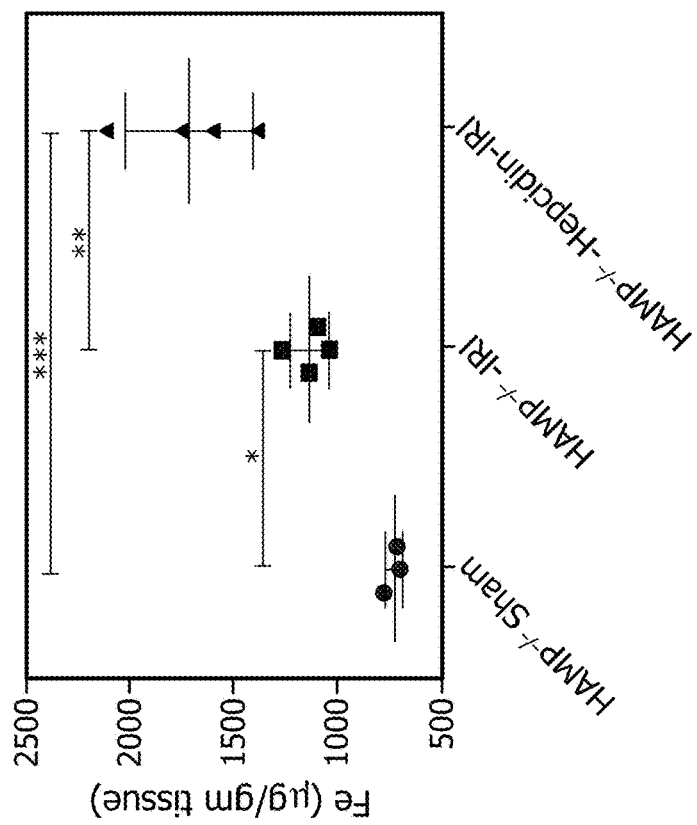
Figure 6E:
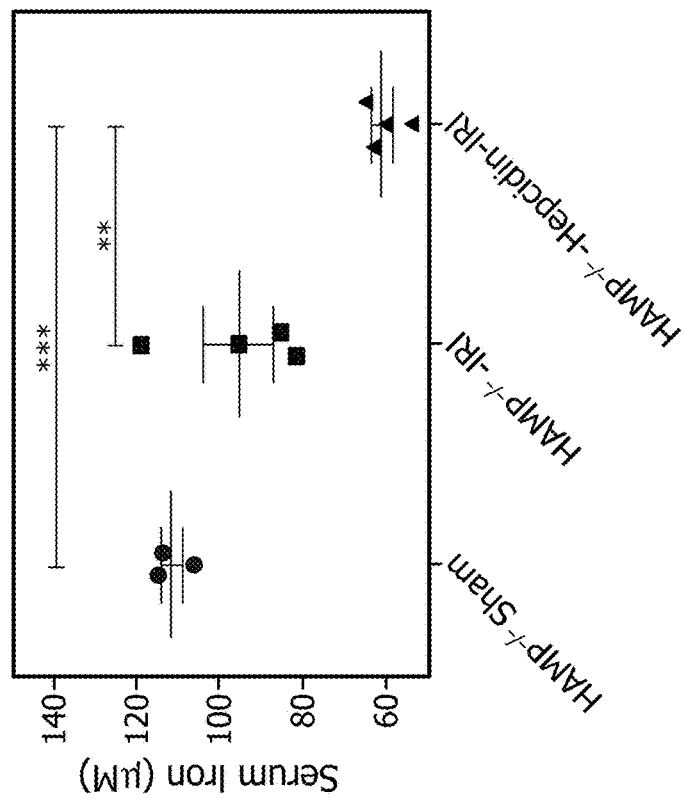

As HAMP-/- mice exhibit chronic iron overload, we investigated if protection induced by reintroduction of hepcidin was associated with changes in systemic iron levels. We measured the serum iron and non-heme iron content in the kidney, spleen and liver of sham, untreated and hepcidin injected HAMP$^{-/-}$ mice after IRI. Compared to sham mice, there was a paradoxic trend toward lowering of serum iron in HAMP$^{-/-}$ mice after IRI, However, hepcidin reintroduction significantly lowered serum iron in HAMP$^{-/-}$-IRI mice compared to both the HAMP-/--IRI and sham mice (FIG. 6e, HAMP$^{-/-}$ -hepcidin-IRI Vs untreated HAMP$^{-/-}$-IRI, p<0.005, HAMP$^{-/-}$-hepcidin-IRI Vs sham, p<0.0005). The lowering of serum iron in hepcidin treated HAMP$^{-/-}$-IRI mice were associated with increased hepatic sequestration of non-heme iron as the liver non-heme iron content of hepcidin-treated HAMP$^{-/-}$-IRI mice was significantly higher than the untreated HAMP$^{-/-}$-IRI mice (FIG. 6f, p<0.005) and sham controls (FIG. 6f, p<0.0005). While Prussian blue staining demonstrated qualitative increases in splenic iron content in hepcidin-treated HAMP$^{-/-}$ mice, we could not detect quantitative differences in the non-heme iron content of the spleen and kidneys of sham, untreated and hepcidin injected HAMP$^{-/-}$ mice after IRI (data not shown). Taken together, our data shows that hepcidin deficiency significantly aggravates kidney's susceptibility to IRI and that reconstitution with exogenous hepcidin and restoration of iron homeostasis can mitigate IRI.

Hepcidin Reconstitution Preserves H-Ferritin and Prevents Apoptosis.

Figure 7A:
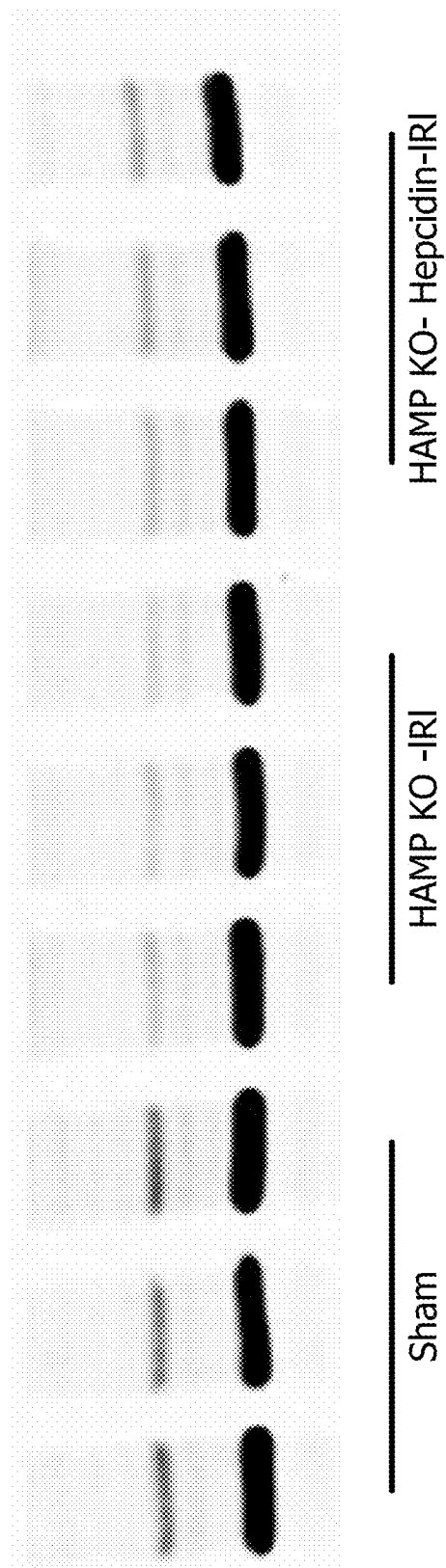
FIG. 7, comprising FIGS. 7a to 7g. Hepcidin treatment mitigates the loss of renal H ferritin and is associated with reduced apoptosis. Expression of H-ferritin in the whole kidney lysates was measured by quantitative Western Blots (a). GAPDH was used to confirm equal protein loading and normalize H ferritin. IRI resulted in a significant reduction in H ferritin in the kidneys of both untreated (○) and Hepcidin treated (▽) HAMP$^{-/-}$ mice as compared to sham (□) HAMP$^{-/-}$ mice (a-b). Hepcidin treated HAMP$^{-/-}$-IRI mice had significantly higher H ferritin levels compared to untreated HAMP$^{-/-}$-IRI mice. *P<0.05, P<0.005, *P<0.0005. Hepcidin reconstitution protects HAMP$^{-/-}$ kidney from IRI induced apoptosis. Hepcidin treated HAMP$^{-/-}$-IRI mice had lower transcriptional activation of pro apoptotic Caspase3 (c) and higher level of anti apoptotic Bcl2 (d). HAMP$^{-/-}$ Sham (●), (■) and HAMP$^{-/-}$-Hepcidin-IRI (▲). n=3-4. *P<0.05, **P<0.005. Data are represented as mean±SEM of $2^{\Delta\Delta CT}$ normalized to GAPDH. TUNEL reactivity was used to assay apoptosis after renal IRI. Sham operated HAMP$^{-/-}$ mice did not show signs of apoptosis (e). Untreated HAMP$^{-/-}$-IRI mice showed severe apoptosis in the cells of the corticomedullar region (f), which was markedly reduced in the Hepcidin treated HAMP$^{-/-}$-IRI mice (g). Representative images from two different experiments with 4-5 mice each are depicted. Magnification (10×).
Figure 7B:
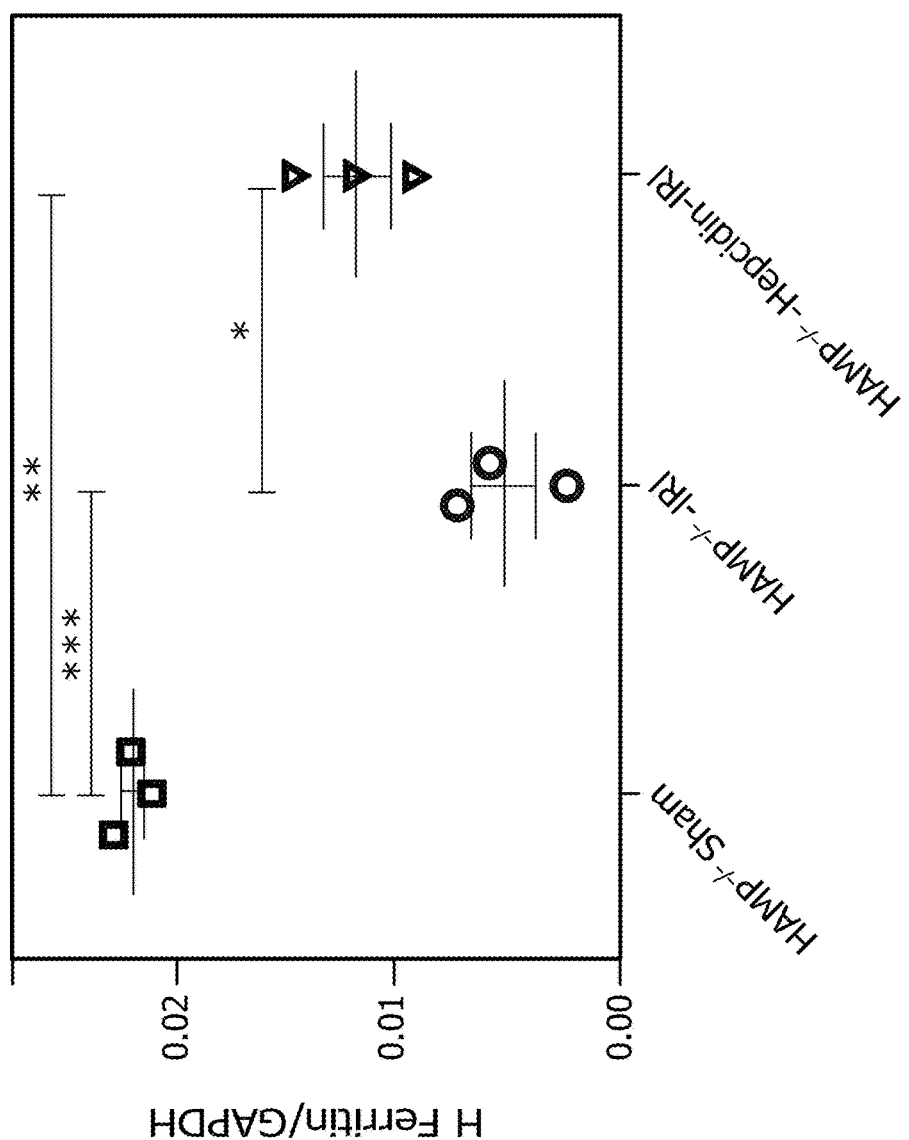
Figure 7D:
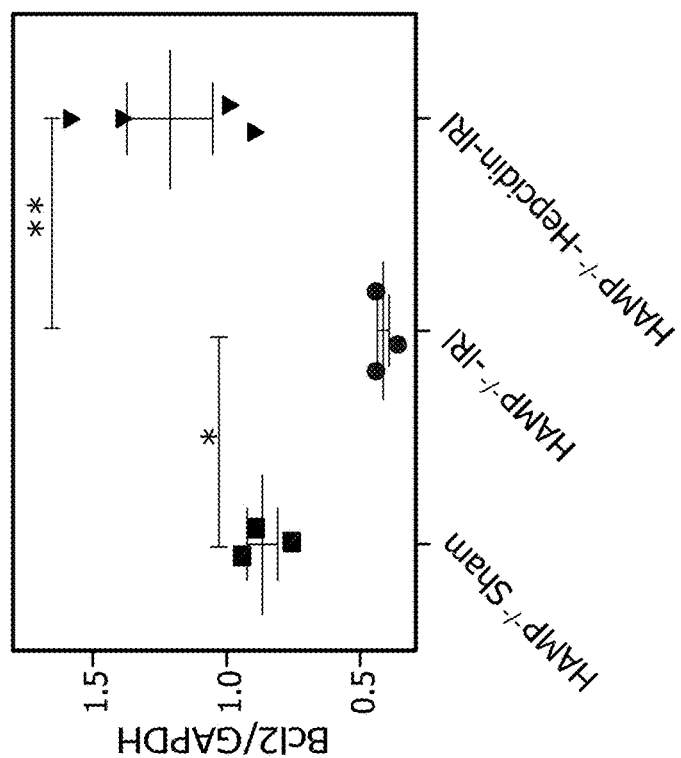
Figure 7C:
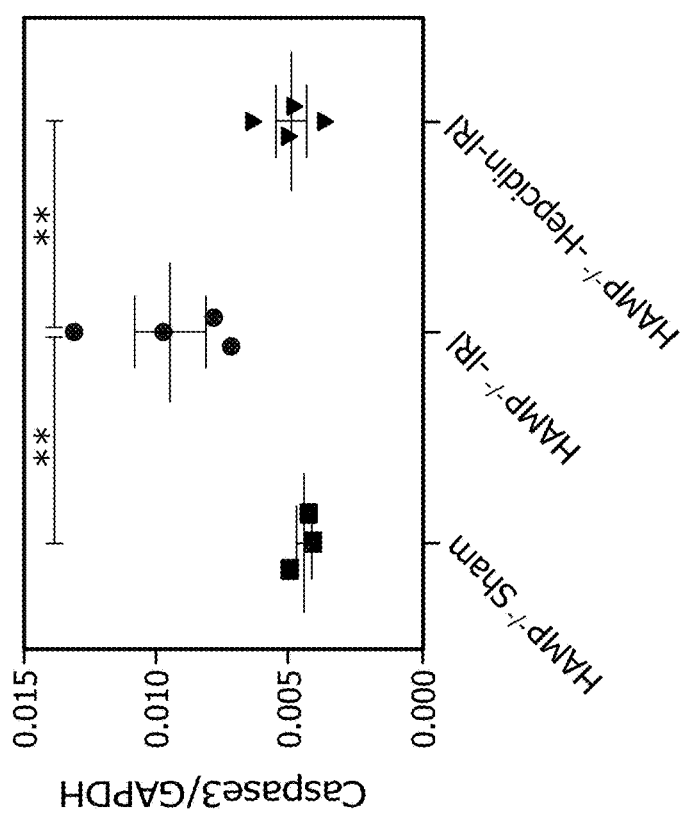
Figure 7E:
Figure 7F:
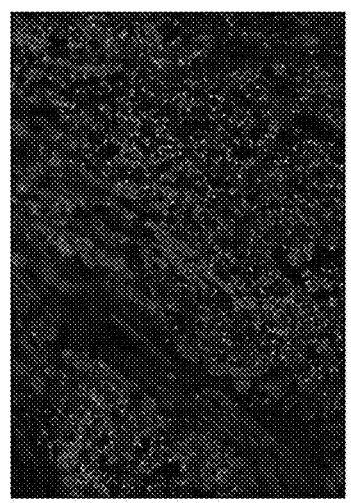
Figure 7G:
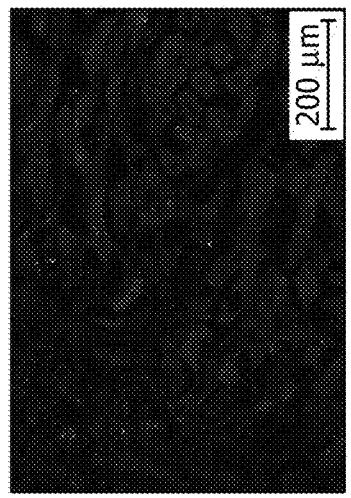

WT mice injected with hepcidin had higher levels of H-Ferritin and less apoptotic kidney injury. To investigate if the kidneys of hepcidin reconstituted HAMP-/mice shared similar features as their WT counterparts after IRI, we quantified H-Ferritin expression by western Blot. We also measured apoptotic pathway markers, Caspase-3 and Bcl-2 expression by RTPCR, and stained the kidneys for TUNEL-positive cells. Consistent with the observation in WT mice, H-Ferritin levels were significantly decreased following IRI in HAMP$^{-/-}$-IRI mice compared to their sham counterparts (FIG. 7a-b, p<0.0005). In contrast, in hepcidin treated HAMP$^{-/-}$-IRI mice, H-Ferritin levels were significantly higher than in untreated HAMP$^{-/-}$-IRI mice (FIG. 7a-b, p<0.05) but lower than in sham mice (FIG. 7a-b, p<0.005). As H-Ferritin is known to exert anti-apoptotic effects under settings of IRI (43), we measured apoptosis related genes and indicators. Caspase-3 was significantly upregulated in the untreated HAMP$^{-/-}$ -IRI mice as compared to sham mice (FIG. 7c, p<0.007). Remarkably, IRI-induced upregulation of Caspase-3 was almost completely prevented by a single injection of hepcidin in HAMP$^{-/-}$-IRI mice with levels comparable to that in sham mice (FIG. 7c, HAMP$^{-/-}$-IRI Vs HAMP$^{-/-}$-Hepcidin-IRI, p<0.007). We also measured the expression of anti-apoptotic gene Bcl-2. Expression of Bcl-2 (d) was significantly lower in the HAMP$^{-/-}$-IRI mice compared to sham mice (FIG. 7d, p<0.05). Hepcidin treatment prevented the decrease in Bcl-2 expression (FIG. 7d, HAMP$^{-/-}$-Hepcidin-IRI Vs HAMP$^{-/-}$-IRI, p<0.005). Corresponding to these changes, in comparison with HAMP$^{-/-}$-IRI mice, there were significantly fewer TUNEL-positive cells in the kidney of hepcidin treated HAMP$^{-/-}$-IRI mice (FIG. 7g, Sup FIG. 4c), especially in the corticomedullary region (FIG. 7e, Sup FIG. 4c). We did not detect any TUNEL positive cells in the kidneys of sham operated HAMP$^{-/-}$ mice (FIG. 7e, Sup FIG. 4a). Collectively, these findings demonstrate that renal IRI in the setting of hepcidin deficiency is associated with worse outcome, is associated with reduction in cytoprotective H-Ferritin, and an increase in epithelial apoptosis. Hepcidin reconstitution preserves H-Ferritin and prevents apoptosis.

Hepcidin Reconstitution Restores Protection Against IRI-Induced Oxidative Stress and Inflammation in HAMP−/− Mice.

Figure 8C:
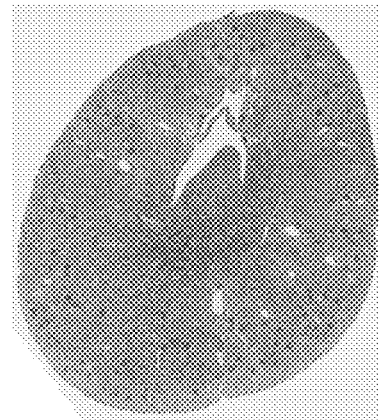
FIG. 8, comprising FIGS. 8a to 8g. Hepcidin reconstitution reduces ROS induced oxidative stress in the kidneys following IRI under settings of hepcidin deficiency and results in reduced infiltration of immune cells. Reactivity to 4 hydroxynonenal (4 HNE) was used as an indicator of oxidative stress in the kidneys of HAMP$^{-/-}$ mice after IRI. Sham operated HAMP$^{-/-}$ mice did not show reactivity to 4HNE (a). Renal IRI in HAMP$^{-/-}$ mice resulted in ROS mediated oxidative stress as observed by strong reactivity to 4HNE especially in the papilla, deep medulla, and corticomedullary region (b). Hepcidin treated HAMP$^{-/-}$-IRI kidneys showed little reactivity to 4 HNE indicative of reduced oxidative stress (c). Representative images from two different experiments with 4-5 mice each are depicted. Magnification: 10×. Immunofluorescence labeling of kidneys showed large infiltration of neutrophils (d, 7/4; green) and CD11b cells (f, CD11b; red) in untreated HAMP$^{-/-}$ IRI mice. In comparison both, neutrophils (e) as well as CD11b cells (g) are dramatically reduced in Hepcidin treated HAMP$^{-/-}$ IRI mice (arrows). Nuclei were stained with DAPI (blue).
Figure 8B:
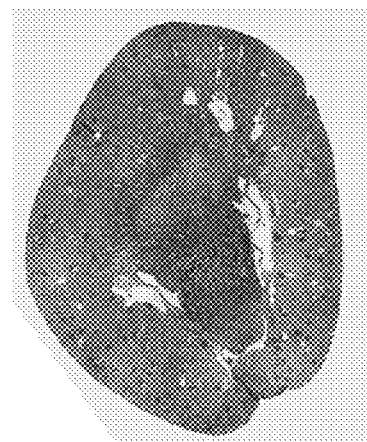
Figure 8A:
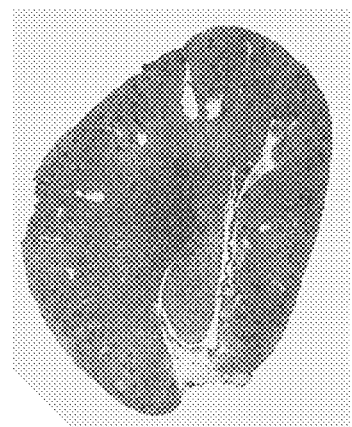

To evaluate the role of ROS in mediating apoptosis in the HAMP$^{-/-}$ mice, we stained the kidneys for 4-HNE immunoreactivity. The kidneys of sham operated HAMP$^{-/-}$ mice did not demonstrate any 4-HNE immunoreactivity (FIG. 8a). In comparison, kidneys of untreated HAMP$^{-/-}$-IRI mice showed high immunoreactivity for 4-HNE adduct (FIG. 8b). 4-HNE staining could be detected in region of the papilla, deep medulla and along the corticomedullary junction. However, hepcidin reconstituted animals demonstrated far less immunoreactivity to 4-HNE, with only a faint speckled pattern observed in the papilla and deep medulla (FIG. 8c). These observations suggest that protection mediated by hepcidin reconstitution in HAMP−/− mice is associated with reduced IR-induced oxidative stress.

Figure 8D:
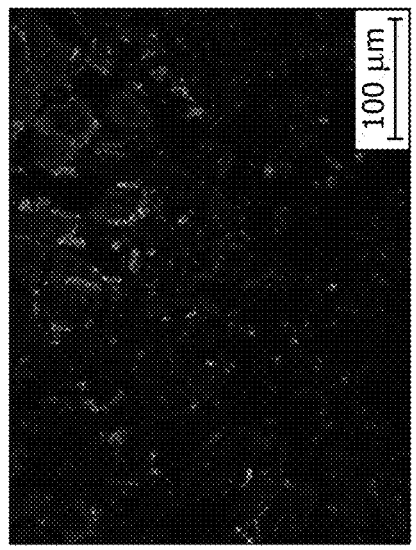
Figure 8E:
Figure 8F:
Figure 8G:
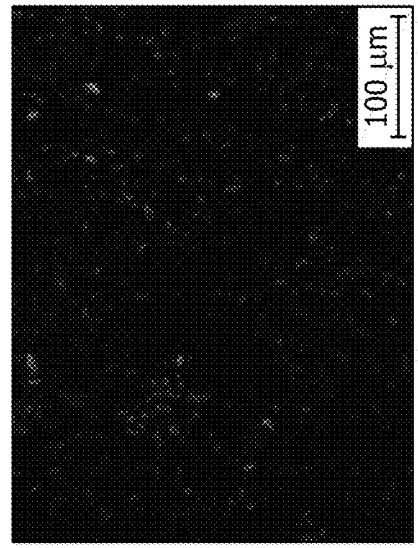

The lack of apoptosis and ROS in hepcidin treated HAMP$^{-/-}$-IRI mice were associated with reduced inflammatory infiltration in the kidneys. Sham operated HAMP$^{-/-}$ mice did not show any neutrophils and CD11b cell infiltration (data not shown). A large number of neutrophils (7/4 antigen positive cells) could be detected in the kidneys of untreated HAMP$^{-/-}$ mice after IRI (FIG. 8d). They were distributed around the injured tubules and in the corticomedullary region. Similarly, there were large numbers of CD11b+ cells surrounding the injured tubules (FIG. 8O. However, hepcidin reconstitution in HAMP$^{-/-}$-IRI mice almost completely prevented kidney injury-associated neutrophil or CD11b cell infiltration (FIGS. 8e and g respectively). The reduction in inflammation correlated well with the lack of apoptosis and ROS in the protected animals.

Hepcidin Prevents IRI-Induced Ferroportin Upregulation and Splenic Iron Depletion.

Figure 9A:
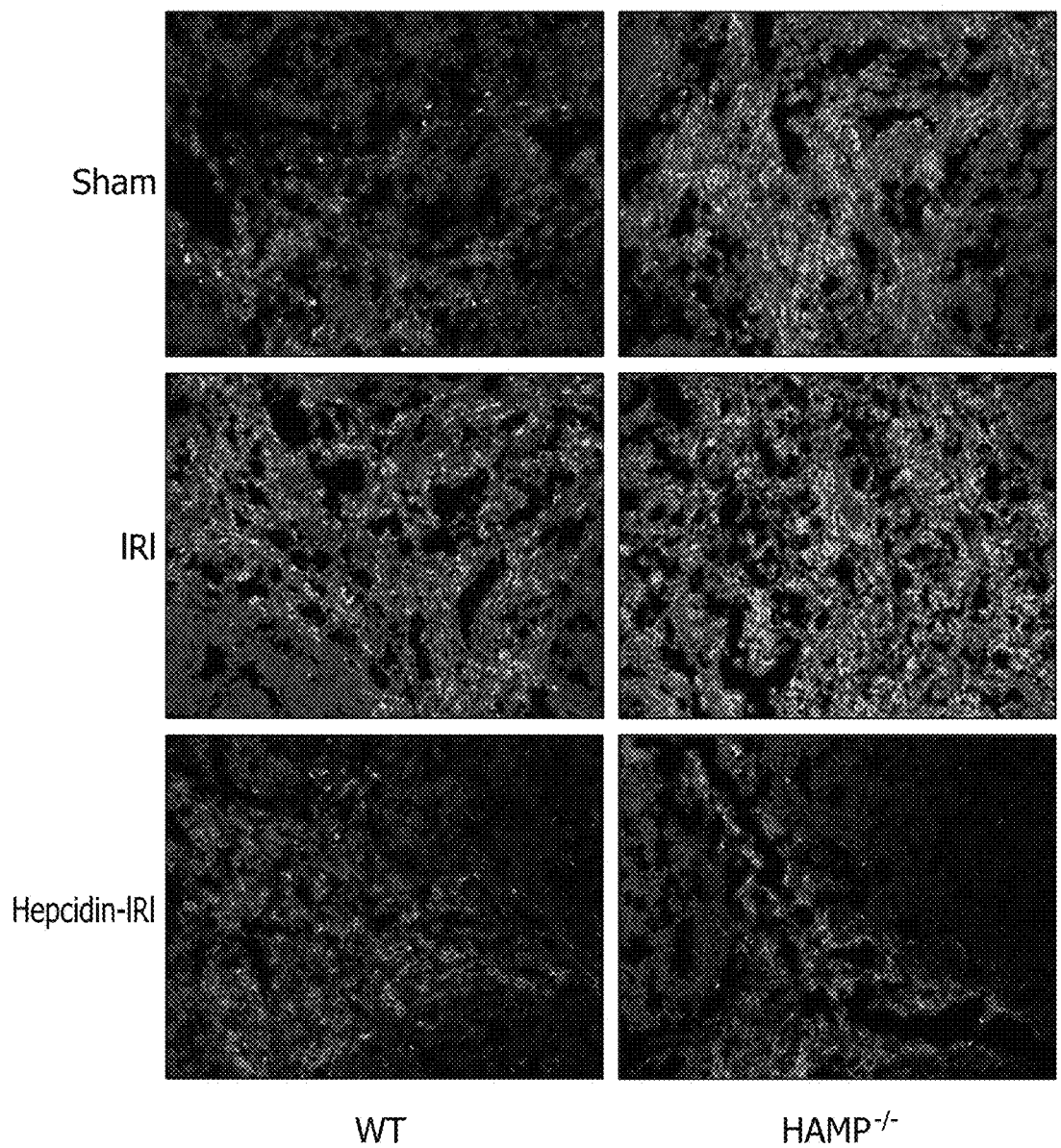
FIG. 9, comprising FIGS. 9a to 9c. Hepcidin treatment prevents renal IRI induced upregulation of splenic ferroportin and increases expression of cytoprotective H Ferritin. Immunofluorescence labeling of spleen, indicated upregulation of ferroportin (green) in the F4/80 macrophages (red) following renal IRI (a, middle panel). Hepcidin treatment resulted in degradation of ferroportin and could be detected in only few scattered F4/80 cells in the red pulp region (a, bottom panel). It can be seen that ferroportin expression is constitutively high is the HAMP$^{-/-}$ mice compared to WT ones (a top panels). Expression of H-ferritin in the spleen lysates was measured by quantitative Western Blots using βActin as the loading control. Hepcidin increased splenic H-Ferritin levels in both (b) WT and (c) HAMP$^{-/-}$ after renal IRI. Representative blots from 3 independent experiments are shown. FIG. b and c: Quantitation of H-ferritin in the spleens of Sham (●), IRI (■) and Hepcidin-IRI (▲) mice respectively was carried out using densitometry software and is expressed as mean±SEM. *P<0.05 (b), **P<0.005 (c).
Figure 9B:
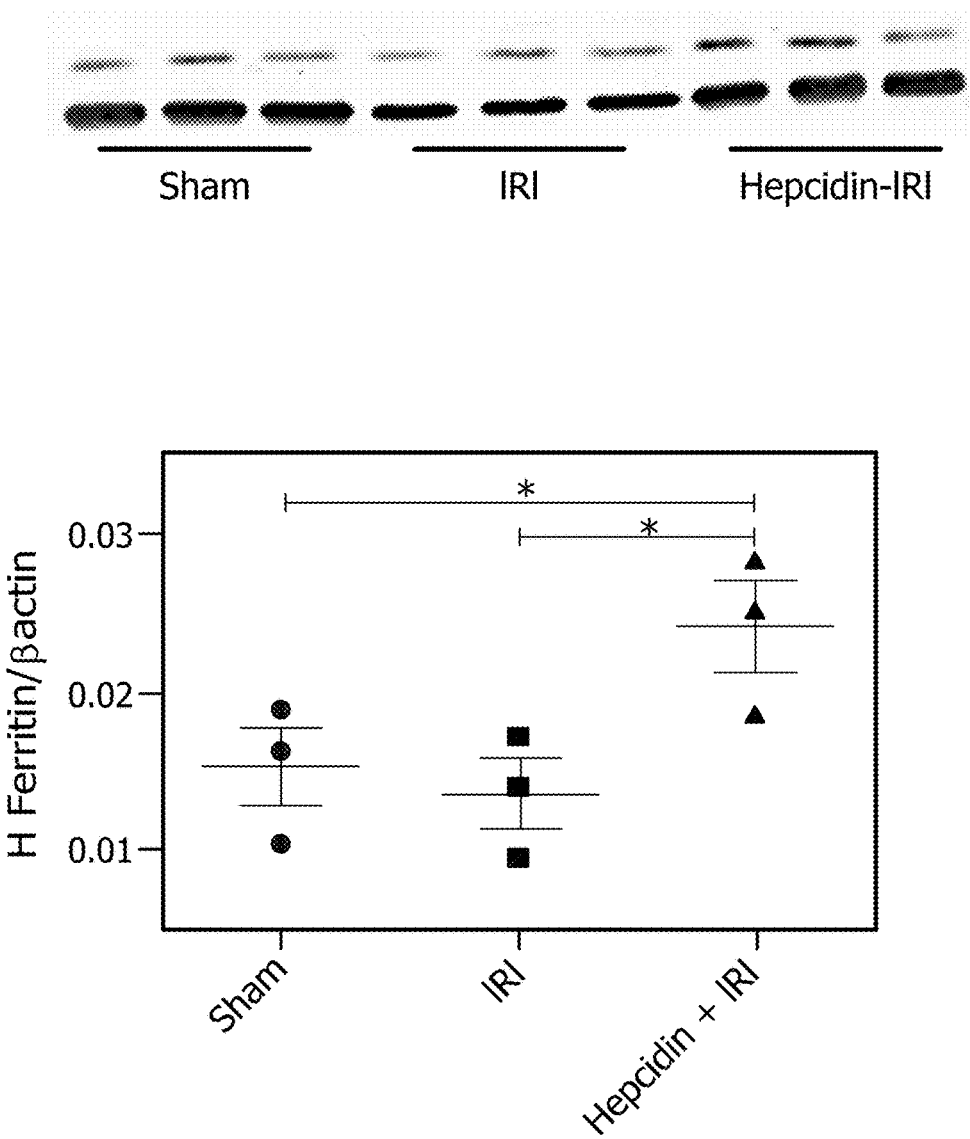
Figure 9C:
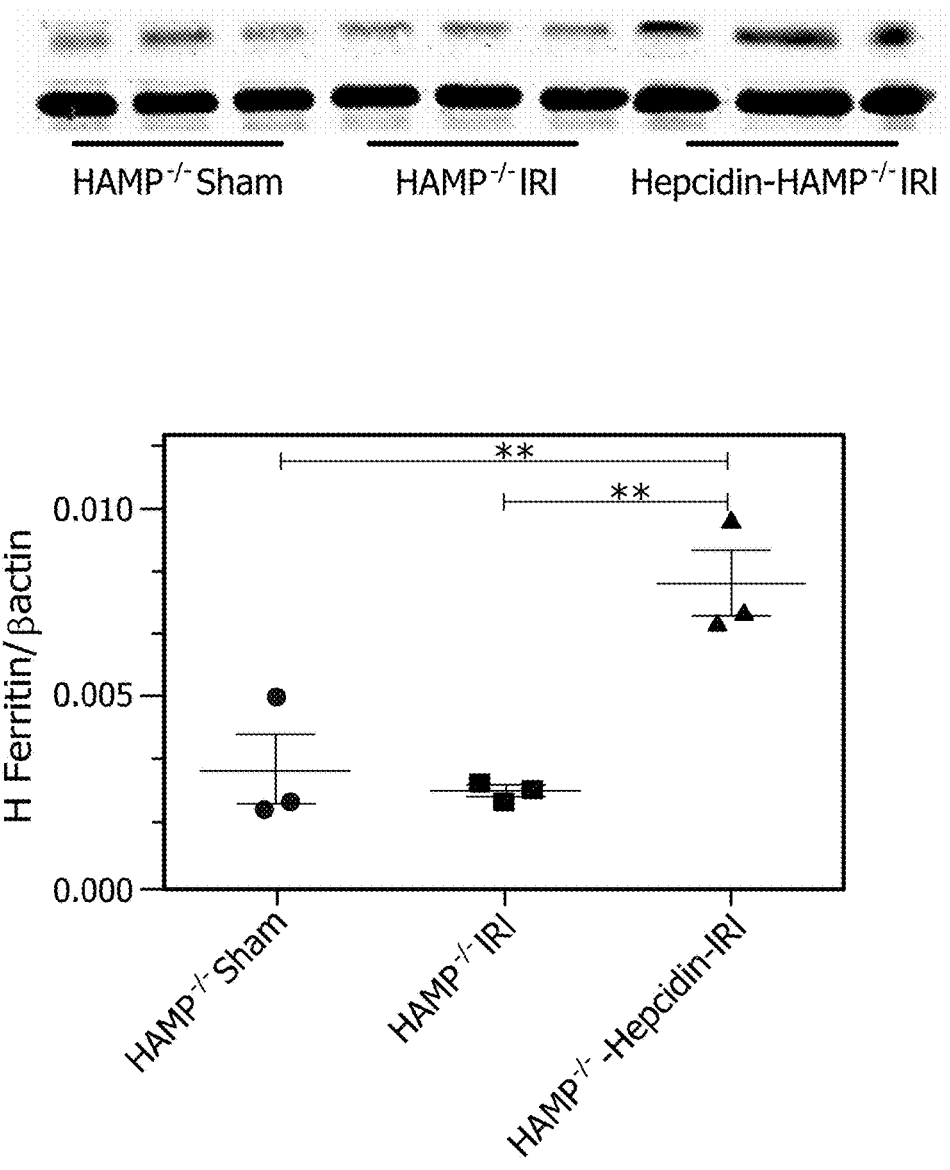

Role of spleen in the pathophysiology of renal IRI is now well established (44). As splenic iron content decreased following renal IRI with an associated increase in serum iron, we stained the spleens of both WT and HAMP$^{-/-}$ mice for ferroportin, the only known iron exporter. Renal IRI resulted in an upregulation of splenic ferroportin in both WT and HAMP$^{-/-}$ mice. Ferroportin expression co-localized mostly with F4/80+ red pulp macrophages (FIG. 9a middle panel). Hepcidin treatment induces a dramatic decrease in surface expression of ferroportin (FIG. 9a bottom panel). In sham operated HAMP$^{-/-}$ mice, because of chronic hepcidin deficiency, basal splenic ferroportin expression was much higher than in the WT mice (FIG. 9a top panel) and as expected, ferroportin expression was not further increased by IRI. Hepcidin reconstitution induced a lower ferroportin expression than sham-operated mice. As hepcidin-induced ferroportin degradation is expected to increase intracellular iron levels, we hypothesized that this would lead to an increase in H-Ferritin synthesis. Indeed, hepcidin-treated IRI mice had significantly higher H-Ferritin compared to both untreated IRI mice and sham controls (FIG. 9b WT hepcidin IRI vs IRI, Hepcidin IRI vs Sham, p<0.05) and (FIG. 9c HAMP$^{-/-}$-Hepcidin-IRI vs HAMP$^{-/-}$-IRI, HAMP$^{-/-}$-Hepcidin-IRI vs HAMP$^{-/-}$ Sham, p<0.005)}. Thus, renal IRI results in an increase in splenic ferroportin expression, and hepcidin treatment prevents IRI-induced ferroportin upregulation. Hepcidin mediated ferroportin degradation leads to splenic iron accumulation and consequent increase in H-Ferritin synthesis (which will reduce free iron levels).

Iron and Hepcidin have Contrasting Effects on Interleukin-6 (IL-6) Production

Interleukin-6 (IL-6) is a pleiotropic cytokine and its signaling pathway have been linked with the pathogenesis of renal IRI (45, 46). To investigate if hepcidin-mediated protection in renal IRI was associated with changes in IL-6, we measured the serum IL-6 levels by ELISA. Compared to sham operated mice, renal IRI resulted in a significant increase in serum IL-6 in both untreated WT (FIG. 10a WT IRI Vs WT Sham, p<0.007) and HAMP$^{-/-}$ mice (FIG. 10b HAMP$^{-/-}$-IRI Vs HAMP$^{-/-}$ Sham, p<0.05). Hepcidin treatment prevented IRI-induced increase in IL-6 levels in both WT (FIG. 10a WT-IRI Vs WT Hepcidin-IRI, p<0.007) and HAMP$^{-/-}$ mice (FIG. 10b HAMP$^{-/-}$-IRI Vs HAMP$^{-/-}$-Hepcidin-IRI, p<0.05), with levels comparable to those in sham-operated mice. To explore the possibility that free iron might directly regulate IL-6 production in immune cells, we treated splenocytes from WT mice with ferrous sulfate and measured the IL-6 secretion into supernatants by ELISA. Untreated splenocytes and hepcidin-treated splenocytes were used as controls. There was no significant difference in IL-6 levels between the untreated splenocytes and hepcidin-treated cells (FIG. 10c). However treatment with iron significantly increased splenocytes IL-6 secretion compared to both untreated and hepcidin-treated cells (FIG. 10c, p<0.005). These findings demonstrate that excess splenocyte free iron leads to increased production of IL-6, a cytokine implicated in the pathogenesis of renal IRI.

Minihepcidin (PR-73) prevents AKI following IRI.

Animals were subjected to IRI with or without treatment with the hepcidin agonist at 100 or 200 nmol. The effects at 200 nmol are statistically significant in reducing plasma creatinine levels relative to the other groups.

DISCUSSION

In this study, we demonstrate that supplementing mice with exogenous hepcidin protects the kidney from IRI as manifested by an improved renal structure and function. First, we present evidence that renal IRI results in a systemic iron mobilization from the hepatosplenic compartments and is associated with kidney iron accumulation. Hepcidin treatment prevents IRI-induced iron dyshomeostasis by inducing ferroportin degradation, H-Ferritin induction and effective hepatosplenic sequestration of iron. These effects are associated with reduced ROS, apoptosis and inflammation in the kidney. We also provide evidence that genetic hepcidin deficiency severely increases susceptibility to renal IRI and that hepcidin reconstitution restores protection. Lastly, our in-vitro data provides evidence for additional mechanisms of hepcidin's protective effects: 1) a direct anti-apoptotic effect of hepcidin on renal epithelial cells and 2) an anti-inflammatory effect to counter iron-induced IL-6 production in resting splenocytes.

The implication of iron in pathogenesis of AKI in absence of systemic iron overload is a new and expanding field. Iron plays a fundamental pathological role in IRI and iron chelation with desferrioxamine has been reported to provide protection and significantly improve its severity and outcomes (7, 37). The beneficial effect of iron-chelating agents against renal IRI may be a result of binding (and, thereby removal) of iron from both intra and extracellular space (37, 47), and in the case of apotransferrin (15) and in the case of NGAL (48), the delivery of iron to viable cells to enhance recovery. Our current findings not only corroborate the role of iron in IRI but also indicate the importance of extra-renal iron homeostasis in renal pathophysiology.

The protective property of H-Ferritin is well established in AKI as was elegantly by a recent study that demonstrated worse outcome of AKI following deletion of H-Ferritin from renal proximal tubules (49). Anti-apoptotic property of H-Ferritin has also been demonstrated in a liver ischemia model, where H-Ferritin was shown to suppress the activation of the transcription factor NFκB in a HO-1 independent manner as well as to have a direct anti-apoptotic effect on hepatocytes (43). Each molecule of H-Ferritin can to bind to 4500 $Fe^{2+}$ ions (50) making it an important endogenous iron chelator. This sequestration of $Fe^{2+}$ by H-Ferritin prevents it from participating in the Fenton reaction and thus inhibits iron-mediated pro-oxidant activity. The reduction in ROS and hence apoptosis has been attributed to reduced availability of iron following IRI (7, 8-17-18). In our study, hepcidin treatment increased renal H-Ferritin levels after IRI. Hepcidin also preserved kidney H-Ferritin in $HAMP^{-/-}$ animals. Thus, by limiting the availability of free intracellular iron in the renal cells, H-Ferritin could potentially reduce renal ROS and ensuing apoptosis. Actions of hepcidin on the spleen are equally if not more important due to its large iron content. Hepcidin induced splenic ferroportin degradation, causing splenic iron sequestration and H-Ferritin induction after renal IRI. It can thus be argued that reduced splenic ferroportin and increased splenic H-Ferritin prevented systemic iron mobilization following IRI and limited its availability to catalyze ROS production in the kidney and prevent tissue injury. A direct anti-apoptotic role of hepcidin on renal epithelial cells as observed in our in-vitro hypoxia-reoxygenation studies is likely to serve as an additional protective mechanism. Additional studies are required to define the mechanisms of hepcidin's anti-apoptotic effects.

Recent studies have suggested an important role for liver and spleen (51, 44) in the pathophysiology of renal IRI. In this study, we demonstrate that IRI induces hepatosplenic iron export, which likely contributes to the pathogenesis of renal IRI. This is not surprising as splenic macrophages along with hepatocytes are the main storage sites and sources of iron in the body (52). Because hepcidin acts rapidly on the splenic macrophages (53), under our experimental conditions, contributions from the spleen are likely to be more critical. The ability of spleen to sequester iron has been observed in LPS-induced inflammation (54). It was also demonstrated that following endotoxemia and inflammation, hepatic hepcidin production increases. A model of liver IRI similarly showed that serum and hepatic hepcidin increases after IRI (55). Our observation that renal IRI induces hepatic hepcidin expression to increase serum levels further confirms these studies. Thus, under settings of both sterile (IRI) and non-sterile acute inflammation, body's physiological response seems to induce hepcidin-dependent intracellular iron sequestration to protect the organism from free iron-mediated injury. Paradoxic increase in splenic ferroportin despite an increase in hepcidin levels after IRI needs further study. It could be mediated by signals from the injured kidney independent of hepcidin.

Our data in the $HAMP^{-/-}$ mice does not completely mimic the findings in WT mice, where the serum iron levels actually decreased and liver levels increased after renal IRI. However, it should be noted that this is a model of constitutive iron overload and spleens of $HAMP^{-/-}$ mice express high levels of cell surface ferroportin and are severely iron depleted even under normal conditions (56). Therefore, unlike WT mice, where spleen contributes significantly to systemic iron mobilization after IRI, a similar phenomenon is not observed in the $HAMP^{-/-}$ mice. Increased hepatic non-heme iron in $HAMP^{-/-}$ mice following IRI suggests hepcidin-independent mechanisms and needs further study.

CD45+ immune cells start infiltrating the kidney early after reperfusion, with neutrophils playing a major role in the ensuing pathological response (6, 41). Hepcidin treatment reduced the infiltration of total CD45+ cells majority of which were neutrophils. Whether hepcidin affects the chemotaxis of immune cells to the kidney or the reduction in infiltration is a consequence of less epithelial injury needs further investigation. Examining early events preceding the infiltration of cells may provide clues to this question and warrant further investigation.

Inflammatory cytokines such as IL-6 have been shown to be deleterious on the outcome of renal IRI (45, 46) and are made locally as well as by infiltrating macrophages (57). Interestingly, IL-6 is also a powerful inducer of hepcidin (58). Hepcidin treatment significantly prevented IRI-induced increase in splenic, renal, and systemic IL-6 levels. The source of systemic IL-6 was not investigated in this study. As systemic iron levels are increased after renal IRI, we examined whether iron could directly regulate IL-6 production. Our in-vitro data suggests that iron-dependent increase in splenic IL-6 secretion could be an important source. Our in-vitro observations are consistent with findings by Domenico et al. (59) who showed that hepcidin pretreatment of iron loaded bone marrow macrophages reduced LPS-induced IL-6 and TNF alpha production. Collectively, our observations suggest that renal IRI-induced reduction in splenic H-Ferritin and increase in free iron could induce splenocytes to secrete IL-6.

Our studies demonstrate a novel renal protective effect of hepcidin. We propose that hepcidin protects the kidney from IRI by acting not only on the renal epithelial cells but also through its effects on extra-renal iron homeostasis, with spleen being a dominant player. Hepcidin's protection is achieved mainly by inducing ferroportin degradation and subsequent induction of H-Ferritin, which would lead to a safe sequestration of free iron. Further studies are required to investigate the relative contribution of renal and extrarenal ferroportin in mediating hepcidin's protective effects. The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Bagshaw S M. The long-term outcome after acute renal failure. Current opinion in critical care. 2006; 12(6):561-6.
2. Korkeila M, Ruokonen E, and Takala J. Costs of care, long-term prognosis and quality of life in patients requir- 3. Devarajan P. Cellular and molecular derangements in acute tubular necrosis. Current opinion in pediatrics. 2005; 17(2):193-9.
4. Dagher P C, Herget-Rosenthal S, Ruehm S G, Jo S K, Star R A, Agarwal R, and Molitoris B A. Newly developed techniques to study and diagnose acute renal failure. Journal of the American Society of Nephrology: JASN. 2003; 14(8):2188-98.
5. Li C, and Jackson R M. Reactive species mechanisms of cellular hypoxia-reoxygenation injury. American journal of physiology Cell physiology. 2002; 282(2):C227-41.
6. Friedewald J J, and Rabb H. Inflammatory cells in ischemic acute renal failure. Kidney international. 2004; 66(2):486-91.
7. Baliga R, Ueda N, and Shah S V. Increase in bleomycin-detectable iron in ischaemia/reperfusion injury to rat kidneys. The Biochemical journal. 1993; 291 (Pt 3)(901-5.
8. Voogd A, Sluiter W, van Eijk H G, and Koster J F. Low molecular weight iron and the oxygen paradox in isolated rat hearts. The Journal of clinical investigation. 1992; 90(5):2050-5.
9. Castaneda M P, Swiatecka-Urban A, Mitsnefes M M, Feuerstein D, Kaskel F J, Tellis V, and Devarajan P. Activation of mitochondrial apoptotic pathways in human renal allografts after ischemiareperfusion injury. Transplantation. 2003; 76(1):50-4.
10. Hirakawa A, Takeyama N, Nakatani T, and Tanaka T. Mitochondrial permeability transition and cytochrome c release in ischemia-reperfusion injury of the rat liver. The Journal of surgical research. 2003; 111(2):240-7.
11. Aroun A, Zhong J L, Tyrrell R M, and Pourzand C. Iron, oxidative stress and the example of solar ultraviolet A radiation. Photochemical & photobiological sciences 2012; 11(1):118-34.
12. Baliga R, Zhang Z, Baliga M, Ueda N, and Shah S V. Role of cytochrome P-450 as a source of catalytic iron in cisplatin-induced nephrotoxicity. Kidney international. 1998; 54(5):1562-9.
13. Zhang W, Wang M, Xie H Y, Zhou L, Meng X Q, Shi J, and Zheng S. Role of reactive oxygen species in mediating hepatic ischemia-reperfusion injury and its therapeutic applications in liver transplantation. Transplantation proceedings. 2007; 39(5):1332-7.
14. Himmelfarb J, McMonagle E, Freedman S, Klenzak J, McMenamin E, Le P, Pupim L B, Ikizler T A, and The P G. Oxidative stress is increased in critically ill patients with acute renal failure. Journal of the American Society of Nephrology: JASN. 2004; 15(9):2449-56.
15. de Vries B, Walter S J, von Bonsdorff L, Wolfs T G, van Heurn L W, Parkkinen J, and Buurman W A. Reduction of circulating redox-active iron by apotransferrin protects against renal ischemia-reperfusion injury. Transplantation. 2004; 77(5):669-75.
16. Baliga R, Zhang Z, Baliga M, and Shah S V. Evidence for cytochrome P-450 as a source of catalytic iron in myoglobinuric acute renal failure. Kidney international. 1996; 49(2):362-9.
17. Baliga R, Zhang Z, Baliga M, Ueda N, and Shah S V. In vitro and in vivo evidence suggesting a role for iron in cisplatin-induced nephrotoxicity. Kidney international. 1998; 53(2):394-401.
18. Zager R A. Combined mannitol and deferoxamine therapy for myohemoglobinuric renal injury and oxidant tubular stress. Mechanistic and therapeutic implications. The Journal of clinical investigation. 1992; 90(3):711-9.
19. Paller M S. Hemoglobin- and myoglobin-induced acute renal failure in rats: role of iron in nephrotoxicity. The American journal of physiology. 1988; 255(3 Pt 2):F539-44.
20. Montalbetti N, Simonin A, Kovacs G, and Hediger M A. Mammalian iron transporters: families SLC11 and SLC40. Molecular aspects of medicine. 2013; 34(2-3):270-87.
21. Abboud S, and Haile D J. A novel mammalian iron-regulated protein involved in intracellular iron metabolism. J Biol Chem. 2000; 275(26):19906-12.
22. De Domenico I, Ward D M, Langelier C, Vaughn M B, Nemeth E, Sundquist W I, Ganz T, Musci G, and Kaplan J. The molecular mechanism of hepcidin-mediated ferroportin down-regulation. Molecular biology of the cell. 2007; 18(7):2569-78.
23. Moulouel B, Houamel D, Delaby C, Tchernitchko D, Vaulont S, Letteron P, Thibaudeau O, Puy H, Gouya L, Beaumont C, et al. Hepcidin regulates intrarenal iron handling at the distal nephron. Kidney international. 2013; 84(4):756-66.
24. Park C H, Valore E V, Waring A J, and Ganz T. Hepcidin, a urinary antimicrobial peptide synthesized in the liver. J Biol Chem. 2001; 276(11):7806-10.
25. Nemeth E, Tuttle M S, Powelson J, Vaughn M B, Donovan A, Ward D M, Ganz T, and Kaplan J. Hepcidin regulates cellular iron efflux by binding to ferroportin and inducing its internalization. Science. 2004; 306(5704):2090-3.
26. Nemeth E. Targeting the hepcidin-ferroportin axis in the diagnosis and treatment of anemias. Advances in hematology. 2010; 2010(750643.
27. De Domenico I, Ward D M, and Kaplan J. Hepcidin regulation: ironing out the details. The Journal of clinical investigation. 2007; 117(7):1755-8.
28. Izawa T, Murakami H, Wijesundera K K, Golbar H M, Kuwamura M, and Yamate J. Inflammatory regulation of iron metabolism during thioacetamide-induced acute liver injury in rats. Experimental and toxicologic pathology: official journal of the Gesellschaft fur Toxikologische Pathologie. 2014; 66(2-3):155-62.
29. Maisetta G, Vitali A, Scorciapino M A, Rinaldi A C, Petruzzelli R, Brancatisano F L, Esin S, Stringaro A, Colone M, Luzi C, et al. pH-dependent disruption of *Escherichia coli* ATCC 25922 and model membranes by the human antimicrobial peptides hepcidin 20 and 25. The FEBS journal. 2013; 280(12):2842-54.
30. Kroot, J. J. C., Tjalsma, H., Fleming, R. E. & Swinkels, D. W. Hepcidin in human iron disorders: diagnostic implications. Clin. Chem. 57, 1650-1669 (2011).
31. Liu Q, Davidoff O, Niss K, and Haase V H. Hypoxia-inducible factor regulates hepcidin via erythropoietin-induced erythropoiesis. The Journal of clinical investigation. 2012; 122(12):4635-44.
32. Ho J, Reslerova M, Gali B, Gao A, Bestland J, Rush D N, Nickerson P W, and Rigatto C. Urinary hepcidin-25 and risk of acute kidney injury following cardiopulmonary bypass. Clinical journal of the American Society of Nephrology: CJASN. 2011; 6(10):2340-6.
33. Havasi A, and Borkan S C. Apoptosis and acute kidney injury. Kidney international. 2011; 80(1):29-40.
34. Ernest S, and Bello-Reuss E. Expression and function of P-glycoprotein in a mouse kidney cell line. The American journal of physiology. 1995; 269(2 Pt 1):C323-33.

35. Liang H L, Hilton G, Mortensen J, Regner K, Johnson C P, and Nilakantan V. MnTMPyP, a cell-permeant SOD mimetic, reduces oxidative stress and apoptosis following renal ischemia-reperfusion. American journal of physiology Renal physiology. 2009; 296(2):F266-76.

36. Chien C T, Chang T C, Tsai C Y, Shyue S K, and Lai M K. Adenovirus-mediated bcl-2 gene transfer inhibits renal ischemia/reperfusion induced tubular oxidative stress and apoptosis. American journal of transplantation: official journal of the American Society of Transplantation and the American Society of Transplant Surgeons. 2005; 5(6): 1194-203.

37. Huang H, He Z, Roberts L J, 2nd, and Salahudeen A K. Deferoxamine reduces cold-ischemic renal injury in a syngeneic kidney transplant model. American journal of transplantation 2003; 3(12):1531-7.

38. Arkadopoulos N, Nastos C, Kalimeris K, Economou E, Theodoraki K, Kouskouni E, Pafiti A, Kostopanagiotou G, and Smyrniotis V. Iron chelation for amelioration of liver ischemia-reperfusion injury. Hemoglobin. 2010; 34(3):265-77.

39. Schneider M P, Sullivan J C, Wach P F, Boesen E I, Yamamoto T, Fukai T, Harrison D G, Pollock D M, and Pollock J S. Protective role of extracellular superoxide dismutase in renal ischemia/reperfusion injury. Kidney international. 2010; 78(4):374-81.

40. Liu W, Kato M, Akhand A A, Hayakawa A, Suzuki H, Miyata T, Kurokawa K, Hotta Y, Ishikawa N, and Nakashima I. 4-hydroxynonenal induces a cellular redox status-related activation of the caspase cascade for apoptotic cell death. Journal of cell science. 2000; 113 (Pt 4)(635-41.

41. Chaturvedi S, Yuen D A, Bajwa A, Huang Y W, Sokollik C, Huang L, Lam G Y, Tole S, Liu G Y, Pan J, et al. Slit2 prevents neutrophil recruitment and renal ischemia-reperfusion injury. Journal of the American Society of Nephrology: JASN. 2013; 24(8):1274-87.

42. Kinsey G R, Li L, and Okusa M D. Inflammation in acute kidney injury. Nephron Experimental nephrology. 2008; 109(4):e102-7.

43. Berberat P O, Katori M, Kaczmarek E, Anselmo D, Lassman C, Ke B, Shen X, Busuttil R W, Yamashita K, Csizmadia E, et al. Heavy chain ferritin acts as an antiapoptotic gene that protects livers from ischemia reperfusion injury. FASEB journal: official publication of the Federation of American Societies for Experimental Biology. 2003; 17(12):1724-6.

44. Gigliotti J C, Huang L, Ye H, Bajwa A, Chattrabhuti K, Lee S, Klibanov A L, Kalantari K, Rosin D L, and Okusa M D. Ultrasound prevents renal ischemia-reperfusion injury by stimulating the splenic cholinergic anti-inflammatory pathway. Journal of the American Society of Nephrology: JASN. 2013; 24(9):1451-60.

45. Kielar M L, John R, Bennett M, Richardson J A, Shelton J M, Chen L, Jeyarajah D R, Zhou X J, Zhou H, Chiquett B, et al. Maladaptive role of IL-6 in ischemic acute renal failure. Journal of the American Society of Nephrology: JASN. 2005; 16(11):3315-25.

46. Nechemia-Arbely Y, Barkan D, Pizov G, Shriki A, Rose-John S, Galun E, and Axelrod J H. IL-6/IL-6R axis plays a critical role in acute kidney injury. Journal of the American Society of Nephrology: JASN. 2008; 19(6):1106-15.

47. Paller, M. S. & Hedlund, B. E. Extracellular iron chelators protect kidney cells from hypoxia/reoxygenation. Free Radic. Biol. Med. 17, 597-603 (1994).

48. Mishra, J. et al. Amelioration of ischemic acute renal injury by neutrophil gelatinase-associated lipocalin. J. Am. Soc. Nephrol. 15, 3073-3082 (2004).

49. J Clin Invest. Oct. 1, 2013; 123(10): 4423-4434. Proximal tubule H-ferritin mediates iron trafficking in acute kidney injury Abolfazl Zarjou, Subhashini Bolisetty, Reny Joseph, Amie Traylor, Eugene O. Apostolov, Paolo Arosio, Jozsef Balla, Jill Verlander, Deepak Darshan, Lukas C. Kuhn, and Anupam Agarwal.

50. Proc Biol Sci. 1991 Jun. 22; 244(1311):211-7. Iron (III) can be transferred between ferritin molecules. Bauminger E R, Harrison P M, Hechel D, Nowik I, Treffry A 51. Golab F, Kadkhodaee M, Zahmatkesh M, Hedayati M, Arab H, Schuster R, et al. Ischemic and non-ischemic acute kidney injury cause hepatic damage. Kidney Int. 2009; 75:783-792

52. J Innate Immun. 2012; 4(5-6):446-53. Macrophages and systemic iron homeostasis. Ganz T.

53. Chaston T, Chung B, Mascarenhas M, Marks J, Patel B, Srai S K, Sharp P. Evidence for differential effects of hepcidin in macrophages and intestinal epithelial cells. Gut. 2008; 57:374-82

54. J Biol Chem. 2002 Oct. 18; 277(42):39786-91. Regulation of reticuloendothelial iron transporter MTP1 (Slc11a3) by inflammation. Yang F, Liu X B, Quinones M, Melby P C, Ghio A, Haile D J.

55. Liver Transpl. 2005 July; 11(7):800-6. Ischemia-reperfusion of rat liver modulates hepcidin in vivo expression. Goss J A, Seu P, Gao F Q, Wyllie S.

56. Proc Natl Acad Sci USA. 2001 Jul. 17; 98(15):8780-5. Lack of hepcidin gene expression and severe tissue iron overload in upstream stimulatory factor 2 (USF2) knockout mice. Nicolas G, Bennoun M, Devaux I, Beaumont C, Grandchamp B, Kahn A, Vaulont S.

57. Mediators of inflammation in acute kidney injury. Akcay A, Nguyen Q, Edelstein C L. Mediators Inflamm. 2009; 2009:137072.

58. Blood. 2006 Nov. 1; 108(9):3204-9. Interleukin-6 induces hepcidin expression through STAT3. Wrighting D M, Andrews N C.

59. J Clin Invest. 2010 July; 120(7):2395-405. Hepcidin mediates transcriptional changes that modulate acute cytokine-induced inflammatory responses in mice. De Domenico I, Zhang T Y, Koening C L, Branch R W, London N, Lo E, Daynes R A, Kushner J P, Li D, Ward D M, Kaplan J.

60. Ruchala and Nemeth, 2014, Trends in Pharmacological Sciences, 35:3:155. The pathophysiology and pharmacology of hepcidin.

61. Ganz et al., International Pat. Pub. WO2013086143 A1.

62. Young et al., Antioxid Redox Signal, 2014, 20:8:1181 (epub. Sep. 17, 2013).

63. Gaun et al., Blood Cells Mol. Diseases, 2014; Available online 4 Jul. 2014,

What is claimed is:

1. A method for preventing or treating renal ischemia reperfusion injury or acute kidney injury associated with renal ischemia reperfusion injury, said method comprising administering to a subject in need thereof a pharmaceutical composition comprising an effective amount of hepcidin or a biologically active fragment or homolog thereof, wherein said hepcidin or biologically active fragment or homolog thereof comprises a sequence selected from the group consisting of SEQ ID NOs:1, 2, 3, 4, and 5, thereby preventing or treating renal ischemia reperfusion injury or acute kidney injury associated with renal ischemia reperfusion injury.

2. The method of claim 1, wherein said method prevents or treats acute kidney injury associated with renal ischemia reperfusion injury.

3. The method of claim 1, wherein said method elicits an effect selected from the group consisting of preventing or treating oxidative stress associated injury in the kidney, inhibiting increased serum iron levels associated with ischemia reperfusion injury, inhibiting kidney iron accumulation, stimulating an increase in splenic non-heme iron levels, inhibiting a decrease in liver non-heme iron, inhibiting increased hepcidin gene expression, inhibiting increased endogenous serum hepcidin levels, inhibiting increased plasma creatinine levels, inhibiting kidney tubular necrosis, inhibiting renal epithelial apoptosis, inhibiting oxidative stress, inhibiting inflammation, inhibiting infiltration of immune cells into the kidney, preventing or inhibiting an increase in ischemia reperfusion-injury-induced renal ferroportin levels, inhibiting a decrease in H-ferritin levels, inhibiting infiltration of neutrophils and CD11b cells into the kidney, inhibiting splenic iron release, stimulating an increase in H-ferritin levels, and inhibiting increases in interleukin-6 (IL-6) levels.

4. The method of claim 1, wherein said hepcidin is administered at a dosage ranging from about 0.1 milligram/kilogram body weight (mg/kg body wt.) to about 100 mg/kg body wt.

5. The method of claim 4, wherein said dosage is from about 1 mg/kg body wt. to about 10 mg/kg body wt.

6. The method of claim 5, wherein said dosage is selected from the group consisting of about 1.0, 1.5, 1.67, 2.0, 2.5, 3.0, 3.33, 4.0, 4.5, 5.0, and 10 mg/kg body wt.

7. The method of claim 1, wherein said hepcidin is administered as a unit dose.

8. The method of claim 7, wherein said unit dose is selected from the group consisting of 50, 55, 60, 65, 70, 75, 100, 125, 150, 175, 200, 225, 250, 275, 300, 325, 350, 400, 450, 500, and 1,000 mg.

9. The method of claim 1, wherein said subject is human.

10. The method of claim 1, wherein said composition is administered before said ischemia reperfusion injury.

11. The method of claim 10, wherein said composition is administered at a range of about 1 minute to about 72 hours before said ischemia reperfusion injury.

12. The method of claim 11, wherein said composition is administered at a range of about 10 minutes to about 48 hours before said ischemia reperfusion injury.

13. The method of claim 12, wherein said composition is administered at a range of about 30 minutes to about 36 hours before said ischemia reperfusion injury.

14. The method of claim 11, wherein said composition is administered at a time selected from the group consisting of 2 hours, 8 hours, 24 hours, and 26 hours before said ischemia reperfusion injury.

15. The method of claim 10, wherein said ischemia reperfusion injury is associated with a transplant in said subject.

16. The method of claim 15, wherein said transplant is a kidney transplant.

17. The method of claim 10, wherein said ischemia reperfusion injury is associated with cardiovascular surgery or sepsis.

18. The method of claim 1, further wherein at least one inducer of hepcidin synthesis, levels, or activity is administered to said subject.

19. The method of claim 18, wherein said inducer of hepcidin is selected from the group consisting of iron, iron-hepcidin complex, copper-hepcidin complex, metal-hepcidin complex, inhibitors of TMPRSS6, plant-derived flavonoids, cytokines, growth factors, steroid hormones, toll-like receptor activation, tyrosine kinase inhibitors, bone morphogenic protein 6 (BMP6), inducers of inflammation, erythroferrone, and minihepcidins.

20. The method of claim 19, wherein said inhibitor of TMPRSS6 is an antisense oligonucleotide or siRNA against Tmprss6, said minihepcidin is PR73 or PR65, said cytokine is IL-6 or IL-22, said growth factor is hepatocyte growth factor or epidermal growth factor, said steroid is estrogen or testosterone, said tyrosine kinase inhibitor is Sorafenib, and said mTOR inhibitor is rapamycin.

21. The method of claim 1, wherein said homology is selected from the group consisting of about 70, 75, 80, 85, 90, 95, 96, 97, 98, and 99%.

22. The method of claim 1, further wherein said pharmaceutical composition optionally comprises a pharmaceutically acceptable carrier and optionally an additional therapeutic agent.

* * * * *